US012217430B2

(12) United States Patent
Cui et al.

(10) Patent No.: US 12,217,430 B2
(45) Date of Patent: Feb. 4, 2025

(54) SYSTEMS AND METHODS FOR PROCESSING X-RAY IMAGES

(71) Applicant: SHANGHAI UNITED IMAGING HEALTHCARE CO., LTD., Shanghai (CN)

(72) Inventors: Kai Cui, Shanghai (CN); Chunhua Jiang, Shanghai (CN); Liang Xu, Shanghai (CN); Shurui Zhao, Shanghai (CN); Jian Zhong, Shanghai (CN); Jie Niu, Shanghai (CN); Yan'ge Ma, Shanghai (CN); Wanli Teng, Shanghai (CN); Na Zhang, Shanghai (CN); Juan Feng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 489 days.

(21) Appl. No.: 17/456,393

(22) Filed: Nov. 24, 2021

(65) Prior Publication Data
US 2022/0092787 A1    Mar. 24, 2022

Related U.S. Application Data

(63) Continuation of application No. PCT/CN2020/091967, filed on May 24, 2020.

(30) Foreign Application Priority Data

May 24, 2019   (CN) .......................... 201910439107.9
Jun. 10, 2019   (CN) .......................... 201910497629.4
(Continued)

(51) Int. Cl.
G06T 7/11      (2017.01)
G06T 7/00      (2017.01)

(52) U.S. Cl.
CPC .............. *G06T 7/11* (2017.01); *G06T 7/0012* (2013.01); *G06T 2207/10116* (2013.01); *G06T 2207/20081* (2013.01); *G06T 2207/20084* (2013.01)

(58) Field of Classification Search
CPC ..................... G06T 7/11; G06T 7/0012; G06T 2207/10116; G06T 2207/20081;
(Continued)

(56) References Cited

U.S. PATENT DOCUMENTS 5,953,444 A    9/1999   Joseph et al.
6,115,487 A    9/2000   Toth et al.
(Continued)

FOREIGN PATENT DOCUMENTS

CN      101105863 A      1/2008
CN      101897592 A     12/2010
(Continued)

OTHER PUBLICATIONS

The Extended European Search Report in European Application No. 20814241.4 mailed on May 30, 2022, 12 pages.
(Continued)

Primary Examiner — Fayyaz Alam
(74) Attorney, Agent, or Firm — METIS IP LLC

(57) ABSTRACT

The present disclosure is related to systems and methods for processing X-ray images. A method for processing an X-ray image may include obtaining an X-ray image; and determining a metal image based on the X-ray image by using a trained metal detection model. The metal image includes information of a metal object in the X-ray image.

20 Claims, 24 Drawing Sheets

(30) Foreign Application Priority Data

| | | | |
|---|---|---|---|
| Jun. 14, 2019 | (CN) | ......................... | 201910515515.8 |
| Aug. 2, 2019 | (CN) | ......................... | 201910712023.8 |
| Dec. 30, 2019 | (CN) | ......................... | 201911400160.4 |
| Mar. 16, 2020 | (CN) | ......................... | 202010180368.6 |

(58) Field of Classification Search
CPC . G06T 2207/20084; G06T 2207/10081; G06T 2207/30004; G06T 7/155; G06T 7/181; G06T 7/187; A61B 6/12; A61B 6/505; A61B 6/5205; A61B 6/5217

See application file for complete search history.

(56) References Cited

U.S. PATENT DOCUMENTS

| | | | |
|---|---|---|---|
| 7,747,058 B2 | 6/2010 | Spahn | |
| 11,379,975 B2* | 7/2022 | Claessen | G06V 10/449 |
| 2004/0196960 A1 | 10/2004 | Tanigawa et al. | |
| 2006/0049358 A1 | 3/2006 | Oumi et al. | |
| 2010/0183214 A1 | 7/2010 | McCollough et al. | |
| 2011/0081071 A1 | 4/2011 | Benson et al. | |
| 2011/0206258 A1 | 8/2011 | Chen et al. | |
| 2012/0250974 A1 | 10/2012 | Miyamoto | |
| 2015/0117740 A1 | 4/2015 | Dong et al. | |
| 2015/0182761 A1 | 7/2015 | Thomson et al. | |
| 2016/0071262 A1 | 3/2016 | Sakimoto | |
| 2018/0137658 A1 | 5/2018 | Zhang et al. | |
| 2018/0240235 A1 | 8/2018 | Mazo | |
| 2018/0336683 A1 | 11/2018 | Feng et al. | |
| 2019/0102605 A1 | 4/2019 | Du | |
| 2021/0000438 A1* | 1/2021 | Wang | A61B 6/5205 |
| 2021/0056688 A1* | 2/2021 | Xu | G06T 11/008 |
| 2021/0110584 A1* | 4/2021 | Claessen | G06T 7/0012 |
| 2022/0121884 A1* | 4/2022 | Zadeh | G06N 3/043 |
| 2022/0122397 A1* | 4/2022 | Cristache | B25J 9/1617 |
| 2022/0180447 A1* | 6/2022 | Kearney | G06N 3/047 |
| 2022/0225952 A1* | 7/2022 | Turner | A61B 6/512 |

FOREIGN PATENT DOCUMENTS

| | | | |
|---|---|---|---|
| CN | 101576997 B | 7/2011 | |
| CN | 102651130 A | 8/2012 | |
| CN | 102819841 A | 12/2012 | |
| CN | 103106675 A | 5/2013 | |
| CN | 103440665 A | 12/2013 | |
| CN | 103700124 A | 4/2014 | |
| CN | 103793905 A | 5/2014 | |
| CN | 104146724 A | 11/2014 | |
| CN | 104665856 A | 6/2015 | |
| CN | 104700421 A | 6/2015 | |
| CN | 105118030 A | 12/2015 | |
| CN | 105608721 A | 5/2016 | |
| CN | 106296615 A | 1/2017 | |
| CN | 106683144 A | 5/2017 | |
| CN | 107578420 A | 1/2018 | |
| CN | 107784647 A | 3/2018 | |
| CN | 107802280 A | 3/2018 | |
| CN | 108010021 A | 5/2018 | |
| CN | 108108739 A | 6/2018 | |
| CN | 108364288 A | 8/2018 | |
| CN | 108535287 A | 9/2018 | |
| CN | 108596861 A | 9/2018 | |
| CN | 108765421 A | 11/2018 | |
| CN | 109242840 A | 1/2019 | |
| CN | 109242849 A | 1/2019 | |
| CN | 109242865 A | 1/2019 | |
| CN | 109363703 A | 2/2019 | |
| CN | 109447990 A | 3/2019 | |
| CN | 109493350 A | 3/2019 | |
| CN | 109509199 A | 3/2019 | |
| CN | 109671095 A | 4/2019 | |
| CN | 109816092 A | 5/2019 | |
| CN | 109872364 A | 6/2019 | |
| CN | 110176010 A | 8/2019 | |
| CN | 110210437 A | 9/2019 | |
| CN | 110246150 A | 9/2019 | |
| CN | 110427466 A | 11/2019 | |
| CN | 110443254 A | 11/2019 | |
| CN | 111053566 A | 4/2020 | |
| JP | 4790031 B2 | 10/2011 | |
| JP | 2015225462 A | 12/2015 | |
| WO | 2016001223 A1 | 1/2016 | |

OTHER PUBLICATIONS

The Second Office Action in Chinese Application No. 202010180368.6 mailed on Sep. 14, 2023, 13 pages.

International Search Report in PCT/CN2020/091967 mailed on Sep. 16, 2020, 8 pages.

Written Opinion in PCT/CN2020/091967 mailed on Sep. 16, 2020, 9 pages.

First Office Action in Chinese Application No. 201910439107.9 mailed on Dec. 28, 2020, 11 pages.

First Office Action in Chinese Application No. 201910497629.4 mailed on Jan. 5, 2021, 23 pages.

First Office Action in Chinese Application No. 201911400160.4 mailed on Jan. 28, 2021, 13 pages.

Fausto Milletari et al., V-Net: Fully Convolutional Neural Networks for Volumetric Medical Image Segmentation, 2016 Fourth International Conference on 3D Vision, 2016, 7 pages.

Assas Ouarda, Image Thresholding Using Type-2 Fuzzy C-Partition Entropy and Particle Swarm Optimization Algorithm, International Conference on Computer Vision and Image Analysis Applications, 2015, 6 pages.

Sha, Sha et al., A Threshold Image Segmentation Algorithm Directed by Edge Information, Journal of Image Graphics, 15(3): 490-494, 2010.

Yang, Min et al., Method of Beam Hardening Correction for CT Reconstruction, Optical Technique, 29(2): 177-178, 182, 2003.

Zhang, Yihai et al., The Methods for Beam Hardening Correction of Cone-beam Industrial Computed Tomography, Nondestructive Testing, 39(6): 8-12, 2017.

Wang, Liming et al., A Universal Method of CT Image Hardening Correction, Journal of Test and Measurement Technology, 19(1): 52-56, 2005.

Richard A. Ketcham et al., Bear Hardening Correction for X-Ray Computed Tomography of Heterogeneous Natural Materials, Computers & Geosciences, 67: 49-61, 2014.

Shubhabrata Sarkar et al., An Empirical Correction Method for Beam-Hardening Artifact in Computerized Tomography (CT) Images, NDT and E International, 102: 104-113, 2019.

Wang, Rong et al., Single Pixel Continuous Edge Detection Method Based on Mathematical Morphology, Journal of Chinese People's Public Security University (Science and Technology), 2013, 5 pages.

Yu, Zhiding et al., CASENet: Deep Category-Aware Semantic Edge Detection, Computer Vision Foundation, 5964-5973, 2017.

Dong, En-Zeng et al., Improved Contour Extraction Algorithm of Infrared Images Based on Active Contour Models, Laser & Infrared, 47(3): 379-384, 2017.

Hui-Fuang Ng et al., An Improved Method for Image Thresholding based on the Valley-Emphasis Method, 2013 Asia-Pacific Signal and Information Processing Association Annual Summit and Conference, 2013, 4 pages.

The Extended European Search Report in European Application No. 24191149.4 mailed on Nov. 20, 2024, 12 pages.

* cited by examiner

700

1700

```
Obtaining a sample set including a plurality of
sample pairs, wherein each sample pair of the
plurality of sample pairs includes a sample X-ray      ~ 1710
image and a reference binary image indicating a
reference metal region with respect to the X-ray
                    image
```

```
Obtaining the trained metal detection model by          ~ 1720
training a preliminary metal detection model based
on the sample set, wherein the preliminary metal
detection model is the neural network model for
       category semantic perception
```

FIG. 17

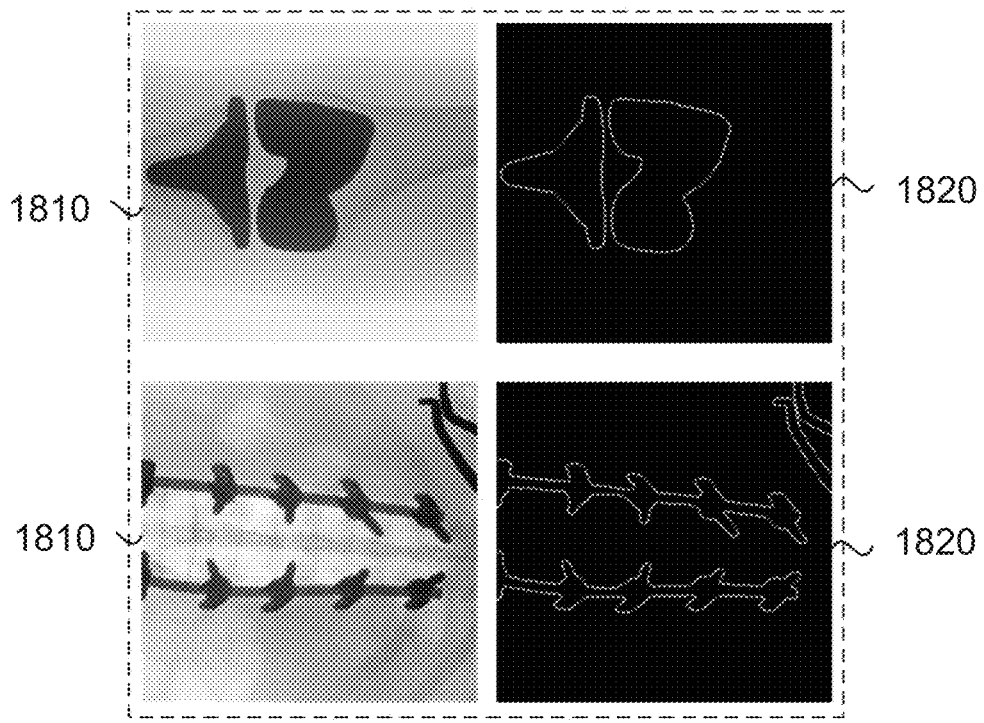

FIG. 18

SYSTEMS AND METHODS FOR PROCESSING X-RAY IMAGES

CROSS-REFERENCE TO RELATED APPLICATIONS

This application is a Continuation of International Application No. PCT/CN2020/091967, filed on May 24, 2020, which claims priority of Chinese Patent Application No. 201910439107.9 filed on May 24, 2019, Chinese Patent Application No. 201910497629.4, filed on Jun. 10, 2019, Chinese Patent Application No. 201910515515.8, filed on Jun. 14, 2019, Chinese Patent Application No. 201910712023.8, filed on Aug. 2, 2019, Chinese Patent Application No. 201911400160.4, filed on Dec. 30, 2019, and Chinese Patent Application No. 202010180368.6, filed on Mar. 16, 2020, the contents of which are incorporated herein in their entirety by reference.

TECHNICAL FIELD

This disclosure generally relates to a medical imaging system, and more particularly, relates to systems and methods for processing X-ray images.

BACKGROUND

A medical imaging system, such as an X-ray imaging device has been widely used in clinical examinations and medical diagnoses in recent years. The X-ray imaging device (e.g., a medical X-ray diagnostic device, a medical X-ray treatment device, a computed tomography (CT) device, etc.) may scan an object (e.g., a tissue, a bone, etc.) using radiation rays and generate one or more images relating to the object. Images of metals (e.g., scissors, forceps, fixation devices, orthopedic surgery equipment, metal implants in a human body, etc.) always appear in the images. It is difficult to distinguish the object and the metals in the images. Therefore, it is desirable to provide systems and methods for processing X-ray images.

SUMMARY

According to an aspect of the present disclosure, a system for processing an X-ray image is provided. The system may include at least one storage device including a set of instructions for processing an X-ray image, and at least one processor in communication with the at least one storage device. The at least one processor is directed to cause the system to perform operations including: obtaining an X-ray image; and determining a metal image based on the X-ray image by using a trained metal detection model. The metal image may include information of a metal object in the X-ray image.

In some embodiments, the trained metal detection model may be determined based on a training process. The training process may include: obtaining a sample set including a plurality of sample pairs, wherein each sample pair of the plurality of sample pairs includes a sample X-ray image and a labeled metal image with respect to the X-ray image; and obtaining the trained metal detection model by training a preliminary metal detection model based on the sample set.

In some embodiments, the at least one processor may also cause the system to obtain a first reference value corresponding to the first feature parameter. The at least one processor may further cause the system to compare the first reference value and the first feature parameter. The at least one processor may still further cause the system to determine whether the medical device is malfunctioning based on the comparison.

In some embodiments, the determining the metal image based on the X-ray image by using the trained metal detection model may include: determining an initial binary image indicating an initial metal region by using the trained metal detection model, wherein the trained metal detection model is trained from a neural network model for category semantic perception; and determining the metal image indicating a target metal region based on the initial binary image, wherein the metal image is a target binary image.

According to another aspect of the present disclosure, a system for processing an X-ray image is provided. The system may include at least one storage device including a set of instructions for processing an X-ray image, and at least one processor in communication with the at least one storage device. The at least one processor is directed to cause the system to perform operations including: obtaining an X-ray image; and determining a metal image from the X-ray image based on gray values associated with the X-ray image.

In some embodiments, the determining the metal image based on gray values associated with the X-ray image may include: determining a target edge region of at least one region of interest (ROI) in the X-ray image; for each of a plurality of pixels in the X-ray image, obtaining a target neighborhood of the pixel; determining a metal edge region based on gray values of pixels in each of a plurality of target neighborhoods corresponding to the plurality of pixels; determining a difference set between the metal edge region and the target edge region; determining a seed point from the first difference set; and determining the metal image by performing a region growth based on the seed point.

In some embodiments, the determining the metal image based on gray values associated with the X-ray image may include: determining a strong gradient image of the X-ray image based on a gradient feature of the X-ray image; determining whether the X-ray image includes metal information based on the X-ray image and the strong gradient image; and in response to a determination that the X-ray image includes the metal information, determining the metal image based on the X-ray image.

According to another aspect of the present disclosure, a system for processing an X-ray image is provided. The system may include at least one storage device including a set of instructions for processing an X-ray image, and at least one processor in communication with the at least one storage device. The at least one processor is directed to cause the system to perform operations including: determining an initial human body region in an X-ray image; determining a threshold image based on pixel values of the initial human body region, wherein a threshold pixel in the threshold image corresponds to one or more pixels in the initial human body region; and determining whether pixels in the initial human body region are target pixels in a target human body region based on the threshold image.

According to another aspect of the present disclosure, a system for X-ray image reconstruction is provided. The system may include at least one storage device including a set of instructions for X-ray image reconstruction, and at least one processor in communication with the at least one storage device. The at least one processor is directed to cause the system to perform operations including: obtaining initial projection data; obtaining an exposure condition corresponding to the initial projection data; determining updated projection data based on at least one target bone-tissue thickness combination, wherein the at least one target bone-tissue thickness combination is obtained by accessing a mapping database based on the initial projection data and the exposure condition; and determining a target X-ray image by performing an image reconstruction based on the updated projection data.

According to another aspect of the present disclosure, a system for processing an X-ray image is provided. The system may include at least one storage device including a set of instructions for processing an X-ray image, and at least one processor in communication with the at least one storage device. The at least one processor is directed to cause the system to perform operations including: obtaining an X-ray image; determining an initial binary image indicating an initial metal region by using a trained metal detection model, wherein the trained metal detection model is trained from a neural network model for category semantic perception; and determining a metal image indicating a target metal region based on the initial binary image, wherein the metal image is a target binary image.

According to another aspect of the present disclosure, a system for processing an X-ray image is provided. The system may include at least one storage device including a set of instructions for processing an X-ray image, and at least one processor in communication with the at least one storage device. The at least one processor is directed to cause the system to perform operations including: obtaining an X-ray image; determining a target edge region of at least one region of interest (ROI) in the X-ray image; for each of a plurality of pixels in the X-ray image, obtaining a target neighborhood of the pixel; determining a metal edge region based on gray values of pixels in each of the plurality of target neighborhoods corresponding to the plurality of pixels; determining a difference set between the metal edge region and the target edge region; determining a seed point from the first difference set; and determining a metal image by performing a region growth based on the seed point.

According to another aspect of the present disclosure, a system for processing an X-ray image is provided. The system may include at least one storage device including a set of instructions for processing an X-ray image, and at least one processor in communication with the at least one storage device. The at least one processor is directed to cause the system to perform operations including: obtaining an X-ray image; determining a strong gradient image of the X-ray image based on a gradient feature of the X-ray image; determining whether the X-ray image includes metal information based on the X-ray image and the strong gradient image; and in response to a determination that the X-ray image includes the metal information, determining the metal image based on the X-ray image.

According to still another aspect of the present disclosure, a method for processing an X-ray image is provided. The method may include obtaining an X-ray image; and determining a metal image based on the X-ray image by using a trained metal detection model, wherein the metal image includes information of a metal object in the X-ray image.

According to still another aspect of the present disclosure, a method for processing an X-ray image is provided. The method may include obtaining an X-ray image; and determining a metal image from the X-ray image based on gray values associated with the X-ray image.

According to still another aspect of the present disclosure, a method for processing an X-ray image is provided. The method may include determining an initial human body region in an X-ray image; determining a threshold image based on pixel values of the initial human body region, wherein a threshold pixel in the threshold image corresponds to one or more pixels in the initial human body region; and determining whether pixels in the initial human body region are target pixels in a target human body region based on the threshold image.

According to still another aspect of the present disclosure, a method for processing an X-ray image is provided. The method may include obtaining initial projection data; obtaining an exposure condition corresponding to the initial projection data; determining updated projection data based on at least one target bone-tissue thickness combination, wherein the at least one target bone-tissue thickness combination is obtained by accessing a mapping database based on the initial projection data and the exposure condition; and determining a target X-ray image by performing an image reconstruction based on the updated projection data.

According to still another aspect of the present disclosure, a method for processing an X-ray image is provided. The method may include obtaining an X-ray image; determining an initial binary image indicating an initial metal region by using a trained metal detection model, wherein the trained metal detection model is trained from a neural network model for category semantic perception; and determining a metal image indicating a target metal region based on the initial binary image, wherein the metal image is a target binary image.

According to still another aspect of the present disclosure, a method for processing an X-ray image is provided. The method may include obtaining an X-ray image; determining a target edge region of at least one region of interest (ROI) in the X-ray image; for each of a plurality of pixels in the X-ray image, obtaining a target neighborhood of the pixel; determining a metal edge region based on gray values of pixels in each of the plurality of target neighborhoods corresponding to the plurality of pixels; determining a difference set between the metal edge region and the target edge region; determining a seed point from the first difference set; and determining a metal image by performing a region growth based on the seed point.

According to still another aspect of the present disclosure, a method for processing an X-ray image is provided. The method may include obtaining an X-ray image; determining a strong gradient image of the X-ray image based on a gradient feature of the X-ray image; determining whether the X-ray image includes metal information based on the X-ray image and the strong gradient image; and in response to a determination that the X-ray image includes the metal information, determining the metal image based on the X-ray image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 17 is a flowchart illustrating an exemplary process for obtaining a trained metal detection model according to some embodiments of the present disclosure;

FIG. 18 illustrates exemplary sample X-ray images and exemplary labeled metal images with respect to each of the sample X-ray images according to some embodiments of the present disclosure;

DETAILED DESCRIPTION

Figure 1:
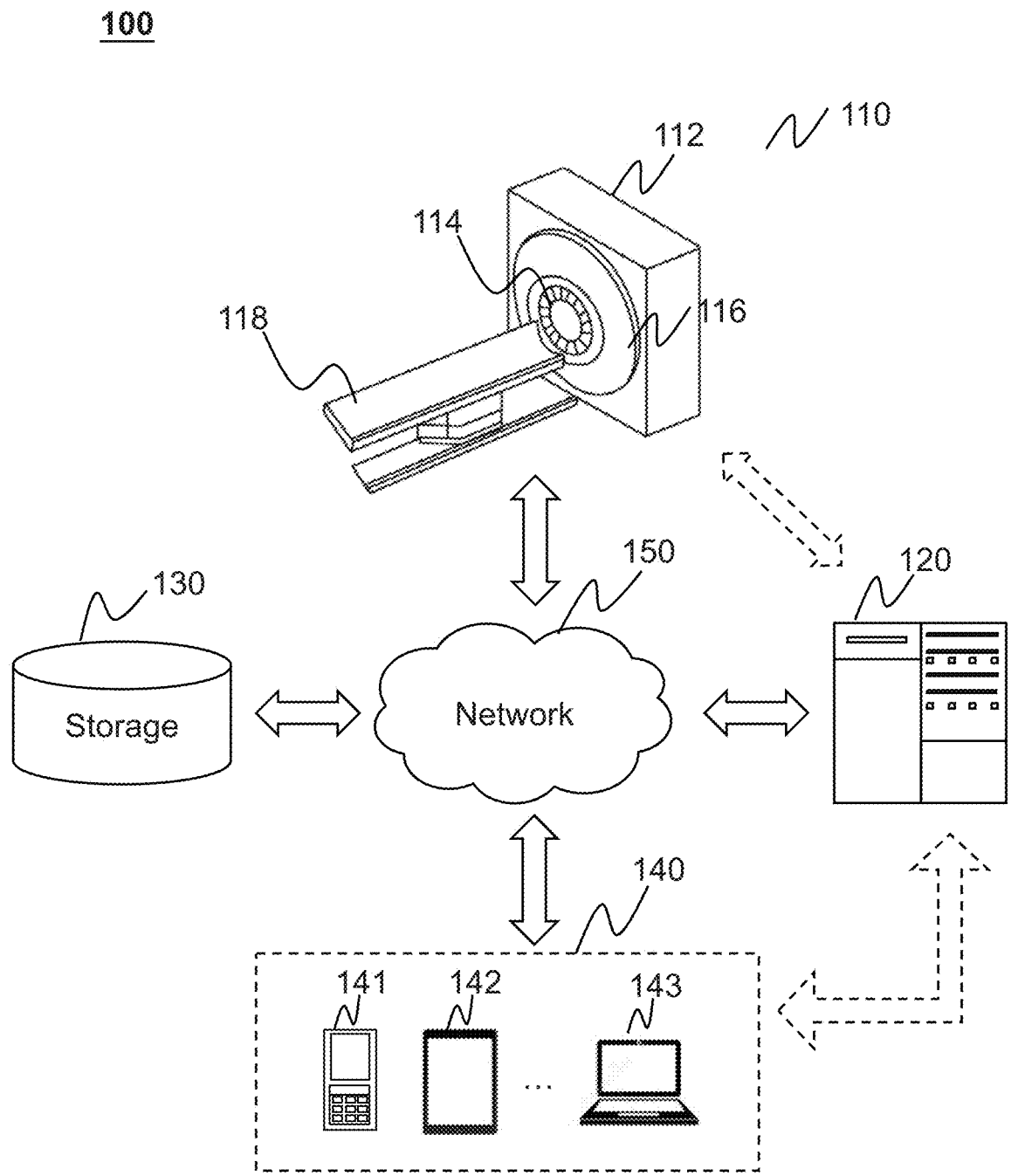
FIG. 1 is a schematic diagram illustrating an imaging system according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements.

Some modules of the system may be referred to in various ways according to some embodiments of the present disclosure, however, any number of different modules may be used and operated in a client terminal and/or a server. These modules are intended to be illustrative, not intended to limit the scope of the present disclosure. Different modules may be used in different aspects of the system and method.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

Technical solutions of the embodiments of the present disclosure be described with reference to the drawings as described below. It is obvious that the described embodiments are not exhaustive and are not limiting. Other embodiments obtained, based on the embodiments set forth in the present disclosure, by those with ordinary skill in the art without any creative works are within the scope of the present disclosure.

Provided herein are systems and methods for processing an X-ray image. According to the present disclosure, the systems and methods may identify a metal image indicating information of a metal object in the X-ray image based on a trained model. The trained model may be trained from a V-Net neural network model or a neural network model for category semantic perception. According to the present disclosure, the systems and methods may determine a seed point from a difference set between a metal edge region determined based gray values of pixels in the X-ray image and a target edge region. The systems and methods may perform a region growth on the seed point to generate a metal image. According to the present disclosure, the systems and methods may determine whether the X-ray image includes information of a metal object based on a gray value at a peak of a gray value histogram of the X-ray image and gray values at gradient positions of a strong gradient image of the X-ray image. According to the present disclosure, the systems and methods may determine a human body region in the X-ray image based on a threshold image fit by segment thresholds of a plurality of sub-regions of an initial human body region. According to the present disclosure, the systems and methods may access a predetermined mapping relation between projection data and a combination of thicknesses of bone and tissue to determine a corrected projection data. The systems and methods may reconstruct the X-ray image based on the corrected projection data. In this way, the metal image and the human body region in the X-ray image may be distinguished accurately and efficiently and the image quality may be improved.

FIG. 1 is a schematic diagram illustrating an exemplary imaging system 100 according to some embodiments of the present disclosure. As shown, the imaging system 100 may include a medical device 110, a processing device 120, a storage 130, one or more client terminal(s) 140, and a network 150. In some embodiments, the medical device 110, the processing device 120, the storage 130, and/or the client terminal(s) 140 may be connected to and/or communicate with each other via a wireless connection (e.g., the network 150), a wired connection, or a combination thereof. The connection between the components in the imaging system 100 may be variable. Merely by way of example, the medical device 110 may be connected to the processing device 120 through the network 150, as illustrated in FIG. 1. As another example, the medical device 110 may be connected to the processing device 120 directly. As a further example, the storage 130 may be connected to the processing device 120 through the network 150, as illustrated in FIG. 1, or connected to the processing device 120 directly. As still a further example, the client terminal(s) 140 may be connected to the processing device 120 through the network 150, as illustrated in FIG. 1, or connected to the processing device 120 directly.

The medical device 110 may be configured to scan an object using radiation rays and generate imaging data used to generate one or more images relating to the object. In some embodiments, the medical device 110 may transmit the imaging data to the processing device 120 for further processing (e.g., identifying a metal image, identifying a human body region, reconstructing the image, etc.). In some embodiments, the imaging data and/or the one or more images associated with the object may be stored in the storage 130 and/or the processing device 120.

In some embodiments, the medical device 110 may be a computed tomography (CT) scanner, a suspended X-ray imaging device, a digital radiography (DR) scanner (e.g., a mobile digital X-ray imaging device), a digital subtraction angiography (DSA) scanner, a dynamic spatial reconstruction (DSR) scanner, an X-ray microscopy scanner, a multi-modality scanner, a C-arm X-ray machine, or the like, or a combination thereof. Exemplary multi-modality scanners may include a computed tomography-positron emission tomography (CT-PET) scanner, a computed tomography-magnetic resonance imaging (CT-MRI) scanner, etc. The object may be biological or non-biological. Merely by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the medical device 110 may include a gantry 112, a detector 114, a radiation source 116, and a table 118. A subject may be placed on the table 118 for scanning In some embodiments, the radiation source 116 may include a tube (not shown in FIG. 1) and a collimator (not shown in FIG. 1). The tube may generate and/or emit radiation beams travelling toward the object. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. In some embodiments, the tube may include an anode target and a filament. The filament may be configured to generate electrons to bombard the anode target. The anode target may be configured to generate the radiation rays (e.g., X-rays) when the electrons bombard the anode target. The collimator may be configured to control the irradiation region (i.e., radiation field) on the object. The collimator may also be configured to adjust the intensity and/or the number of the radiation beams that irradiate on the object.

The detector 114 may detect radiation beams. In some embodiments, the detector 114 may be configured to produce an analog electrical signal that represents the intensity of the received X-rays, including the attenuated beam, as it passes through the object. In some embodiments, the detector 114 may include a plurality of detecting units. The detecting units may include a scintillation detector (e.g., a cesium iodide detector), a gas detector, etc. The plurality of detecting units of the detector may be arranged in any suitable manner, for example, a single row, two rows, or another number of rows.

The processing device 120 may process data and/or information obtained from the medical device 110, the storage 130, and/or the client terminal(s) 140. For example, the processing device 120 may determine a metal image based on an X-ray image obtained from the medical device 110. As another example, the processing device 120 may determine a target human body region based on the X-ray image. As still another example, the processing device 120 may reconstruct the X-ray image to obtain a target X-ray image. In some embodiments, the processing device 120 may be a single server or a server group. The server group may be centralized or distributed. In some embodiments, the processing device 120 may be local or remote. For example, the processing device 120 may access information and/or data from the medical device 110, the storage 130, and/or the client terminal(s) 140 via the network 150. As another example, the processing device 120 may be directly connected to the medical device 110, the client terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage 130 may store data, instructions, and/or any other information. In some embodiments, the storage 130 may store data obtained from the medical device 110, the processing device 120, and/or the client terminal(s) 140. For example, the storage 130 may X-ray images obtained from the medical device 110. As another example, the storage 130 may store trained models for identifying a target (e.g., a metal image, a human body region, etc.). In some embodiments, the storage 130 may store data and/or instructions that the processing device 120 may execute or use to perform exemplary methods described in the present disclosure. In some embodiments, the storage 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the imaging system 100 (e.g., the processing device 120, the client terminal(s) 140). One or more components in the imaging system 100 may access the data or instructions stored in the storage 130 via the network 150. In some embodiments, the storage 130 may be part of the processing device 120.

The client terminal(s) 140 may be connected to and/or communicate with the medical device 110, the processing device 120, and/or the storage 130. For example, the client terminal(s) 140 may obtain image data acquired by the medical device 110 and transmit the image data to the processing device 120 to be processed. As another example, the client terminal(s) 140 may obtain metal images determined by the processing device 120 and display the metal images on a user interface of the client terminal(s) 140. As still another example, the client terminal(s) 140 may obtain target human body regions determined by the processing device 120 and display the target human body regions on the user interface of the client terminal(s) 140. As still another example, the client terminal(s) 140 may obtain a target X-ray image reconstructed by the processing device 120 and display the target X-ray image on the user interface of the client terminal(s) 140. In some embodiments, the client terminal(s) 140 may include a mobile device 141, a tablet computer 142, a laptop computer 143, or the like, or any combination thereof. For example, the mobile device 140-1 may include a mobile phone, a personal digital assistant (PDA), a gaming device, a navigation device, a point of sale (POS) device, a laptop, a tablet computer, a desktop, or the like, or any combination thereof. In some embodiments, the client terminal(s) 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the client terminal(s) 140 may be part of the processing device 120.

The network 150 may include any suitable network that can facilitate the exchange of information and/or data for the imaging system 100. In some embodiments, one or more components of the imaging system 100 (e.g., the medical device 110, the processing device 120, the storage 130, the client terminal(s) 140, etc.) may communicate information and/or data with one or more other components of the imaging system 100 via the network 150. For example, the processing device 120 may obtain an X-ray image from the medical device 110 via the network 150. As another example, the processing device 120 may obtain a trained metal detection model from the storage 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as public cloud, private cloud, community, and hybrid clouds, etc. As another example, the processing device 120 and the client terminal(s) 140 may be integrated into a console. However, those variations and modifications do not depart the scope of the present disclosure.

Figure 2:
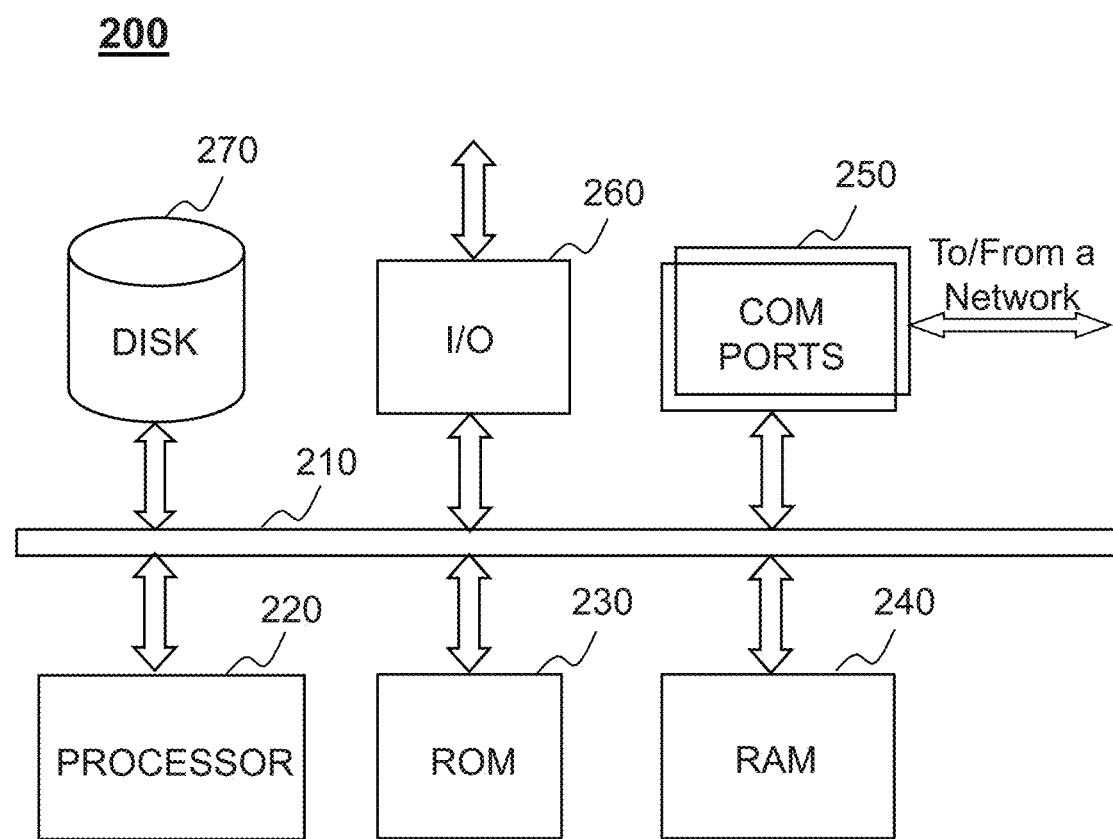
FIG. 2 is a schematic diagram illustrating exemplary hardware and/or software components of an exemplary computing device according to some embodiments of the present disclosure.

FIG. 2 is a schematic diagram illustrating exemplary hardware and software components of a computing device 200 on which the processing device 120, and/or the client terminal(s) 140 may be implemented according to some embodiments of the present disclosure. For example, the processing device 120 may be implemented on the computing device 200 and configured to perform functions of the processing device 120 disclosed in this disclosure.

The computing device 200 may be used to implement a system 100 for the present disclosure. The computing device 200 may be used to implement any component of system 100 that performs one or more functions disclosed in the present disclosure. For example, the processing device 120 may be implemented on the computing device 200, via its hardware, software program, firmware, or a combination thereof. Although only one such computer is shown, for convenience, the computer functions relating to processing an X-ray image as described herein may be implemented in a distributed fashion on a number of similar platforms, to distribute the processing load.

The computing device 200, for example, may include COM ports 250 connected to and from a network connected thereto to facilitate data communications. The COM port 250 may be any network port or data exchange port to facilitate data communications. The computing device 200 may also include a processor (e.g., the processor 220), in the form of one or more processors (e.g., logic circuits), for executing program instructions. For example, the processor may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. The processing circuits may also generate electronic signals including the conclusion or the result and a triggering code. In some embodiments, the trigger code may be in a format recognizable by an operation system (or an application installed therein) of an electronic device in the imaging system 100. For example, the trigger code may be an instruction, a code, a mark, a symbol, or the like, or any combination thereof, that can activate certain functions and/or operations of a mobile phone or let the mobile phone execute a predetermined program(s). In some embodiments, the trigger code may be configured to rend the operation system (or the application) of the electronic device to generate a presentation of the conclusion or the result (e.g., information of a POI) on an interface of the electronic device. Then the interface circuits may send out the electronic signals from the processing circuits via the bus 210.

The exemplary computing device may include the internal communication bus 210, program storage and data storage of different forms including, for example, a disk 270, and a read-only memory (ROM) 230, or a random access memory (RAM) 240, for various data files to be processed and/or transmitted by the computing device. The exemplary computing device may also include program instructions stored in the ROM 230, RAM 240, and/or other type of non-transitory storage medium to be executed by the processor 220. The methods and/or processes of the present disclosure may be implemented as the program instructions. The exemplary computing device may also include operating systems stored in the ROM 230, RAM 240, and/or other type of non-transitory storage medium to be executed by the processor 220. The program instructions may be compatible with the operating systems for providing the online to offline service. The computing device 200 also includes an I/O component 260, supporting input/output between the computer and other components. The computing device 200 may also receive programming and data via network communications.

Merely for illustration, only one processor is illustrated in FIG. 2. Multiple processors are also contemplated; thus, operations and/or method steps performed by one processor as described in the present disclosure may also be jointly or separately performed by the multiple processors. For example, if in the present disclosure the processor of the computing device 200 executes both step A and step B, it should be understood that step A and step B may also be performed by two different processors jointly or separately in the computing device 200 (e.g., the first processor executes step A and the second processor executes step B, or the first and second processors jointly execute steps A and B).

Figure 3:
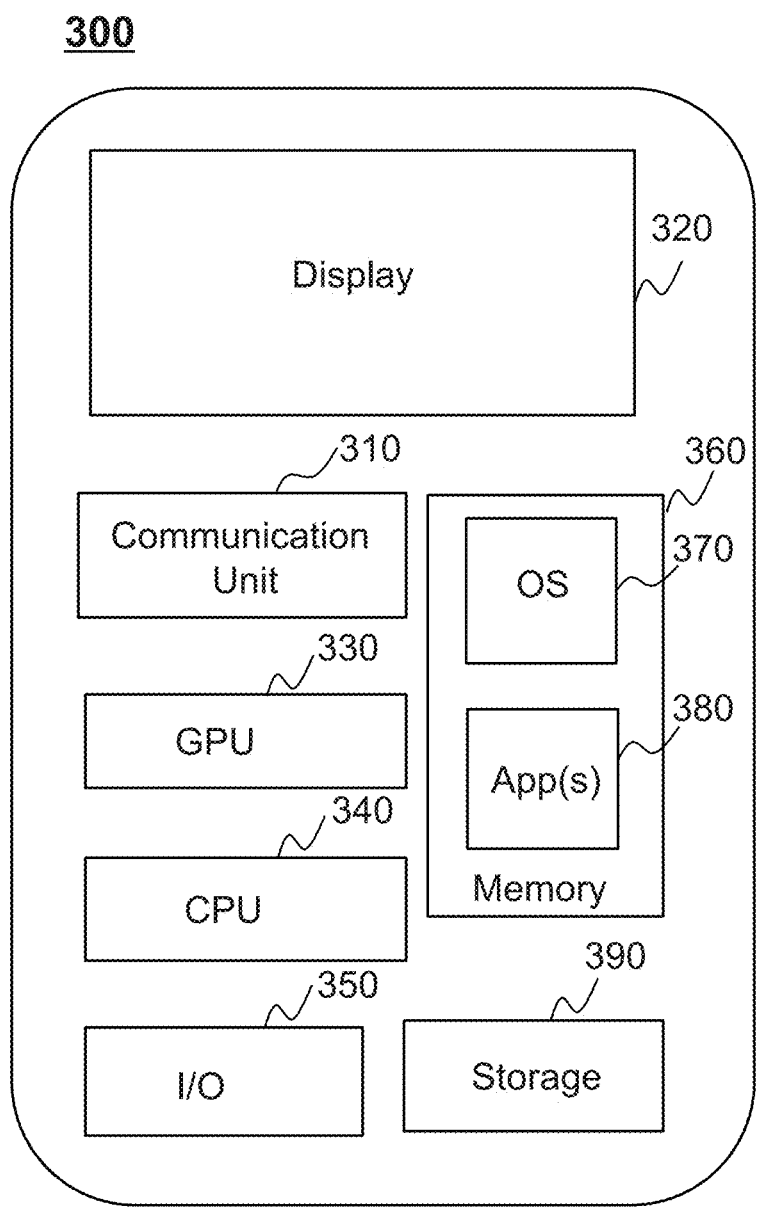
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the client terminal(s) 140 may be implemented according to some embodiments of the present disclosure.

As illustrated in FIG. 3, the mobile device 300 may include a communication platform 310, a display 320, a graphics processing unit (GPU) 330, a central processing unit (CPU) 340, an I/O 350, a memory 360, and a storage 390. The CPU may include interface circuits and processing circuits similar to the processor 220. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to the imaging system 100. User interactions with the information stream may be achieved via the I/O devices 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein (e.g., the imaging system 100, and/or other components of the imaging system 100 described in the present disclosure). The hardware elements, operating systems and programming languages of such computers are conventional in nature, and it is presumed that those skilled in the art are adequately familiar therewith to adapt those technologies to provide a reliability of passing time for a target candidate path as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 4:
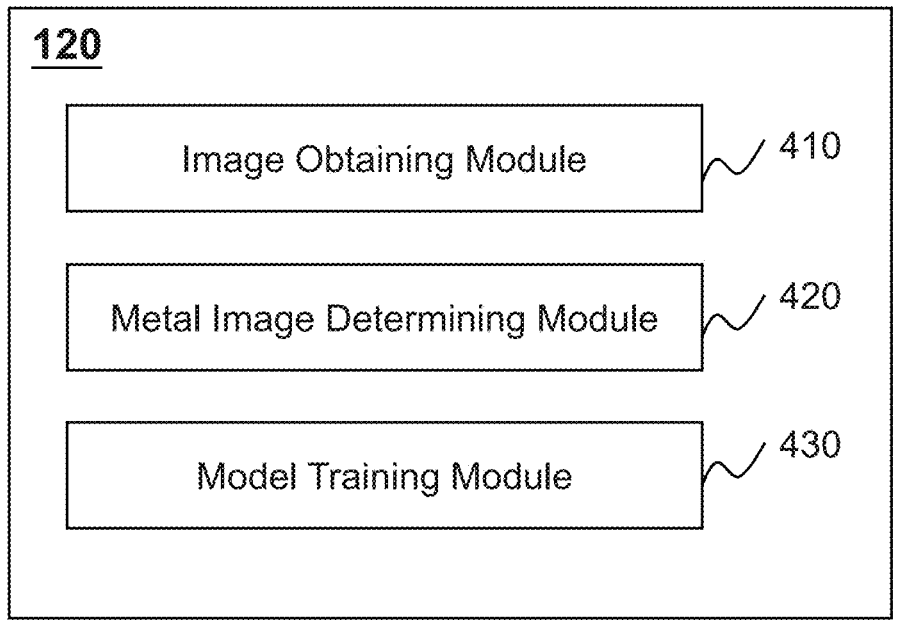
FIG. 4 is a block diagram illustrating an exemplary processing device according to some embodiments of the present disclosure.

FIG. 4 is a block diagram illustrating an exemplary processing device 120 according to some embodiments of the present disclosure. As illustrated in FIG. 4, the processing device 120 may include an image obtaining module 410, a metal image determining module 420, and a model training module 430.

The image obtaining module 410 may be configured to obtain images or image data. For example, the image obtaining module 410 may obtain an X-ray image from the medical device 110 or the storage 130.

The metal image determining module 420 may be configured to determine a metal image in the X-ray image. For example, the metal image determining module 420 may determine a metal image based on the X-ray image by using a trained metal detection model. As another example, the metal image determining module 420 may determine a metal image from the X-ray image based on gray values associated with the X-ray image.

The model training module 430 may be configured to train a preliminary metal detection model to obtain the trained metal detection model. In some embodiments, the preliminary metal detection model may include a deep learning model (e.g., a V-Net neural network model, etc.), a neural network model for category semantic perception, or the like, or any combination thereof.

The modules in the processing device 120 may be connected to or communicate with each other via a wired connection or a wireless connection. The wired connection may be a metal cable, an optical cable, a hybrid cable, or the like, or any combination thereof. The wireless connection may be a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. For example, the metal image determining module 420 may be divided into a plurality of units. As another example, the processing engine 112 may include a storage module (not shown) used to store data and/or information relating to the route planning service.

Figure 5:
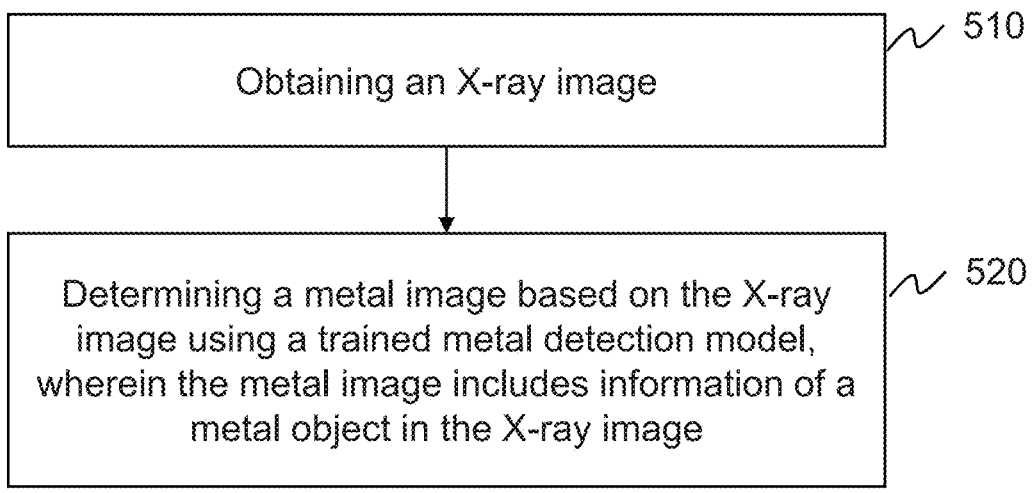
FIG. 5 is a flowchart illustrating an exemplary process for determining a metal image according to some embodiments of the present disclosure.

FIG. 5 is a flowchart illustrating an exemplary process 500 for determining a metal image according to some embodiments of the present disclosure. The process 500 may be executed by the imaging system 100. For example, the process 500 may be implemented as a set of instructions (e.g., an application) stored in the storage ROM 230 or RAM 240. The processor 220 may execute the set of instructions, and when executing the instructions, it may be configured to perform the process 500. The operations of the illustrated process presented below are intended to be illustrative. In some embodiments, the process 500 may be accomplished with one or more additional operations not described and/or without one or more of the operations discussed. Additionally, the order in which the operations of the process as illustrated in FIG. 5 and described below is not intended to be limiting.

In 510, the processing device 120 (e.g., the processor 220, the image obtaining module 410) may obtain an X-ray image.

In some embodiments, the X-ray image may include an image of a target object. The target object may include a human body, a tissue, an organ of the human body, an animal, a plant, a non-living organism, or the like, or any combination thereof. In some embodiments, the X-ray image may be generated by an X-ray imaging technology. In some embodiments, the processing device 120 may obtain the X-ray image from the medical device 110 (e.g., an X-ray machine, an electronic computer tomography (CT) device, a C-arm X-ray machine, a DSA device, etc.). In some embodiments, the processing device 120 may obtain the X-ray image stored in the storage 130. In some embodiments, the X-ray image may be not yet detected whether information of a metal object is included in the X-ray image. In some embodiments, the X-ray image may include or not include information of a metal object.

In 520, the processing device 120 (e.g., the processor 220, the metal image determining module 420) may determine a metal image based on the X-ray image using a trained metal detection model. In some embodiments, the metal image may include information of a metal object in the X-ray image.

In some embodiments, the trained metal detection model may include a machine learning model, a deep learning model, a neural network model, or the like, or any combination thereof. In some embodiments, the machine learning model may include a linear regression algorithm, a ridge regression (an L2 regularized linear regression) algorithm, a Lasso regression (an L1 regularized linear regression) algorithm, a polynomial regression (a nonlinear regression) algorithm, a K-means algorithm, a support vector regression (SVR) algorithm, a support vector machine algorithm, a decision tree algorithm, a fully connected neural network algorithm, and a recurrent neural network algorithm, or the like, or any combination thereof. In some embodiments, the deep learning model may include a convolutional neural network algorithm, a fully convolutional neural network algorithm, and a residual network algorithm, or the like, or any combination thereof. In some embodiments, the fully convolutional neural network algorithm may include a V-Net neural model. In some embodiments, the trained metal detection model may be obtained by inputting a plurality of sample X-ray images and labeled metal images with respect to the plurality of X-ray images into a fully convolutional neural network. Exemplary processes for determining the trained metal detection model may be found elsewhere (e.g., FIG. 7 and the descriptions thereof) in the present disclosure. In some embodiments, the trained metal detection model may be an improved V-Net neural model. Exemplary structures of the improved V-Net neural model may be found elsewhere (e.g., FIG. 10 and the descriptions thereof) in the present disclosure.

In some embodiments, the processing device 120 may determine a probability graph using the trained metal detection model and determine the metal image corresponding to the X-ray image based on the probability graph. In some embodiments, the probability graph may reflect a probability that a pixel (or a pixel block) in the X-ray image belongs to a metal region. In some embodiments, the processing device 120 may determine whether the pixel belongs to the metal region based on the probability of the pixel in the probability graph. For example, if a probability representing a pixel belongs to the metal region is greater than a probability representing that the pixel belongs to a non-metal region, the processing device 120 may determine that the pixel belongs to the metal region.

Figure 6:
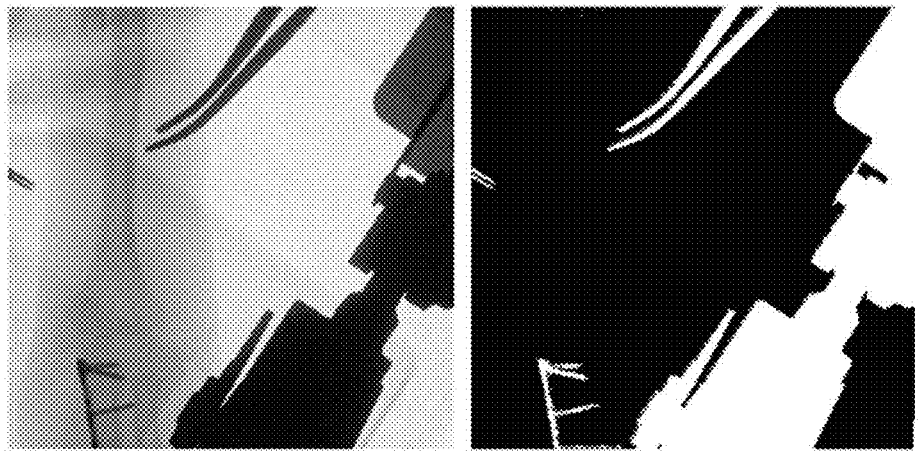
FIG. 6 illustrates an exemplary X-ray image and an exemplary metal image corresponding to the X-ray image according to some embodiments of the present disclosure.

In some embodiments, if the X-ray image includes information of a metal object, the metal image may reflect the information of the metal object. In some embodiments, the information of the metal object may include a position of the metal object, a shape of the metal object, a size of the metal object, an orientation of the metal object, a type of the metal object (e.g., surgical forceps), or the like, or any combination thereof. In some embodiments, the metal image may include a binary image. In some embodiments, pixels in the binary image may include two gray values. For example, the binary image may be a black-and-white image. As another example, the binary image may include any two gray values (e.g., a first gray value equals to 1 and a second gray value equals to 200). By displaying the metal image in a form of the binary image, the metal object may be displayed clearly. FIG. 6 illustrates an exemplary X-ray image and an exemplary metal image corresponding to the X-ray image according to some embodiments of the present disclosure. As shown in FIG. 6, the left image is an X-ray image, and the right image is a metal image corresponding to the X-ray image. In the metal image, the metal region of a metal object is white, and other regions are black.

In some embodiments, the processing device 120 may determine whether the X-ray image includes information of a metal object. For example, if pixels in the X-ray image include two gray values, the processing device 120 may determine that the metal image includes information of the metal object. As another example, if the pixels in the metal image only include one gray value, the processing device 120 may determine that the metal image does not include information of the metal object. In some embodiments, the processing device 120 may further take measures based on the information of the metal object in the X-ray image. In some embodiments, the processing device 120 may send a reminder to a user of the imaging system 100. The reminder may include a determination as to whether the X-ray image includes information of the metal object. For example, in order to attract the user's attention, the processing device 120 may prompt the user that the X-ray image includes information of the metal object. In some embodiments, the processing device 120 may remove a metal region of the metal object from the X-ray image to avoid interference with a diagnosis of the X-ray image. In some embodiments, the processing device 120 may use an automated device (e.g., a manipulator) to grab and/or remove the metal object based on a position of the metal object, a shape of the metal object, a placement orientation of the metal object, etc., displayed in the image.

Figure 7:
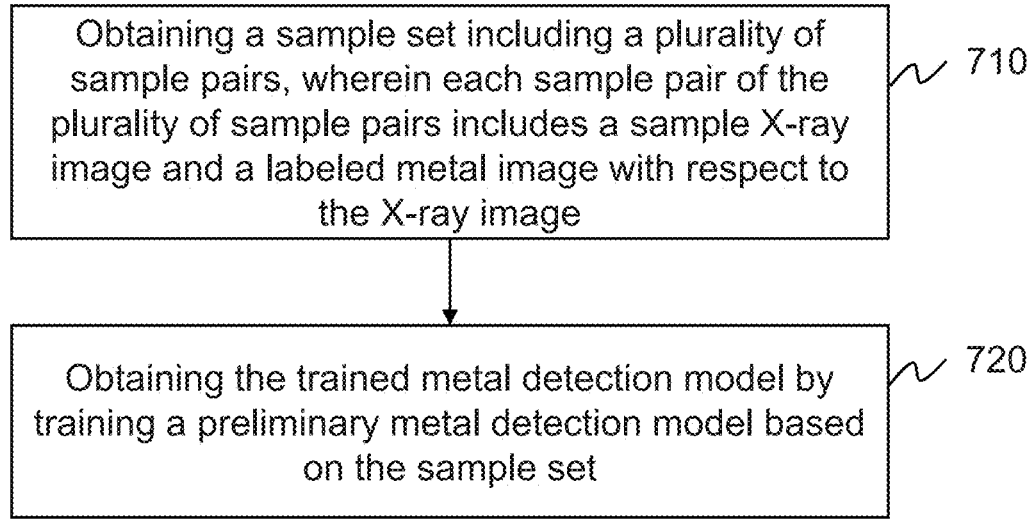
FIG. 7 is a flowchart illustrating an exemplary process for obtaining a trained metal detection model according to some embodiments of the present disclosure.

FIG. 7 is a flowchart illustrating an exemplary process 700 for obtaining a trained metal detection model according to some embodiments of the present disclosure. The process 700 may be executed by the imaging system 100. For example, the process 700 may be implemented as a set of instructions (e.g., an application) stored in the storage ROM 230 or RAM 240. The processor 220 may execute the set of instructions, and when executing the instructions, it may be configured to perform the process 700. The operations of the illustrated process presented below are intended to be illustrative. In some embodiments, the process 700 may be accomplished with one or more additional operations not described and/or without one or more of the operations discussed. Additionally, the order in which the operations of the process as illustrated in FIG. 7 and described below is not intended to be limiting.

In 710, the processing device 120 (e.g., the processor 220, the model training module 430) may obtain a sample set. The sample set may include a plurality of sample pairs. In some embodiments, each sample pair of the plurality of sample pairs may include a sample X-ray image and a labeled metal image with respect to the X-ray image.

In some embodiments, the processing device 120 may obtain the sample X-ray images and the corresponding labeled metal images from the storage 130. In some embodiments, the sample X-ray images may include information of metal objects. The labeled metal images may be generated by a manual labeling method and/or an automatic labeling method. For example, a doctor may determine information of a metal object in the sample X-ray image based on the sample X-ray image, and outline the metal object to obtain the corresponding labeled metal image. As another example, a classification model may be used to automatically label a metal region in the sample X-ray image based on gray values in the X-ray image. A region with gray values greater than a certain threshold may be designated as the metal region. As another example, the sample X-ray image may be labeled by combining the manual labeling method and the automatic labeling method. The sample X-ray image may be divided into several regions by an image segmentation technology, and then the doctor may determine some of the several regions as the metal region.

Figure 8:
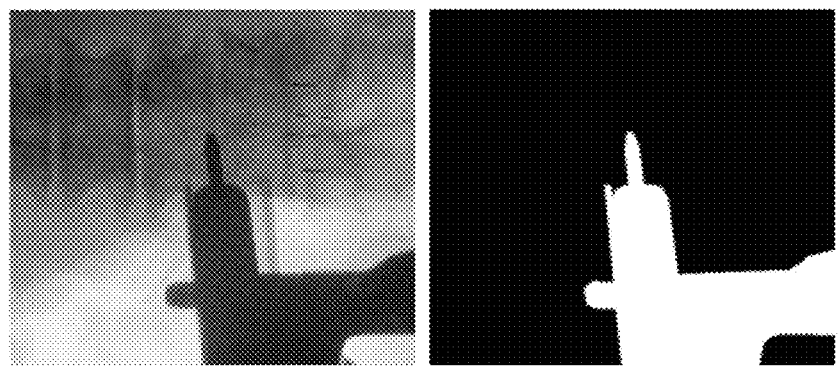
FIG. 8 illustrates an exemplary sample X-ray image and an exemplary labeled metal image with respect to the sample X-ray image according to some embodiments of the present disclosure.
Figure 9:
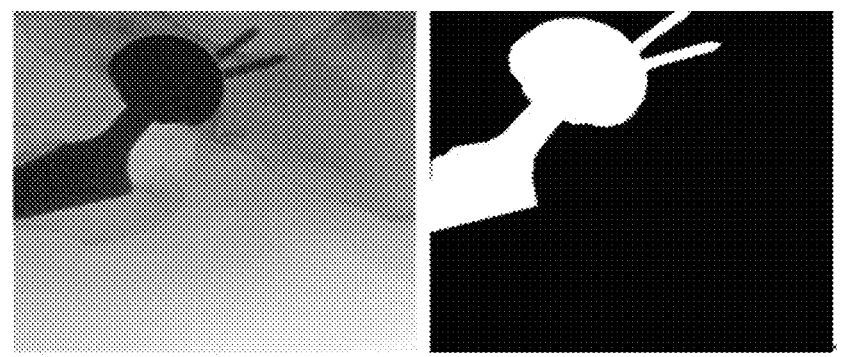
FIG. 9 illustrates an exemplary sample X-ray image and an exemplary labeled metal image with respect to the sample X-ray image according to some embodiments of the present disclosure.

In some embodiments, the labeled metal image may be a binary image (e.g., a black-and-white image). FIG. 8 illustrates an exemplary sample X-ray image and an exemplary labeled metal image with respect to the sample X-ray image according to some embodiments of the present disclosure. FIG. 9 illustrates an exemplary sample X-ray image and an exemplary labeled metal image with respect to the sample X-ray image according to some embodiments of the present disclosure. As shown in FIGS. 8-9, the left images are sample X-ray images, and the right images are labeled metal images with respect to the sample X-ray images at the left. In the labeled metal images, metal regions are white, and other regions are black. By displaying the labeled metal image in a binary image, metal objects may be displayed clearly.

In some embodiments, the processing device 120 may normalize the sample X-ray images to facilitate training and convergence of a deep neural network (e.g., a V-Net neural model). In some embodiments, a normalization of the sample X-ray images may be performed according to the Equation (1):

$$I' = \frac{I - \mu}{\sigma}, \tag{1}$$

wherein I denotes a gray value of a pixel, μ denotes an average value of the gray values of pixels in the sample X-ray image, σ denotes a standard deviation of the gray values of pixels in the sample X-ray image, and I' denotes a normalized gray value.

In 720, the processing device 120 (e.g., the processor 220, the model training module 430) may obtain the trained metal detection model by training a preliminary metal detection model based on the sample set.

In some embodiments, the preliminary metal detection model may include a deep learning model (e.g., a fully convolutional neural network), a V-Net neural network, or the like, or any combination thereof. In some embodiments, the V-Net neural network may include a skip connection. The skip connection may include combining at least one of at least one down-sampling feature corresponding to at least one down-sampling layer during up-sampling.

In some embodiments, a loss function of the V-Net neural network may include an FL Loss. In some embodiments, a value of the FL Loss function may be determined based on a computing result (e.g., by a weighted summation, an average value, etc.) of a value of a Focal Loss function and a value of a Lovasz Loss function. For example, the value of the FL Loss function may be determined according to Equation (2):

FL Loss=λ*Focal Loss+β*Lovasz Loss (2), wherein FL Loss denotes a value of the FL Loss function, Focal Loss denotes a value of the Focal Loss function, Lovasz Loss denotes a value of the Lovasz Loss function, and λ and β denote weight values of the Focal Loss function and the Lovasz Loss function, respectively. In some embodiments, λ and β may be determined according to application scenarios. For example, a ratio of λ and β may be 0.8/0.2.

In some embodiments, the Focal loss function may pay more attention to a classification of pixels, and may adapt to a complex metal detection situation. The Lovasz loss function may pay more attention to reducing a global structure difference between an X-ray image and a training template (e.g., a labeled metal image corresponding to the X-ray image). The FL loss function, which combines the Focal loss function and the Lovasz Loss function, may have the advantages thereof, thereby improving a recognition accuracy of the trained metal detection model.

In some embodiments, an optimizer for training the V-Net neural network may include an Adam algorithm. In the training process, a learning rate decay strategy may be used. The learning rate decay strategy may deduce a learning rate of the V-Net neural network every fixed epoch. Exemplary structures of the improved V-Net neural model may be found elsewhere (e.g., FIG. 10 and the descriptions thereof) in the present disclosure.

Figure 10:
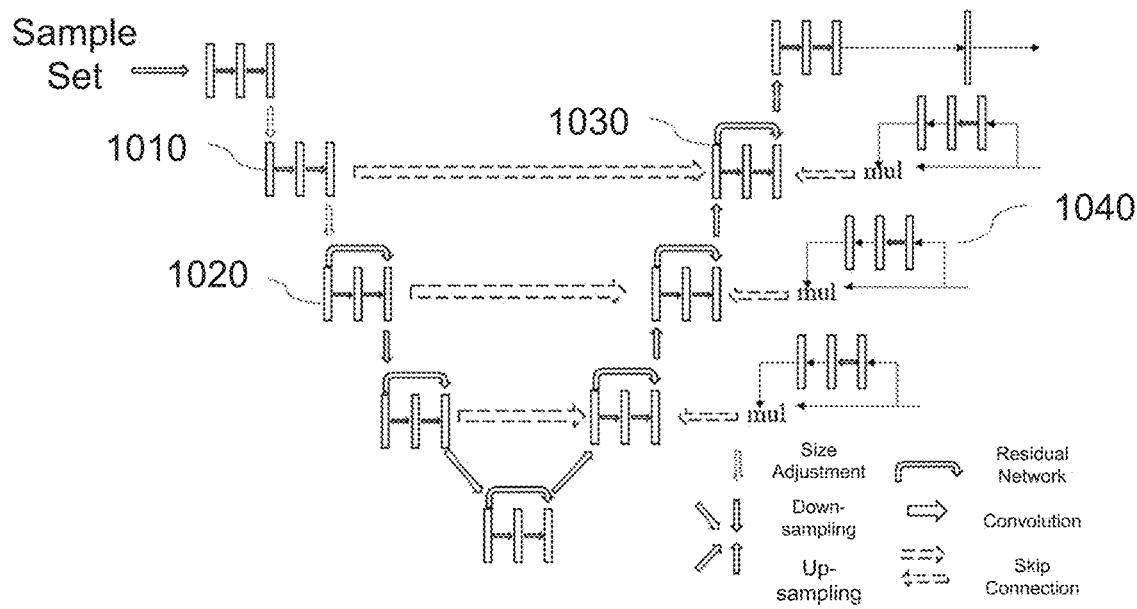
FIG. 10 is a schematic diagram illustrating an exemplary V-Net neural model according to some embodiments of the present disclosure.

FIG. 10 is a schematic diagram illustrating an exemplary V-Net neural model according to some embodiments of the present disclosure. As shown in FIG. 10, the V-Net neural model may include an image resizing module 1010, a down-sampling module 1020, an up-sampling module 1030, and a feature refining module 1040.

In some embodiments, the image resizing module 1010 may include a plurality of convolution layers. An image resolution of the X-ray image may be reduced after being processed by the plurality of convolution layers, thereby improving a model training efficiency and a testing efficiency without losing image features of the X-ray image. In some embodiments, the image resizing module 1010 may include a BNorm batch normalization layer to accelerate a training convergence. In some embodiments, the image resizing module 1010 may include a ReLU activation function to solve a gradient dissipation in the V-Net neural networks. In some embodiments, there may be one or more image resizing modules 1010. In some embodiments, a processing result of the image resizing module 1010 may be an image feature mapping matrix corresponding to image pixels after being processed by a convolution operation.

In some embodiments, the down-sampling module 1020 may be used to extract image features. The image features may include an edge feature of the X-ray image, an outline feature of the X-ray image, a semantic feature of the X-ray image, or the like, or any combination thereof. In some embodiments, the down-sampling module 1020 may be composed of a residual block with a convolution kernel size of 3×3 or 5×5 to reuse the image features when extracting the image features. Extracting inaccurate image features due to a loss of a parameter gradient is avoided. In some embodiments, the down-sampling module 1020 may include a BNorm batch normalization layer to accelerate the training convergence. In some embodiments, the down-sampling module 1020 may include a ReLU activation function to solve the gradient dissipation in the V-Net neural network. In some embodiments, there may be one or more down-sampling modules 1020. In some embodiments, a processing result of the down-sampling module 1020 may be an image feature mapping matrix corresponding to image pixels after being processed by a convolution operation.

In some embodiments, the up-sampling module 1030 may include one or more transposed convolution layers (also called deconvolution layers) and one or more residual blocks. The one or more residual block may reuse the image features to avoid extracting inaccurate image features due to a loss of a parameter gradient. The transposed convolution layer may restore the image features. In some embodiments, the up-sampling module 1030 may include a plurality of convolution layers and residual blocks. The image features may be restored using a convolution operation and an interpolation algorithm on the image features. The interpolation algorithm on the image features may include a linear interpolation, a bilinear interpolation, or the like, or any combination thereof. In some embodiments, the up-sampling module 1030 may include a BNorm batch normalization layer to accelerate the training convergence. In some embodiments, the up-sampling module 1030 may include a ReLU activation function to solve the gradient dissipation in the V-Net neural network. In some embodiments, there may be one or more up-sampling modules 1030. For example, a count of up-sampling modules 1030 may equal to a count of down-sampling modules 1020. In some embodiments, a processing result of the up-sampling module 1030 may be an image feature mapping matrix corresponding to image pixels after being processed by a deconvolution operation or the convolution operation and the interpolation algorithm.

In some embodiments, when the up-sampling module 1030 restoring the image features, the up-sampling module 1030 may further include a skip connection to avoid a loss of image features. Image detail information may be restored. In some embodiments, the skip connection may include combing at least one of at least one down-sampling feature corresponding to at least one down-sampling layer during up-sampling. For example, during each up-sampling, image features of a down-sampling layer at the same level as the corresponding up-sampling layer may be combined in the corresponding up-sampling. In some embodiments, the V-Net model may further include a feature refining module 1040. The feature refining module 1040 may be used to perform a feature refining on the down-sampling features corresponding to at least one down-sampling layer in the skip connection. In some embodiments, during each up-sampling, the skip connection may include combing a down-sampling feature of a down-sampling layer corresponding to the up-sampling layer and a refined feature of the down-sampling feature. For example, during each up-sampling, the skip connection may include determining a product of the down-sampling feature and the refined result of the down-sampling feature, and combining the product in the corresponding up-sampling. In some embodiments, the down-sampling feature may be refined to obtain the refined feature by the feature refining module 1040.

In some embodiments, the feature refining module 1040 may be configured to extract global information in the image features. The feature refining module 1040 may include a global pooling layer, a convolution layer, and a sigmoid activation function. In some embodiments, the product of the down-sampling feature and the refined result may be a result of a feature matrix composed of pixels of an image outputted by the down-sampling and a weight matrix of the refined result (e.g., a 1×1×C matrix). The feature refining module 1040 may optimize the output image features at each down-sampling layer, thereby making it easier to integrate global information and output a weight corresponding to the global feature information. In some embodiments, a calculation speed of the feature refining module 1040 is fast, thereby reducing calculation time. In some embodiments, by combining the image features of down-sampling in the corresponding up-sampling, image details may be well restored.

In some embodiments, the V-Net model may further include classifying a processing result of the up-sampling module 1030. In some embodiments, classification probabilities may be determined by classifying the processing result of the up-sampling module 1030 using a softmax function.

Figure 11:
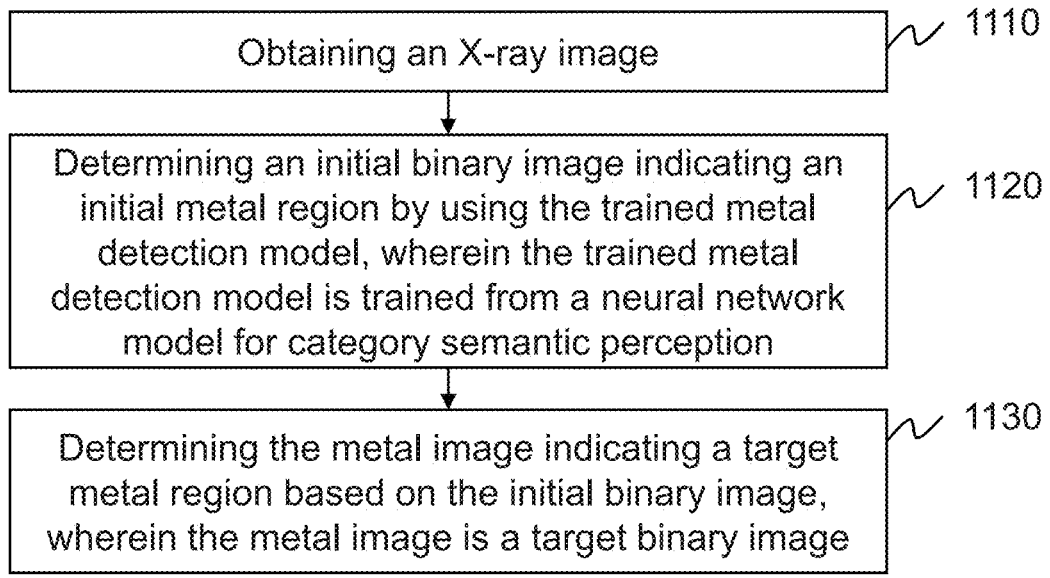
FIG. 11 is a flowchart illustrating an exemplary process for determining a metal image according to some embodiments of the present disclosure.

FIG. 11 is a flowchart illustrating an exemplary process 1100 for determining a metal image according to some embodiments of the present disclosure. The process 1100 may be executed by the imaging system 100. For example, the process 1100 may be implemented as a set of instructions (e.g., an application) stored in the storage ROM 230 or RAM 240. The processor 220 may execute the set of instructions, and when executing the instructions, it may be configured to perform the process 1100. The operations of the illustrated process presented below are intended to be illustrative. In some embodiments, the process 1100 may be accomplished with one or more additional operations not described and/or without one or more of the operations discussed. Additionally, the order in which the operations of the process as illustrated in FIG. 11 and described below is not intended to be limiting.

In 1110, the processing device 120 (e.g., the processor 220, the image obtaining module 410) may obtain an X-ray image.

Figure 12:
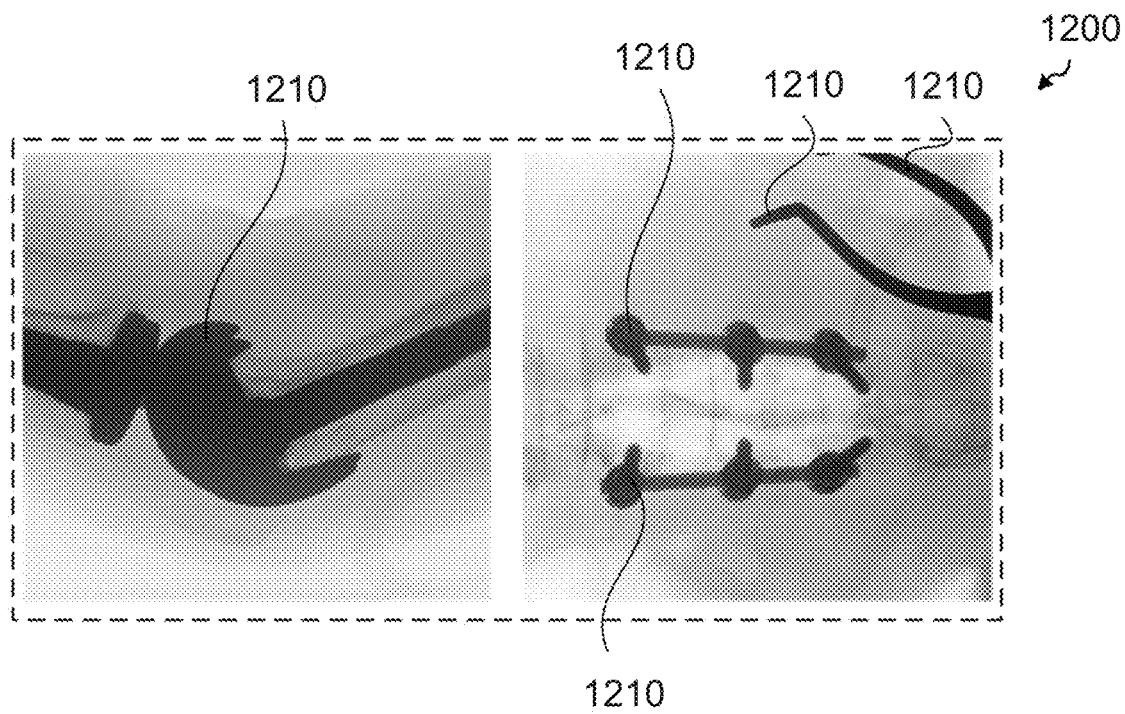
FIG. 12 illustrates an exemplary X-ray image according to some embodiments of the present disclosure.

In some embodiments, the X-ray image may include or not include information of a metal object. FIG. 12 illustrates an exemplary X-ray image 1200 according to some embodiments of the present disclosure. As shown in FIG. 12, the X-ray image 1200 may include a plurality of block regions 1210. The block regions 1210 may include the information of metal objects.

In some embodiments, the processing engine 112 may obtain an original image from the medical device 110 (e.g., an X-ray machine, an electronic computer tomography (CT) device, a C-arm X-ray machine, a DSA device, etc.) or the storage 130, and pre-process the original image to obtain the X-ray image. In some embodiments, the pre-processing of the original image may include a grayscale normalization and an image boundary filling.

In some embodiments, a trained metal detection model may be used to detect whether the X-ray image includes information of a metal object. The pre-processing of the original image may include processing the original image to satisfy an input requirement of the trained metal detection model. For example, the pre-processing of the original image may include a grayscale normalization and an image size processing of an image boundary filling. The pre-processed initial image (i.e., the X-ray image) may be inputted into the trained metal detection model.

In 1120, the processing device 120 (e.g., the processor 220, the metal image determining module 420) may determine an initial binary image of the X-ray image by using the trained metal detection model. The initial binary image may indicate an initial metal region.

Figure 13:
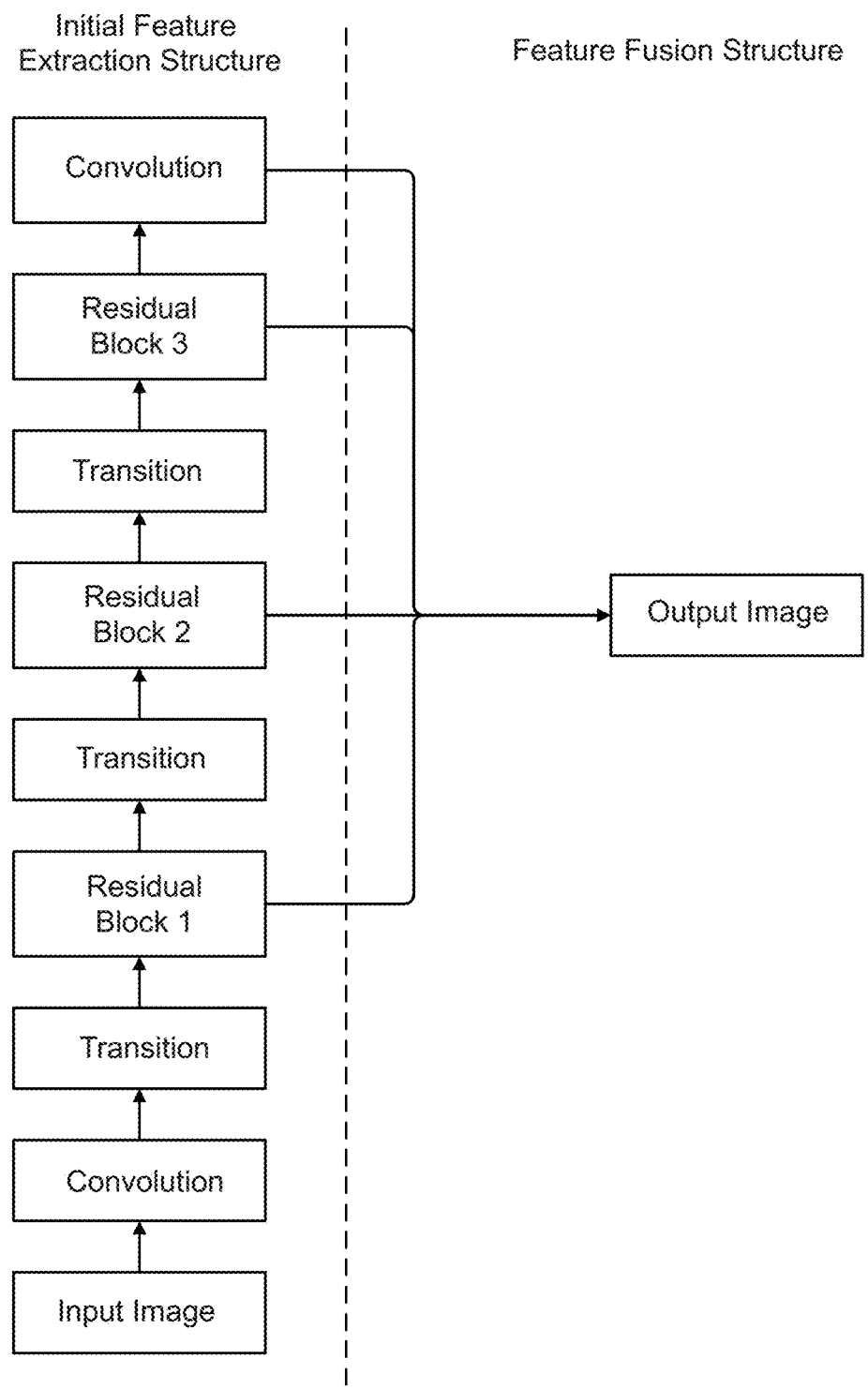
FIG. 13 is a schematic diagram illustrating an exemplary structure of a neural network model for category semantic perception according to some embodiments of the present disclosure.

In some embodiments, the trained metal detection model may be a model used for determining a metal image with respect to the X-ray image. For example, the trained metal detection model may be trained from a neural network model for category semantic perception. The neural network model for category semantic perception may be a deep neural network model capable to recognize different types of target objects. FIG. 13 is a schematic diagram illustrating an exemplary structure of a neural network model for category semantic perception according to some embodiments of the present disclosure. As shown in FIG. 13, the neural network model for category semantic perception may include an initial feature extraction structure and a feature fusion structure.

In some embodiments, the initial feature extraction structure may be used to extract initial features from the X-ray image. An image outputted by a residual block 1, a residual block 2, a residual block 3, a second convolution operation may be an extracted result of the initial features. The residual blocks may include a skip connection structure to reduce a loss of feature information and prevent failing to train the neural network model caused by a disappearance of a gradient during updating parameters of the neural network model. A training efficiency of the neural network model is improved.

In some embodiments, the feature fusion structure may fuse the extracted initial features to output a fusion image. The neural network model for category semantic perception may be an improved neural network model for category semantic perception. For example, based on the initial feature extraction structure, a secondary feature extraction structure may be added into the neural network model to improve a feature extraction accuracy.

Figure 14:
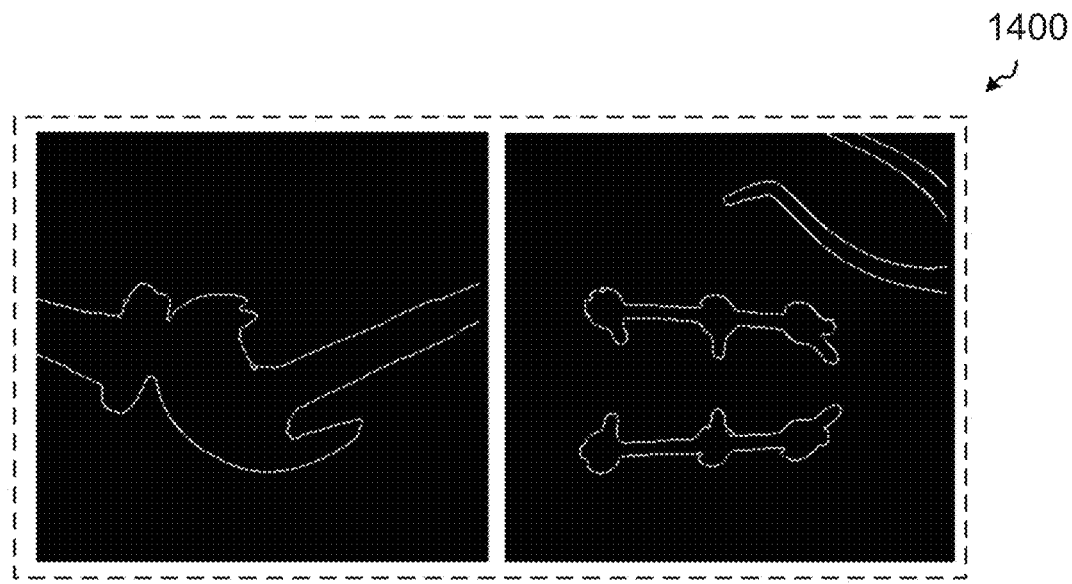
FIG. 14 illustrates an exemplary initial binary image according to some embodiments of the present disclosure.

FIG. 14 illustrates an exemplary initial binary image 1400 according to some embodiments of the present disclosure. In some embodiments, the processing device 120 may input the X-ray image (e.g., the X-ray image 1200 in FIG. 12) into the trained metal detection model to obtain the initial binary image (e.g., the initial binary image 1400 in FIG. 14). Different values in the initial binary image may indicate an edge of a metal region and a non-metal edge of other image contents. For example, a white edge may indicate an edge of a metal region, and a black region may indicate a non-metal edge of other image contents. In some embodiments, due to an error of the trained metal detection model, the edge of a metal region in the output image of the trained metal detection model may be incomplete, so the extracted edge of a metal region herein may be referred to as an initial edge of an initial metal region, and the output image of the trained metal detection model may be referred to as an initial binary image.

In 1130, the processing device 120 (e.g., the processor 220, the metal image determining module 420) may determine the metal image indicating a target metal region based on the initial binary image. In some embodiments, the metal image is a target binary image.

Figure 15:
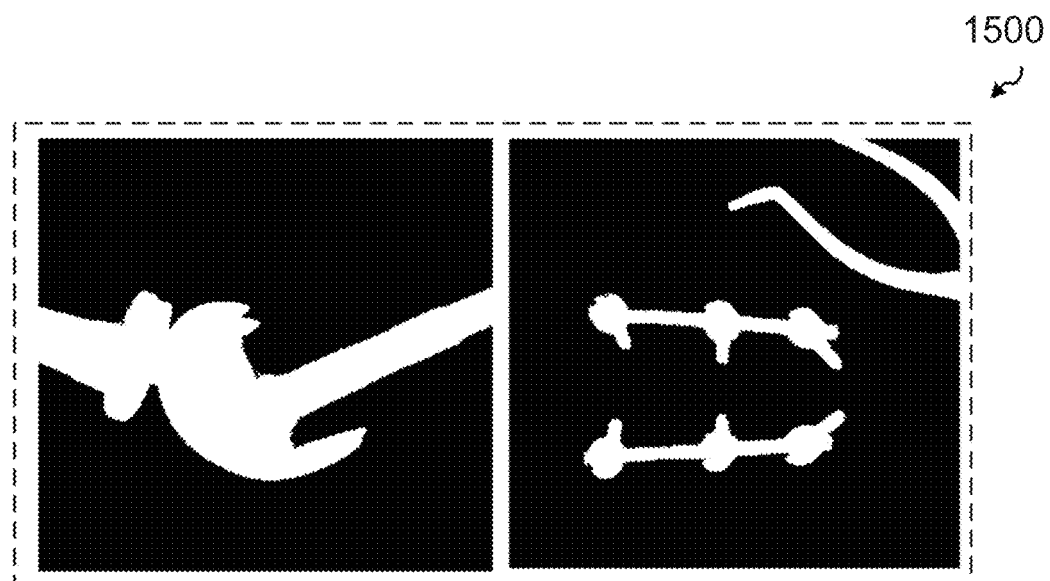
FIG. 15 illustrates an exemplary target binary image according to some embodiments of the present disclosure.

In some embodiments, to completely mark the target metal region in the initial binary image, the processing device 120 may post-process the initial binary image. FIG. 15 illustrates an exemplary target binary image 1500 according to some embodiments of the present disclosure. The post-processing may be used to correct the initial edge of the initial metal region and fill a region within the target region edge to generate the target binary image (e.g., the target binary image 1500 in FIG. 15) having a completely marked metal region. In some embodiments, the post-processing may include an image denoising, an edge connection, a region filling, or the like, or any combination thereof. As shown in FIG. 15, a white region may be the target metal region of the X-ray image (e.g., the X-ray image 1200 in FIG. 12). A black region may be a non-metal of the X-ray image (e.g., the X-ray image 1200 in FIG. 12).

In some embodiments, the post-processing of the initial binary image to obtain the target binary image may include the following operations. For example, the processing device 120 may determine whether the initial metal region is a connected region. If the initial metal region is the connected region, the processing device 120 may obtain the target metal region by filling the initial metal region according to a morphological reconstruction algorithm. The target binary image may be generated by marking the target metal region.

In some embodiments, the processing device 120 may determine whether a region within the initial edge of the initial metal region is a connected region. If the region within the initial edge of the initial metal region is a connected region, the processing device 120 may designate the initial edge of the initial metal region as a corrected edge of the initial metal region, and may not correct the initial edge of the initial metal region. The processing device 120 may generate the target metal region by filling the region within the initial edge of the initial metal region with a value equals to a value of the initial edge of the initial metal region using the morphological reconstruction algorithm. The initial binary image after filling the region within the initial edge of the initial metal region may be the target binary image.

In some embodiments, if the initial metal region is a dis-connected region, the processing device 120 may generate a complete edge (or a target region edge) by performing an edge connection processing on the initial edge of the initial metal region using a predetermined edge processing algorithm. The processing device 120 may generate the target metal region by filling a region within the complete edge (or the target region edge) using the morphological reconstruction algorithm. The target binary image may be generated by marking the target metal region.

In some embodiments, the processing device 120 may determine whether a region within the initial edge of the initial metal region is a dis-connected region. If the region within the initial edge of the initial metal region is a dis-connected region, the processing device 120 may determine that the initial edge of the initial metal region may be incomplete. The initial edge may need to be corrected. The processing device 120 may generate the complete edge (or the target region edge) of the metal region may be generated by connecting the initial edge of the target metal region using a predetermined edge processing algorithm (e.g., an expansion algorithm, a boundary tracking algorithm, a region generation algorithm, etc.). The region within the complete edge (or the target region edge) of the target metal region may be the connected region. The processing device 120 may generate the target binary image by filling the connected region within the complete edge (or the target region edge) with a value equals to a value of the complete edge (or the target region edge) using the morphological reconstruction algorithm. In this way, the target metal region in the target binary image may be marked accurately.

In some embodiments, using the trained metal detection model to detect information of metal objects may effectively detect the target metal region using a smaller radiation dose. The accuracy and efficiency of detecting the target metal region may be improved, thereby reducing a radiation dose to a human body. The image quality is improved.

Figure 16:
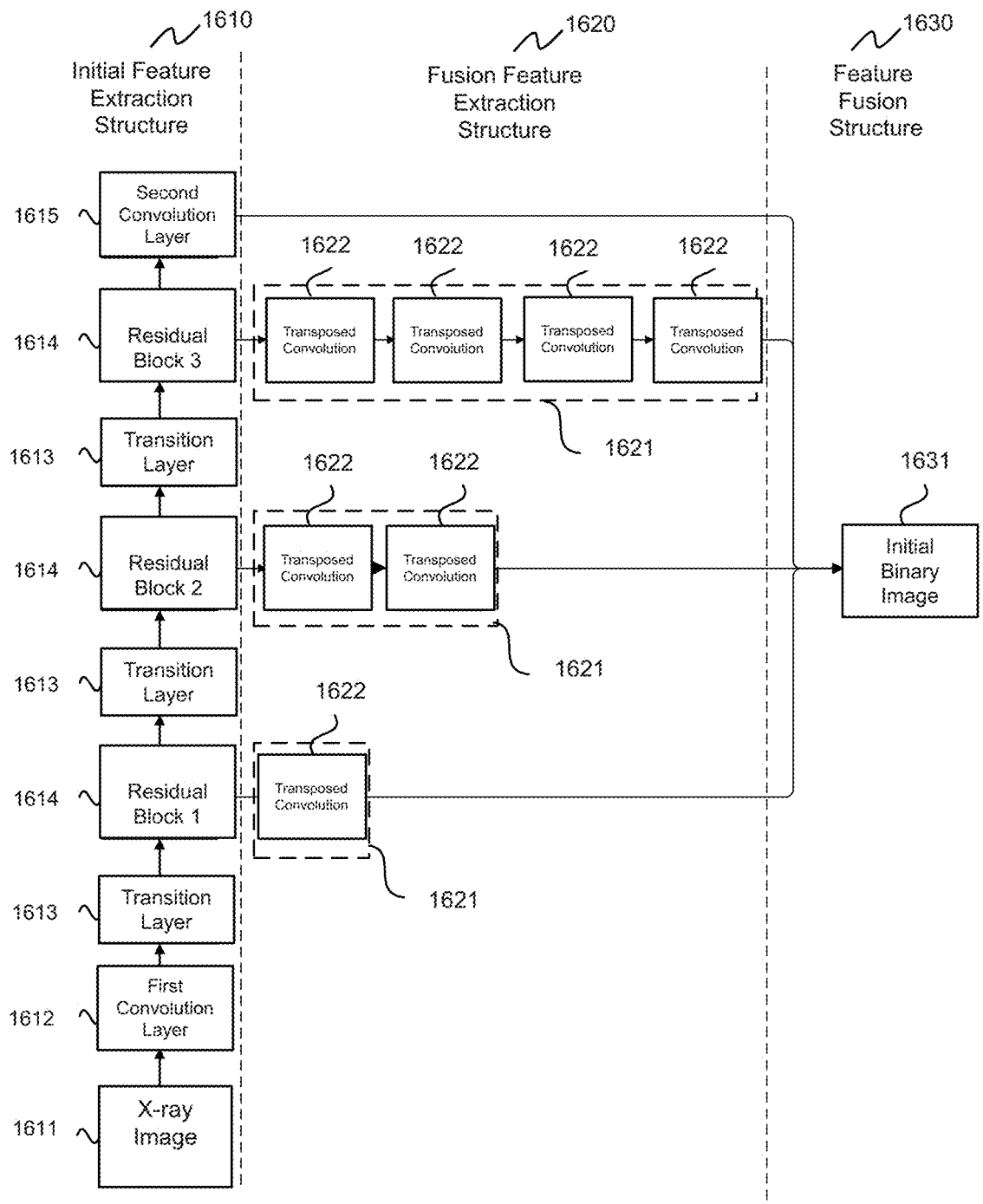
FIG. 16 is a schematic diagram illustrating an exemplary structure of an improved neural network model for category semantic perception according to some embodiments of the present disclosure.

FIG. 16 is a schematic diagram illustrating an exemplary structure of an improved neural network model for category semantic perception according to some embodiments of the present disclosure. As shown in FIG. 16, the improved neural network model for category semantic perception may include an initial feature extraction structure 1610, a fusion feature extraction structure 1620, and a feature fusion structure 1630.

In some embodiments, the initial feature extraction structure 1610 may be configured to initially extract edge features of the initial metal region from the X-ray image 1611. The initial feature extraction structure 1610 may include a first convolution layer 1612, at least three transition layers 1613, a plurality of residual blocks 1614, and a second convolution layer 1615. In some embodiments, each of the plurality of residual blocks 1614 may connect to a respective one of the at least three transition layers 1613. Each of the least three transition layers 1613 may include interpolations and convolutions. Each residual block 1614 may be used to generate a first initial feature and the second convolutional layer 1615 may be used to generate a second initial feature. That is, an output image of each residual block 1614 and the second convolutional layer 1615 may be initial features that are initially extracted.

In some embodiments, the fusion feature extraction structure 1620 may be used to perform a secondary feature extraction on the first initial feature generated by the residual block 1614 to further extract edge features of the initial metal region. The fusion feature extraction structure 1620 may include at least one up-sampling layer 1621. In some embodiments, each of the at least one up-sampling layer 1621 may include at least one transposed convolution 1622. Each of the up-sampling layer 1621 may connect to a residual block 1614 of the plurality of residual blocks 1614. In some embodiments, the up-sampling layer 1621 may be used to generate a fusion feature by performing a secondary feature extraction on the first initial feature generated by the residual block 1614. In some embodiments, a first count of the at least one up-sampling layer 1621 in the fusion feature extraction structure 1620 may be greater than or equal to 1, and less than or equal to a second count of the plurality of residual blocks 1614 in the initial feature extraction structure 1610. The greater the first count of up-sampling layers is, the more accurate and comprehensive an extraction of the fusion feature may be. An output image of each up-sampling layer 1621 may be a fusion feature, which is generated by performing the secondary feature extraction on the first initial feature.

In some embodiments, the feature fusion structure 1630 may connect to the second convolution layer 1615 and each up-sampling layer 1621. The feature fusion structure 1630 may be used to generate an initial binary image 1631 by fusing the second initial feature generated by the second convolution layer 1615 and the fusion feature generated by each of the at least one up-sampling layer 1621.

In some embodiments, an improved neural network model for category semantic perception may add at least one neural network layer laterally on the basis of a neural network model for category semantic perception. The features extracted by a superficial-layer neural network of a deep neural network (such as the neural network model for category semantic perception) is easy to understand, and may be taken as a fuzzy edge or a region feature. The deeper a network layer is, the more abstract features may be extracted. Simply increasing network layers vertically may result in a more abstract feature. In some embodiments, network layers for extracting features may be added laterally to learn both superficial features and deep features. The superficial features and deep features may be merged to improve an effect of detecting the target metal region in the X-ray image.

In some embodiments, the first count of the at least one up-sampling layer 1621 may equal to the second count of the plurality of residual blocks 1614. In some embodiments, a third count of the at least one transposed convolution 1622 of an up-sampling layer 1621 corresponding to a deeper residual block may be greater than or equal to a fourth count of the at least one transposed convolution 1622 of an up-sampling layer 1621 corresponding to corresponding to a superficial residual block. The image features outputted by vertical network layers may be abstract. The deeper the network layer is, the more abstract the image features may be. The feature fusion structure 1630 may be used to extract edge feature information from the image features. The more abstract a feature is, the more likely the edge information may be lost. A lateral network layer (i.e., an up-sampling layer) for extracting features may be added to each residual block, to better restore the edge features in each first initial feature and improve a retention rate of edge information of the first initial feature outputted by the residual block. In some embodiments, an information loss due to a small count of up-sampling layers may be avoided. In addition, the image features outputted by the vertical network layers may have a reduced image dimension. The deeper the network layer is, the smaller the image dimension may be. The deeper of the residual block, the smaller the dimension of the first initial feature may be. However, the feature fusion structure 1630 may require that the edge feature information is restored to the same size as the original X-ray image. The feature with a smaller dimension may need to be gradually restored to a size of the initial X-ray image, to avoid losing information due to a one-time restoration to the size of the initial X-ray image. A deeper up-sampling layer 1621 may need more transposed convolutions 1622, thereby further improving the retention rate of edge information of the first initial feature.

In some embodiments, the initial feature extraction structure 1610 may include three residual blocks 1614: a superficial-layer residual block 1614, an interlayer residual block 1614, and a deep-layer residual block 1614. The fusion feature extraction structure 1620 may include three up-sampling layers 1621. A first up-sampling layer 1621 corresponding to the superficial-layer residual block 1614 may include one transposed convolution 1622. A second up-sampling layer 1621 corresponding to the interlayer residual block 1614 may include two transposed convolutions 1622. A third up-sampling layer 1621 corresponding to the deep-layer residual block 1614 may include four transposed convolutions 1622.

In some embodiments, in order to further improve the comprehensiveness and accuracy of the fusion feature, the initial feature extraction structure 1610 may include three residual blocks 1614, the fusion feature extraction structure 1620 may include three up-sampling layers 1621, the first up-sampling layer corresponding to the superficial-layer residual block (i.e., residual block 1) may only include one transposed convolution 1622, the second up-sampling layer corresponding to the interlayer layer residual block (i.e., residual block 2) may include two transposed convolutions 1622, and the third up-sampling layer corresponding to the deep-layer residual block (i.e., residual block 3) may include four transposed convolutions 1622.

FIG. 17 is a flowchart illustrating an exemplary process 1700 for obtaining a trained metal detection model according to some embodiments of the present disclosure. The process 1700 may be executed by the imaging system 100. For example, the process 1700 may be implemented as a set of instructions (e.g., an application) stored in the storage ROM 230 or RAM 240. The processor 220 may execute the set of instructions, and when executing the instructions, it may be configured to perform the process 1700. The operations of the illustrated process presented below are intended to be illustrative. In some embodiments, the process 1700 may be accomplished with one or more additional operations not described and/or without one or more of the operations discussed. Additionally, the order in which the operations of the process as illustrated in FIG. 17 and described below is not intended to be limiting.

In 1710, the processing device 120 (e.g., the processor 220, the model training module 430) may obtain a sample set. The sample set may include a plurality of sample pairs. In some embodiments, each sample pair of the plurality of sample pairs may include a sample X-ray image and a reference binary image indicating a reference metal region with respect to the X-ray image. In some embodiments, the reference metal region may include a complete edge.

In some embodiments, the plurality of sample pairs may be in a form of image pairs. FIG. 18 illustrates exemplary sample X-ray images 1810 and exemplary labeled metal images 1820 with respect to each of the sample X-ray images according to some embodiments of the present disclosure. As shown in FIG. 18, each sample X-ray image 1810 (in which a dark region is a metal region) may correspond to a labeled metal image 1820 (in which a white edge is a metal region edge). Each labeled metal image 1820 may be generated based on its corresponding sample X-ray image 1810 by performing a metal region identification, a metal edge delineation, a binarization, or the like, or any combination thereof. An edge of a reference metal region may be complete, which may be used as a ground truth of the sample set to determine an error and an error backpropagation of an output of a model output during training the model. For example, a plurality of DICOM images may be obtained from clinical scans, and the reference binary image corresponding to each DICOM image may be generated. Since in the initial binary image outputted by the trained metal detection model, only the edge of the metal region is marked. The edge of the reference metal region may be distinguished from image content other than the edge in the reference binary image.

In 1720, the processing device 120 (e.g., the processor 220, the model training module 430) may obtain the trained metal detection model by training a preliminary metal detection model based on the sample set.

In some embodiments, the preliminary metal detection model may include model that has a same structure as that of the improved neural network model for category semantic perception as described in FIG. 16. In some embodiments, model parameters of the preliminary metal detection model may include initial model parameters of the improved neural network model for category semantic perception. The initial model parameter may include a random number based on a zero mean and a predetermined variance (e.g., a small variance, such as 0.01). The model training process may be a process for iteratively updating the model parameters. In some embodiments, a loss function of the preliminary metal detection model may include a multi-category comparison loss function of the improved neural network model for category semantic perception. In some embodiments, the loss function may be used to determine an error between an output of the trained metal detection model and the corresponding reference binary image. In some embodiments, the loss function may be used to determine an error backpropagation method, thereby driving an iterative training process.

In some embodiments, the plurality of sample pairs of the sample set may be sequentially inputted into the preliminary metal detection model for model training until a termination condition is satisfied. For example, if a difference between the output of a training model and the reference binary image satisfies a predetermined difference requirement, updated model parameters of the training model may be obtained. In some embodiments, the updated model parameters of the training model may be used to replace the initial model parameters of the preliminary metal detection model to obtain the trained metal detection model.

In some embodiments, a preliminary metal detection model may be constructed based on an improved neural network model for category semantic perception, the initial model parameters, and the multi-class comparison loss function. The trained metal detection model may be generated by inputting each sample pair of the sample set into the preliminary metal detection model for model training. The trained metal detection model may be used to extract metal regions from the X-ray.

Figure 19:
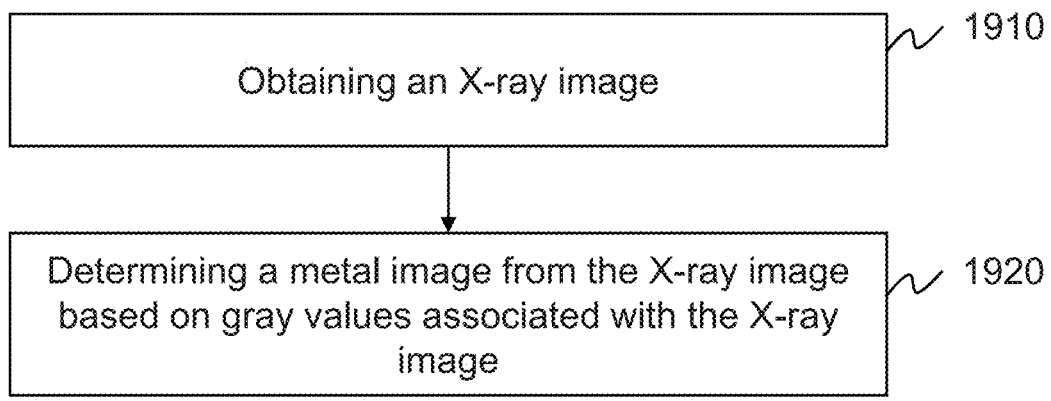
FIG. 19 is a flowchart illustrating an exemplary process for determining a metal image according to some embodiments of the present disclosure.

FIG. 19 is a flowchart illustrating an exemplary process 1900 for determining a metal image according to some embodiments of the present disclosure. The process 1900 may be executed by the imaging system 100. For example, the process 1900 may be implemented as a set of instructions (e.g., an application) stored in the storage ROM 230 or RAM 240. The processor 220 may execute the set of instructions, and when executing the instructions, it may be configured to perform the process 1900. The operations of the illustrated process presented below are intended to be illustrative. In some embodiments, the process 1900 may be accomplished with one or more additional operations not described and/or without one or more of the operations discussed. Additionally, the order in which the operations of the process as illustrated in FIG. 19 and described below is not intended to be limiting.

In 1910, the processing device 120 (e.g., the processor 220, the image obtaining module 410) may obtain an X-ray image.

In some embodiments, the X-ray image may include an image of a target object. The target object may include a human body, a tissue, an organ of the human body, an animal, a plant, a non-living organism, or the like, or any combination thereof. In some embodiments, the X-ray image may be generated by an X-ray imaging technology. In some embodiments, the processing device 120 may obtain the X-ray image from the medical device 110 (e.g., an X-ray machine, an electronic computer tomography (CT) device, a C-arm X-ray machine, a DSA device, a B-mode ultrasound machine, etc.). In some embodiments, the processing device 120 may obtain the X-ray image stored in the storage 130.

In some embodiments, the X-ray image may include or not include information of a metal object. In some embodiments, gray values of the metal object and the target object may be different, due to different attenuations of rays of the object and the target object. In some embodiments, the X-ray image obtained by the medical device 110 (e.g., an X-ray machine, an electronic computer tomography (CT) device, a C-arm X-ray machine, a DSA device, a B-mode ultrasound machine, etc.) may be preprocessed to obtain. For example, if the X-ray image is a CT image, since the X-ray decays exponentially, the processing device 120 may perform a logarithmic transformation (e.g., a log transformation) on the X-ray image. A contrast of the X-ray image and the X-ray attenuation may have a linear relation, and a contrast in a low grayscale range of the X-ray image may be increased. As another example, the X-ray image may be normalized to make that the grayscale range of the X-ray image is within a same grayscale range (e.g., 0-1). In this way, the X-ray image may be processed based on a same threshold. The preprocessed X-ray image may be updated.

In 1920, the processing device 120 (e.g., the processor 220, the metal image determining module 420) may determine a metal image from the X-ray image based on gray values associated with the X-ray image In some embodiments, the processing device 120 may determine a metal edge region based on gray values of pixels in the X-ray image. The processing device 120 may determine a difference set between the metal edge region and a target edge region of a region of interest (ROI), and determine a seed point from the difference set. In some embodiments, the processing device 120 may generate the metal image by performing a region growth based on the seed point. In some embodiments, the processing device 120 may determine a strong gradient image of the X-ray image and an average gray value of pixels at gradient positions corresponding to the strong gradient image. The processing device 120 may determine whether the X-ray image includes the metal image based on the average gray value of pixels at gradient positions and a gray value with respect to a peak of a gray value of the X-ray image. Exemplary processes for determining the metal image based on the gray values associated with the X-ray image may be found elsewhere (e.g., FIG. 21 or FIG. 25 and the descriptions thereof) in the present disclosure.

Figure 20:
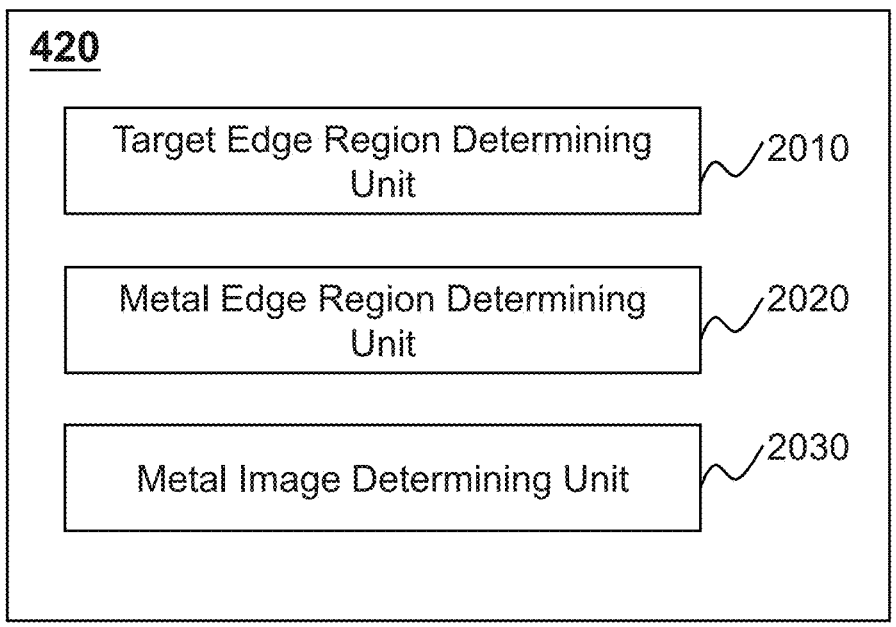
FIG. 20 is a block diagram illustrating an exemplary metal image determining module according to some embodiments of the present disclosure.

FIG. 20 is a block diagram illustrating an exemplary metal image determining module 420 according to some embodiments of the present disclosure. As illustrated in FIG. 20, the metal image determining module 420 may include a target edge region determining unit 2010, a metal edge region determining unit 2020, and a metal image determining unit 2030.

The target edge region determining unit 2010 may be configured to determine a target edge region of at least one region of interest (ROI) in the X-ray image. In some embodiments, the target edge region may include a metal edge or an object edge.

The metal edge region determining unit 2020 may be configured to determine a metal edge region. For example, the metal edge region determining unit 2020 may obtain a target neighborhood of each pixel in the X-ray image. The metal edge region determining unit 2020 may determine the metal edge region based on gray values of pixels in each of a plurality of target neighborhoods corresponding to the plurality of pixels in the X-ray image.

The metal image determining unit 2030 may be configured to determine the metal image. For example, the metal image determining unit 2030 may determine a difference set between the metal edge region and the target edge region. The metal image determining unit 2030 may determine a seed point from the first difference set and perform a region growth based on the seed point to obtain the metal image.

The units in the metal image determining module 420 may be connected to or communicate with each other via a wired connection or a wireless connection. The wired connection may be a metal cable, an optical cable, a hybrid cable, or the like, or any combination thereof. The wireless connection may be a Local Area Network (LAN), a Wide Area Network (WAN), a Bluetooth, a ZigBee, a Near Field Communication (NFC), or the like, or any combination thereof. Two or more of the units may be combined into a single module, and any one of the units may be divided into two or more units.

Figure 21:
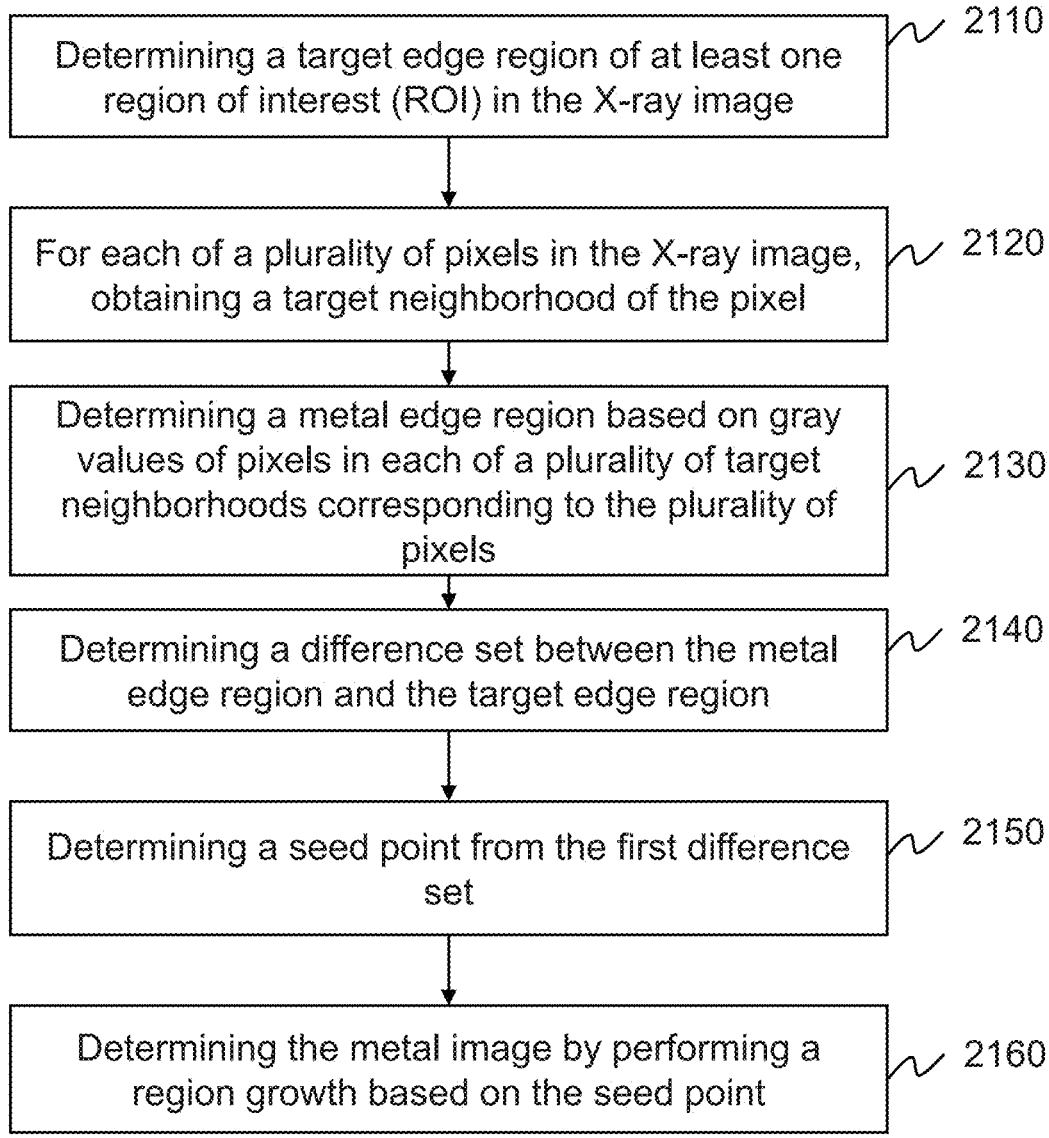
FIG. 21 is a flowchart illustrating an exemplary process for determining a metal image according to some embodiments of the present disclosure.

FIG. 21 is a flowchart illustrating an exemplary process 2100 for determining a metal image according to some embodiments of the present disclosure. The process 2100 may be executed by the imaging system 100. For example, the process 2100 may be implemented as a set of instructions (e.g., an application) stored in the storage ROM 230 or RAM 240. The processor 220 may execute the set of instructions, and when executing the instructions, it may be configured to perform the process 2100. The operations of the illustrated process presented below are intended to be illustrative. In some embodiments, the process 2100 may be accomplished with one or more additional operations not described and/or without one or more of the operations discussed. Additionally, the order in which the operations of the process as illustrated in FIG. 21 and described below is not intended to be limiting.

In 2110, the processing device 120 (e.g., the processor 220, the metal image determining module 420, the target edge region determining unit 2010) may determine a target edge region of at least one region of interest (ROI) in the X-ray image.

In some embodiments, the target edge region may include a metal edge or an object edge. For example, the processing device 120 may extract the target edge region of the at least one ROI in the X-ray image using an edge operator. In some embodiments, the edge operator may include a Roberts operator, a Sobel operator, a Prewitt operator, a Laplacian operator, a Canny operator, or the like, or any combination thereof. In some embodiments, the target edge region may be a rectangular region of M*N, wherein M and N are both positive integers. For example, the target edge region may be a 3*3 rectangular region.

In 2120, for each of a plurality of pixels in the X-ray image, the processing device 120 (e.g., the processor 220, the metal image determining module 420, the metal edge region determining unit 2020) may obtain a target neighborhood of the pixel.

In the X-ray image, there may be a difference between a gray value of the metal object and a gray value of the target object (e.g., the human body). In some embodiments, the difference may cause an obvious gradient change between a metal edge of the metal object and a target edge of the target object. In this way, whether the X-ray image includes information of a metal object may be determined. In some embodiments, the processing device 120 may obtain the target neighborhood of each pixel in the X-ray image. In some embodiments, the target neighborhood may be a rectangular region. In some embodiments, the target edge region may be a thin rectangular region, and the target neighborhood may be a thick rectangular region. For example, if the target edge region is a 3*3 rectangular region, the target neighborhood may be a rectangular region no smaller than 5*5.

In 2130, the processing device 120 (e.g., the processor 220, the metal image determining module 420, the metal edge region determining unit 2020) may determine a metal edge region based on gray values of pixels in each of a plurality of target neighborhoods corresponding to the plurality of pixels.

In some embodiments, the processing device 120 may determine the metal edge region based on a gray value of each pixel in the target neighborhood. For example, the metal edge region may be selected from the target neighborhood based on a grayscale variance value of pixels in the target neighborhood. In some embodiments, the metal edge and/or the target edge may have a great gradient change, and the grayscale variance value of pixels in the target neighborhood located at the metal edge and/or the target edge may be greater than that of pixels located elsewhere. In some embodiments, the processing device 120 may designate a target neighborhood that satisfies a predetermined grayscale variance threshold as the metal edge region. In some embodiments, the metal edge region may include a region with low gray values and a region with high gray values. The region with low gray values may indicate the metal object.

In some embodiments, the processing device 120 may determine one or more metal edge regions. For example, if there are more than one target neighborhoods that satisfy the predetermined grayscale variance threshold, the processing device 120 may integrate the more than one target neighborhoods to obtain the metal edge region. In some embodiments, the metal edge region may be continuous or discontinuous.

In 2140, the processing device 120 (e.g., the processor 220, the metal image determining module 420, the metal image determining unit 2030) may determine a difference set between the metal edge region and the target edge region.

In some embodiments, pixels in the difference set may belong to the metal edge region and not belong to the target edge region. The pixels in the difference sets may be located at the metal edge or the object edge.

In 2150, the processing device 120 (e.g., the processor 220, the metal image determining module 420, the metal image determining unit 2030) may determine a seed point from the first difference set.

In some embodiments, the processing device 120 may extract the seed point from the difference set. For example, since the gray values of the metal object in the X-ray image is less than the gray values of the target object, if a pixel with a minimum gray value in the difference set is designated as the seed point, the seed point must be a pixel of the metal image.

In 2160, the processing device 120 (e.g., the processor 220, the metal image determining module 420, the metal image determining unit 2030) may determine the metal image by performing a region growth based on the seed point.

In some embodiments, the processing device 120 may perform a region growth on the seed point. In some embodiments, the processing device 120 may obtain a current growth result and an access region based on accessed pixels during the region growth. The processing device 120 may determine an updated target edge region based on a difference set between the target edge region and the access region. The processing device 120 may determine an updated metal edge region based on a difference set between the metal edge region and the access region. In some embodiments, the processing device 120 may repeat steps of determining the difference set between the metal edge region and the access region until the updated target edge region satisfies a first condition or the updated metal edge region satisfies a second condition. If the updated target edge region satisfies the first condition or the updated metal edge region satisfies the second condition, the processing device 120 may designate the current growth result as the metal image.

In some embodiments, if there are several metal objects in the X-ray image and several metal objects are discontinuous, only parts of the several metal objects may be detected by performing the region growth based on the seed point. Therefore, the processing device 120 may process the X-ray image several times to ensure that each metal object of the several metal objects in the X-ray image is detected. For example, the processing device 120 may perform the region growth on the seed point to generate the current growth result. The current growth result may be a part (or parts) of the several metal objects in the X-ray image. During the region growth, an access region may be determined based on the accessed pixels. In some embodiments, to improve detection efficiency, pixels in an access region may be not accessed again during the region growth. Therefore, the processing device 120 may extract the access region separately. In some embodiments, the target edge region may be updated based on the difference set between the target edge region and the access region, and the metal edge region may be updated based on the difference between the metal edge region and the access region. In some embodiments, the processing device 120 may remove the target edge region and the metal edge region from the access region. In some embodiments, the processing device 120 may repeat determining the difference set between the metal edge region and the target edge region until the target edge region satisfies the first condition or the metal edge region satisfies the second condition. In some embodiments, the first condition may include that the target edge region is empty. In some embodiments, the second condition may include that the metal edge region is empty. The processing device 120 may designate the current growth result of each current region as the metal image.

In some embodiments, the processing device 120 may obtain a current growth result. The processing device 120 may determine a first average gray value of first pixels in the current growth result and an adaptive threshold of the metal edge region. The processing device 120 may determine a second average gray value of second pixels with gray values less than the adaptive threshold in the metal edge region. The processing device 120 may determine whether the current growth result is the metal image based on the first average gray value and the second average gray value.

In some embodiments, the processing device 120 may determine that the metal edge region includes a region with lower gray values and a region with higher gray values based on the gray value of each pixel in the target neighborhood of each pixel in the X-ray image. The region with lower gray values may be the target object, and the region with higher gray values may be air, since air has a minimum attenuation of X-rays. In is possible to mistake the target object as the metal object. Therefore, the processing device 120 may further determine whether the metal edge region is a real metal object.

In some embodiments, when the gray values of the metal object are less than the gray values of the target object, the processing device 120 may generate a current growth result by performing the region growth based on the seed point. A first average gray value of first pixels in the current growth result may be determined. The first average gray value may be a grayscale feature of each pixel that is determined as a metal object. Taking a metal edge region in the X-ray image as an example, the adaptive threshold of the metal edge region may be determined using a great law segmentation algorithm. The processing device 120 may further determine a second average gray value of second pixels with gray values less than the adaptive threshold in the metal edge region. If the metal edge region includes the metal object, the second average gray value may be a grayscale feature of the pixels of the metal object. The second average gray value may be similar to the first average gray value. Otherwise, the second average gray value may be a grayscale feature of the pixels of the target object. A difference between the second average gray value and the first average gray value may be great. In some embodiments, the processing device 120 may determine whether the current growth result is the metal image based on a numerical relation between the first gray average and the second gray average. For example, if the difference between the second gray average and the first gray average is greater than a predetermined threshold, the metal edge region may not include the metal object. Otherwise, the metal edge region may include the metal. In this way, the processing device 120 may further determine whether each metal edge region actually includes the metal object.

Figure 22:
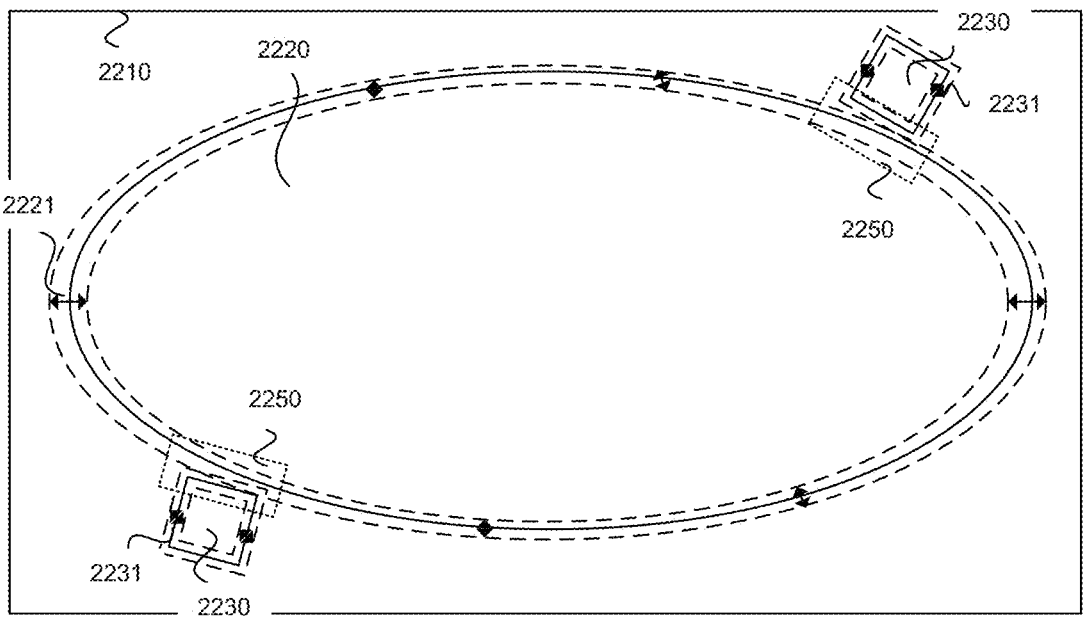
FIG. 22 illustrates an exemplary X-ray image according to some embodiments of the present disclosure.

FIG. 22 illustrates an exemplary X-ray image according to some embodiments of the present disclosure. As shown in FIG. 22, the X-ray image 2210 may include a target object 2220 and metal objects 2230. The target object 2220 may be represented by a solid line. The target edge region may be a target edge 2221 or a metal edge 2231. The metal edge region 2250 may include a region with lower gray values and a region with higher gray values. The target edge region 2220 and the metal edge region 2250 may be represented by broken lines. The metal edge region 2250 may be a thick rectangular region, and the target edge region may be a thin rectangular region.

In some embodiments, the medical device 110 may capture a plurality of X-ray images during each examination. After the processing device 120 obtains a first X-ray image, a metal image in the first X-ray image may be determined. In some embodiments, in an early stage for obtaining the subsequent X-ray images (e.g., a second X-ray image and a third X-ray image obtained after the first X-ray image), a radiation dose may be adjusted based on gray values of a region other than the metal object in the first X-ray image, thereby solving a problem that the gray values of the metal object is low. To make an overall gray value of the X-ray image (e.g., the second X-ray image or the third X-ray image) meet an acquisition target, a higher radiation dose may need to be added to the medical device 110, which causes the target object (e.g., the human body) to receive a lot of additional radiations. In some embodiments, in a later stage for processing the subsequent X-ray images (e.g., a second X-ray image and a third X-ray image obtained after the first X-ray image), the gray values of the entire X-ray image (e.g., the second X-ray image or the third X-ray image) may be adjusted based on the gray values of the region other than the metal object in the X-ray image, thereby solving a problem that the metal object occupies a part of a grayscale range that is used to display the target object. A low grayscale contrast of the target object may be improved and an image quality may be improved.

Figure 23:
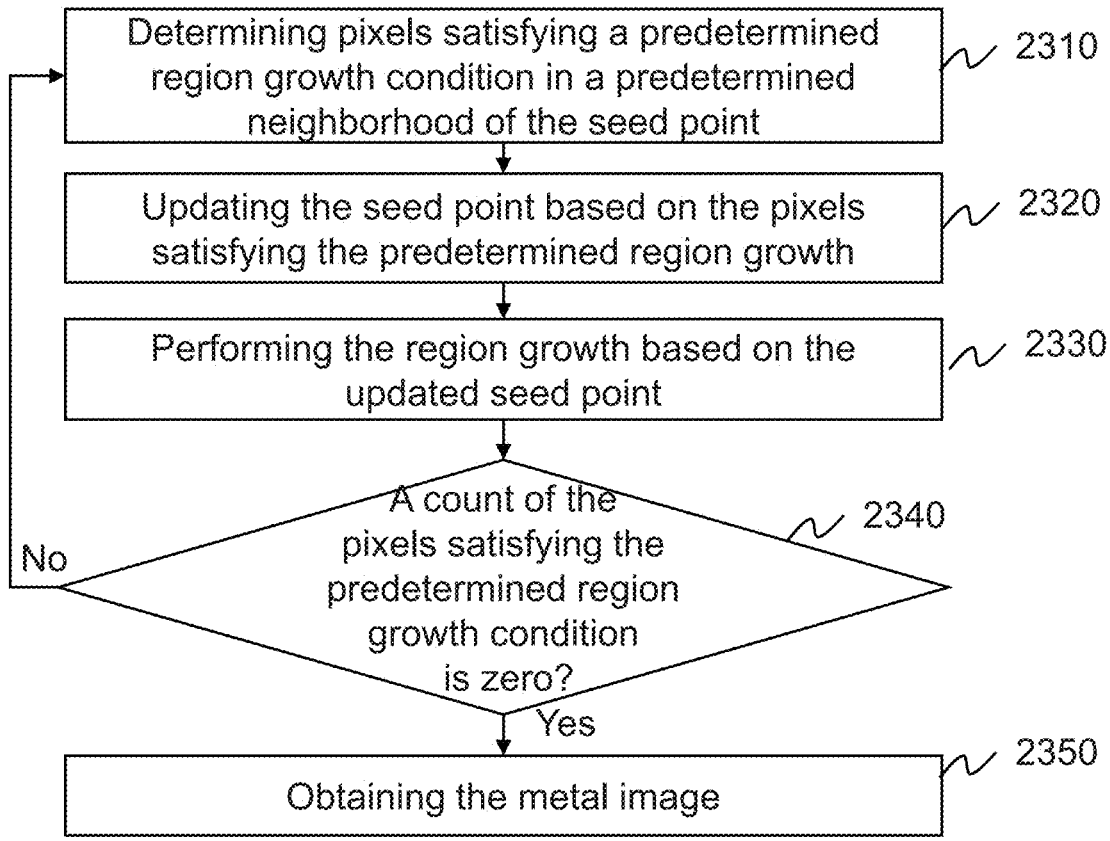
FIG. 23 is a flowchart illustrating an exemplary process for determining a metal image according to some embodiments of the present disclosure.

FIG. 23 is a flowchart illustrating an exemplary process 2300 for determining a metal image according to some embodiments of the present disclosure. The process 2300 may be executed by the imaging system 100. For example, the process 2300 may be implemented as a set of instructions (e.g., an application) stored in the storage ROM 230 or RAM 240. The processor 220 may execute the set of instructions, and when executing the instructions, it may be configured to perform the process 2300. The operations of the illustrated process presented below are intended to be illustrative. In some embodiments, the process 2300 may be accomplished with one or more additional operations not described and/or without one or more of the operations discussed. Additionally, the order in which the operations of the process as illustrated in FIG. 23 and described below is not intended to be limiting.

In 2310, the processing device 120 (e.g., the processor 220, the metal image determining module 420, the metal image determining unit 2030) may determine pixels satisfying a predetermined region growth condition in a predetermined neighborhood of the seed point.

In 2320, the processing device 120 (e.g., the processor 220, the metal image determining module 420, the metal image determining unit 2030) may update the seed point based on the pixels satisfying the predetermined region growth.

In 2330, the processing device 120 (e.g., the processor 220, the metal image determining module 420, the metal image determining unit 2030) may perform the region growth based on the updated seed point.

In 2340, the processing device 120 (e.g., the processor 220, the metal image determining module 420, the metal image determining unit 2030) may determine whether a count of the pixels satisfying the predetermined region growth condition is zero.

In 2350, in response to a determination that the count of the pixels satisfying the predetermined region growth condition is zero, the processing device 120 (e.g., the processor 220, the metal image determining module 420, the metal image determining unit 2030) may obtain the metal image.

In response to a determination that the count of the pixels satisfying the predetermined region growth condition is not zero, the processing device 120 may repeat operations 2310-2340 until the count of the pixels satisfying the predetermined region growth condition is zero.

In some embodiments, the processing device 120 may obtain the pixels in the predetermined neighborhood (e.g., a 4-neighborhood or an 8-neighborhood) of the seed point that satisfies the predetermined region growth condition. The pixels that satisfy the predetermined region growth condition may be used as a new seed point to continue the region growth until the pixels that satisfy the predetermined region growth condition is empty (i.e., a count of pixels that satisfy the predetermined region growth condition is zero), the region growth may end. Since there may be several seed points at the same time, the region growth based on the seed points may be performed at the same time, thereby improving the detection efficiency. During the region growth, all the pixels that are used as the seed points may belong to the metal object to determine the metal image.

In some embodiments, the processing device 120 may determine pixels in the predetermined neighborhood of the seed point as neighbor points. The processing device 120 may determine a structural similarity between the neighbor points and the seed point. The processing device 120 may determine an intersection set between the neighbor points and the target edge region and a grayscale similarity between the neighbor points and the seed point. The processing device 120 may select pixels satisfying the predetermined region growth condition from the neighbor points as the pixels satisfying the predetermined region growth condition.

In some embodiments, the processing device 120 may perform a predetermined non-parametric image transformation (e.g., a Census transformation) on the X-ray image to obtain transformation points of the neighborhood points. In some embodiments, a structural similarity (e.g., a structural similarity of the Hamming distance) between transformation points and the seed point may be less than the first threshold. The seed point may be untransformed. In some embodiments, the processing device 120 may determine the structural similarity based on a histogram of the neighbor points and the seed point. In some embodiments, the intersection set of the neighbor points and the target edge region may be empty. The neighbor points may be not at the target edge region, since the neighborhood points being at the target edge region is a condition for terminating the region growth. In some embodiments, a grayscale similarity of an average gray value of the neighborhood points and each seed point may be less than a second threshold. A difference between the gray values of the neighborhood points and the gray values of pixels that have been determined as the metal object may be small. If a pixel satisfies the predetermined region growth condition, the pixel may satisfy at least one of the above conditions. On this basis, the pixel may be not an access pixel. Each pixel may only be determined once, so that the region growth may end.

Figure 24:
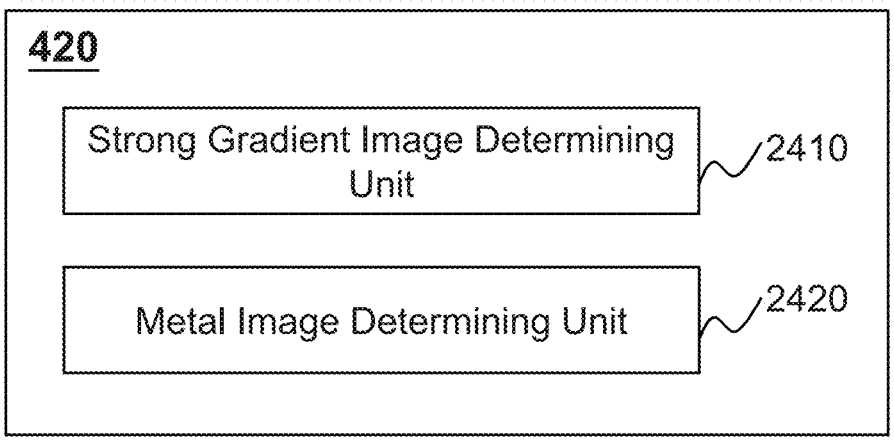
FIG. 24 is a block diagram illustrating an exemplary metal image determining module according to some embodiments of the present disclosure.

FIG. 24 is a block diagram illustrating an exemplary metal image determining module 420 according to some embodiments of the present disclosure. As illustrated in FIG. 24, the metal image determining module 420 may include a strong gradient image determining unit 2410 and a metal image determining unit 2420.

The strong gradient image determining unit 2410 may be configured to determine a strong gradient image of the X-ray image. In some embodiments, the strong gradient image determining unit 2410 may obtain a gradient feature of the X-ray image. The strong gradient image determining unit 2410 may determine the strong gradient image based on the gradient feature of the X-ray image.

The metal image determining unit 2420 may be configured to determine the metal image based on the X-ray image. In some embodiments, the metal image determining unit 2420 may determine whether the X-ray image includes metal information based on the strong gradient image.

Figure 25:
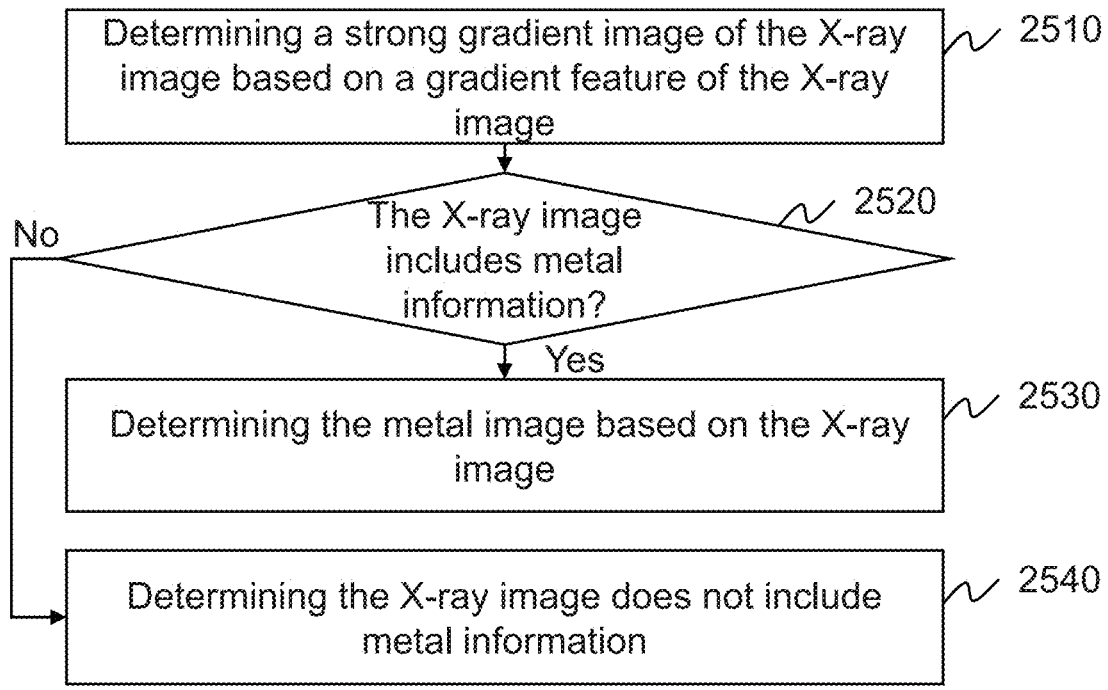
FIG. 25 is a flowchart illustrating an exemplary process for determining a metal image according to some embodiments of the present disclosure.

FIG. 25 is a flowchart illustrating an exemplary process 2500 for determining a metal image according to some embodiments of the present disclosure. The process 2500 may be executed by the imaging system 100. For example, the process 2500 may be implemented as a set of instructions (e.g., an application) stored in the storage ROM 230 or RAM

240. The processor 220 may execute the set of instructions, and when executing the instructions, it may be configured to perform the process 2500. The operations of the illustrated process presented below are intended to be illustrative. In some embodiments, the process 2500 may be accomplished with one or more additional operations not described and/or without one or more of the operations discussed. Additionally, the order in which the operations of the process as illustrated in FIG. 25 and described below is not intended to be limiting.

In 2510, the processing device 120 (e.g., the processor 220, the metal image determining module 420, the strong gradient image determining unit 2410) may determine a strong gradient image of the X-ray image based on a gradient feature of the X-ray image.

In some embodiments, the processing device 120 may obtain the gradient feature by taking the X-ray image as a two-dimensional discrete function, and taking a derivative of the two-dimensional discrete function. In some embodiments, an edge of the X-ray image may be determined by performing a gradient operation on the X-ray image. In some embodiments, the gradient feature of the X-ray image may be a vector having a size and a direction. In some embodiments, the processing device 120 may extract boundary points of the X-ray image obtain a boundary gradient image. The processing device 120 may remove scattered points and small boundary points from the boundary gradient image to obtain the strong gradient image corresponding to the X-ray image.

In 2520, the processing device 120 (e.g., the processor 220, the metal image determining module 420, the metal image determining unit 2420) may determine whether the X-ray image includes metal information based on the strong gradient image.

In some embodiments, the metal information may be displayed as a metal region. The metal region refers to a region that may affect a radiation dose or an image display effect when the medical device 110 scans the target object. The metal region may include metal information of a plurality of metal objects (e.g., various metal surgical instruments).

In some embodiments, if the metal region is large during a conventional scan on the target object, the radiation dose may be adjusted based on gray values in the X-ray image. For example, if there is a large metal region in the X-ray image, due to a high X-ray attenuation of the metal object, an imaging location may be determined too thick by mistake to increase the radiation dose. If the target object is a human body, the human body may receive much radiation. In some embodiments, if the large metal region is not removed when the X-ray image is processed, the large metal region may be processed together with the target object, which may cause that a grayscale range supposed to display the target object is occupied by the large metal region. The contrast of the target object may be reduced. In some embodiments, if the metal region is small, an effect of the conventional scan on the target object may be ignored.

In some embodiments, the processing device 120 may determine an average gray value of pixels at gradient positions corresponding to the strong gradient image based on the X-ray image. The processing device 120 may determine a peak in a grayscale histogram of the X-ray image and a gray value corresponding to the peak. The processing device 120 may determine whether there is a metal region in the X-ray image based on the average gray value and the gray value corresponding to the peak. In some embodiments, the processing device 120 may determine whether the X-ray image includes a metal region based on the X-ray image and the strong gradient image corresponding to the X-ray image to avoid an effect of the metal region on the radiation dose or a final image display effect of the X-ray image.

In 2530, in response to a determination that the X-ray image includes the metal information, the processing device 120 (e.g., the processor 220, the metal image determining module 420, the metal image determining unit 2420) may determine the metal image based on the X-ray image.

In some embodiments, if the X-ray image includes a metal region, the processing device 120 may segment the X-ray image according to a predetermined image size to generate at least one segmented image. The processing device 120 may determine an average gray value and a variance of the at least one segmented image. A current segmented image may be determined as the metal region in the X-ray image, only when the current segmented image and all segmented images adjacent to the current segmented image satisfy a same condition. In this way, the metal region may be accurate, thus achieving a good image segmentation effect. The image display effect may be improved.

In 2540, in response to a determination that the X-ray image does not include the metal information, the processing device 120 (e.g., the processor 220, the metal image determining module 420, the metal image determining unit 2420) may determine that the X-ray image does not include metal information.

Figure 26:
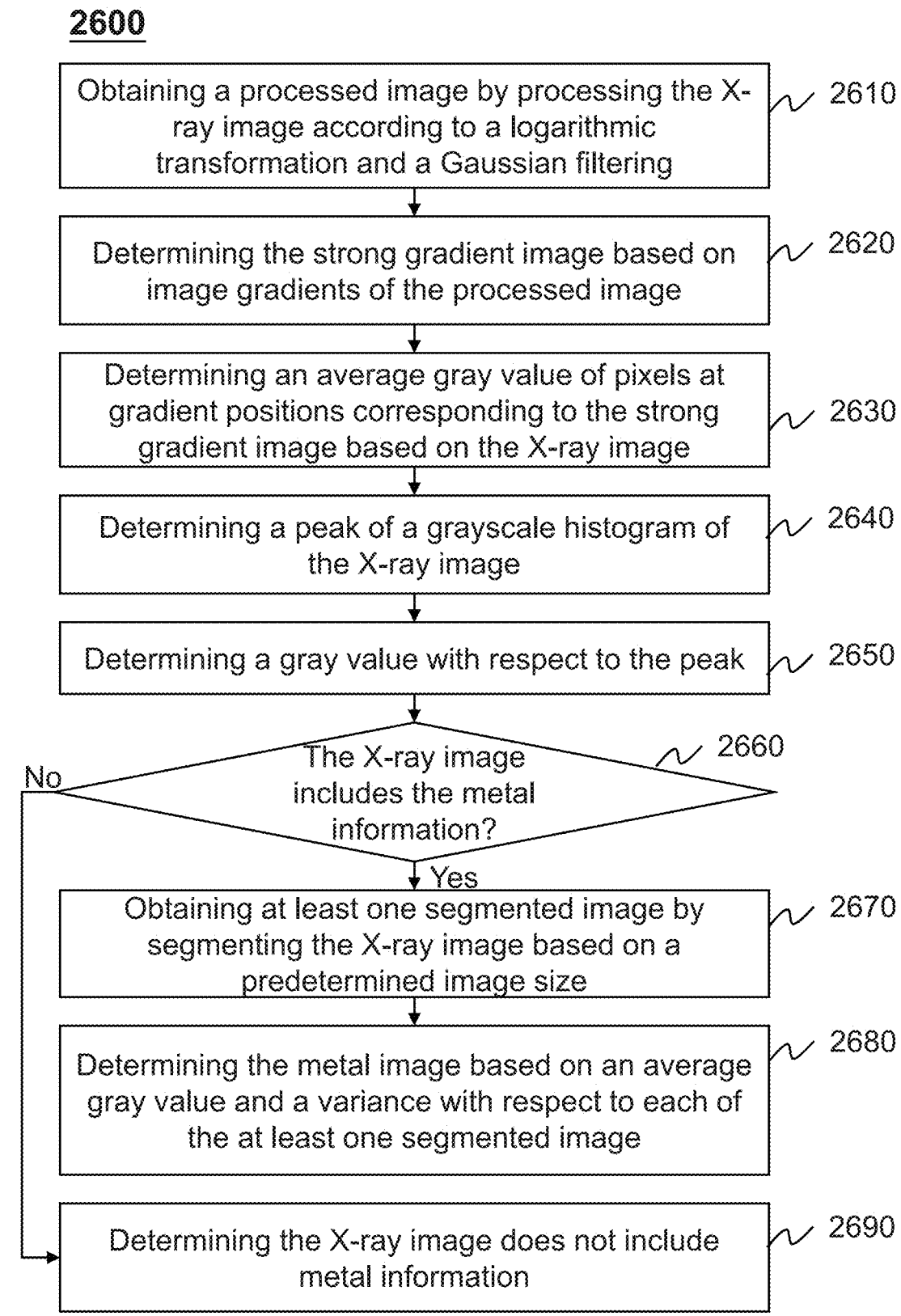
FIG. 26 is a flowchart illustrating an exemplary process for determining a metal image according to some embodiments of the present disclosure.

FIG. 26 is a flowchart illustrating an exemplary process 2600 for determining a metal image according to some embodiments of the present disclosure. The process 2600 may be executed by the imaging system 100. For example, the process 2600 may be implemented as a set of instructions (e.g., an application) stored in the storage ROM 230 or RAM 240. The processor 220 may execute the set of instructions, and when executing the instructions, it may be configured to perform the process 2600. The operations of the illustrated process presented below are intended to be illustrative. In some embodiments, the process 2600 may be accomplished with one or more additional operations not described and/or without one or more of the operations discussed. Additionally, the order in which the operations of the process as illustrated in FIG. 26 and described below is not intended to be limiting.

In 2610, the processing device 120 (e.g., the processor 220, the metal image determining module 420, the strong gradient image determining unit 2410) may obtain a processed image by processing the X-ray image according to a logarithmic transformation and a Gaussian filtering.

In some embodiments, the logarithmic transformation may be used to expand low gray values of the X-ray image and compress high gray values of the X-ray image. A grayscale distribution of the entire X-ray image may be in line with human visual characteristics. In some embodiments, the Gaussian filtering may be a linear smoothing filtering after determining a weight based on a shape of the Gaussian function, which is very effective for suppressing noises that obeying a normal distribution. By performing the Gaussian filtering on the X-ray image, a two-dimensional convolution operator using Gaussian kernel may be used to blur the X-ray image. Details and noises in the X-ray image may be removed.

In some embodiments, the processing device 120 may perform the logarithmic transformation on the X-ray image to balance the grayscale distribution of the X-ray image. The processing device 120 may perform the Gaussian filtering on the logarithmically transformed image. The logarithmically transformed image may be smooth filtered. A smooth degree of the filtered image may depend on a standard deviation thereof. Since an output of the Gaussian filtering is a weighted average of pixels in the X-ray image, a pixel closer to the center pixel of the X-ray image may have a higher weight. Therefore, compared to an average filter, a Gaussian filter may output an image with a softer smoothing effect and an edge of the X-ray image may be better preserved.

In 2620, the processing device 120 (e.g., the processor 220, the metal image determining module 420, the strong gradient image determining unit 2410) may determine the strong gradient image based on image gradients of the processed image.

In some embodiments, the processing device 120 may determine the image gradients of the X-ray image by performing a gradient algorithm on the processed image to generate a boundary gradient image. The processing device 120 may determine the strong gradient image based on an area of a connected region of boundary points in the boundary gradient image.

Figure 27:
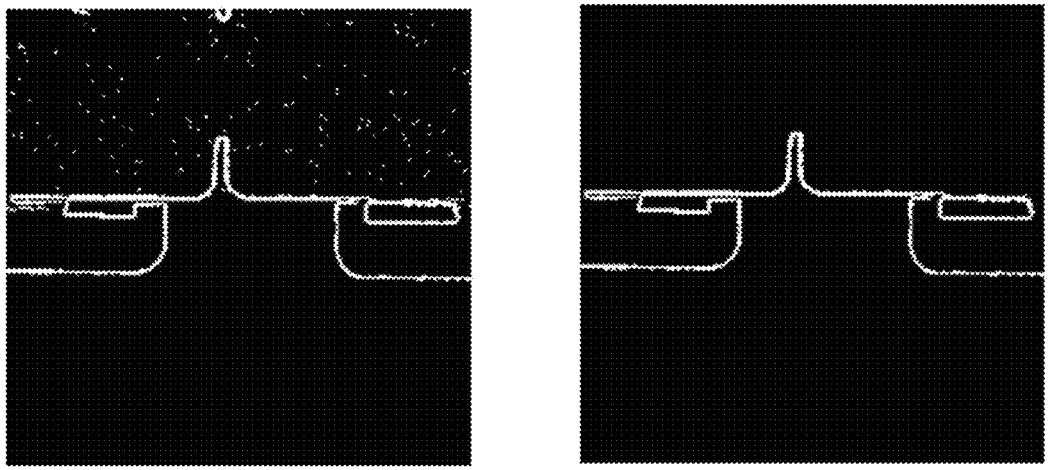
FIG. 27 illustrates an exemplary boundary gradient image and an exemplary strong gradient image according to some embodiments of the present disclosure.

In some embodiments, the gradient algorithm may include conventional operators operate on a grayscale image of the X-ray image. FIG. 27 illustrates an exemplary boundary gradient image and an exemplary strong gradient image according to some embodiments of the present disclosure. In some embodiments, the processing device 120 may determine the image gradients of the X-ray image using a Sobel operator. The processing device 120 may designate a point having an image gradient greater than a predetermined gradient threshold as a boundary point. The processing device 120 may set the boundary point as 1 and a point in other regions as 0, thereby generating a boundary gradient image. A left diagram of FIG. 27 is an exemplary boundary gradient image. The Sobel operator may be used for an edge detection. The Sobel operator may be a discrete difference operator, which is used to determine an approximate gray value of an image brightness function. A grayscale vector or a normal vector corresponding to any point in the X-ray image may be generated by applying the Sobel operator to the point. The Sobel operator may determine an edge according to a weighted grey difference between upper, lower, left and right points adjacent to a pixel reaches an extreme value at the edge. The Sobel operator may have a smoothing effect on noise and may provide more accurate edge positioning information. However, the edge positioning information may be not accurate enough. In some embodiments, when an accuracy requirement for the X-ray image is not very high, the Sobel operator may be a common edge detection method.

In some embodiments, the processing device 120 may obtain the strong gradient image by removing scattered points and small boundary points from the boundary gradient image. In some embodiments, the processing device 120 may determine areas of connection regions of all boundary points in the boundary gradient image. The processing device 120 may determine the connection region having an area less than a predetermined area threshold as the small boundary points or scattered points. The processing device 120 may generate the strong gradient image by removing the small boundary points or scattered points from the boundary gradient image.

It should be noted that the predetermined gradient threshold and the predetermined area threshold may be determined by a user of the imaging system 100 according to actual conditions and empirical values. For example, the predetermined gradient threshold and the predetermined area threshold may be within a range from 0 to 1.

In 2630, the processing device 120 (e.g., the processor 220, the metal image determining module 420, the metal image determining unit 2420) may determine an average gray value of pixels at gradient positions corresponding to the strong gradient image based on the X-ray image.

In some embodiments, the processing device 120 may determine the gray values of the pixels at the gradient positions in the strong gradient image by comparing the strong gradient image with the X-ray image. The processing device 120 may determine a histogram corresponding to the gradient positions. In some embodiments, the processing device 120 may determine the average gray value (or the average gray value at the gradient positions corresponding to the strong gradient image) based on the gray value within 30% of gray values in the histogram.

In 2640, the processing device 120 (e.g., the processor 220, the metal image determining module 420, the metal image determining unit 2420) may determine a peak of a grayscale histogram of the X-ray image.

In some embodiments, the processing device 120 may determine the grayscale histogram of the X-ray image by statistics. The processing device 120 may determine an obvious peak section from the grayscale histogram.

In 2650, the processing device 120 (e.g., the processor 220, the metal image determining module 420, the metal image determining unit 2420) may determine a gray value with respect to the peak.

In some embodiments, the processing device 120 may determine the corresponding gray value of the obvious peak.

In 2660, the processing device 120 (e.g., the processor 220, the metal image determining module 420, the metal image determining unit 2420) may determine whether the X-ray image includes the metal information based on the average gray value and the gray value of the peak.

In some embodiments, the processing device 120 may compare the average gray value of pixels at gradient positions with the gray value of the peak. If the average gray value is close to the gray value, or a difference therebetween is less than a predetermined threshold, the X-ray image may include the metal region. The processing device 120 may determine that there may be a large-area metal region in the X-ray image. The predetermined threshold may be determined by the user according to actual conditions. The average gray value being close to the gray value may indicate that there is a strong boundary point in the low grayscale peak region. In some embodiments, a region having more than 20% of an area of the X-ray image may be considered as a large-area region (also referred to as a large region).

In 2670, in response to a determination that the X-ray image includes the metal information, the processing device 120 (e.g., the processor 220, the metal image determining module 420, the metal image determining unit 2420) may determine at least one segmented image by segmenting the X-ray image based on a predetermined image size.

In some embodiments, if the X-ray image includes the metal region, the processing device 120 may segment the X-ray image into the at least one segmented image. Each of the at least one segmented image may have a predetermined image size. In some embodiments, the predetermined image size may be determined according to actual conditions. For example, the predetermined image size may be 32*32. In some embodiments, the X-ray image may be completely segmented. To ensure that the X-ray image is completely segmented, the at least one segmented image may have different sizes. The at least one segmented image may not overlap with each other.

In 2680, the processing device 120 (e.g., the processor 220, the metal image determining module 420, the metal image determining unit 2420) may determine the metal image based on an average gray value and a variance with respect to each of the at least one segmented image.

In some embodiments, the processing device 120 may determine the average gray value of each of the at least one segmented image and the variance of each of the at least one segmented image. The processing device 120 may determine a relative variance of each segmented image according to Equation (3):

$$\text{relative variance} = \text{variance}/\text{average gray value} \quad (3).$$

Figure 28:
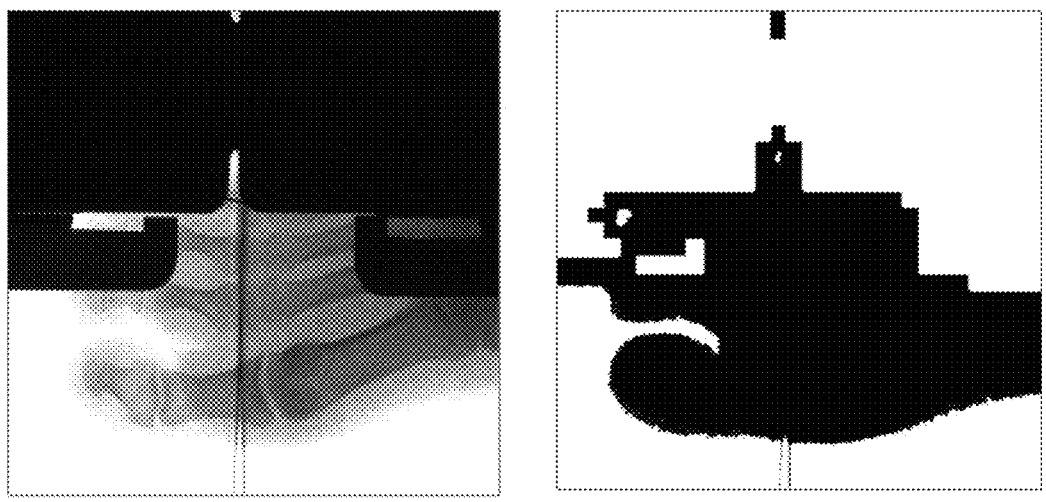
FIG. 28 illustrates an exemplary X-ray image and an exemplary metal image corresponding to the X-ray image according to some embodiments of the present disclosure.

In some embodiments, the processing device 120 may determine a position of the metal region based on the relative variance and the average gray value of each segmented image. FIG. 28 illustrates an exemplary X-ray image and an exemplary metal image corresponding to the X-ray image according to some embodiments of the present disclosure. The X-ray image is on the left side of FIG. 28, and a white region in the right image (the metal image) is a metal region determined according to some embodiments of the present disclosure.

In 2690, in response to a determination that the X-ray image includes the metal information, the processing device 120 (e.g., the processor 220, the metal image determining module 420, the metal image determining unit 2420) may determine that the X-ray image does not include metal information.

Figure 29:
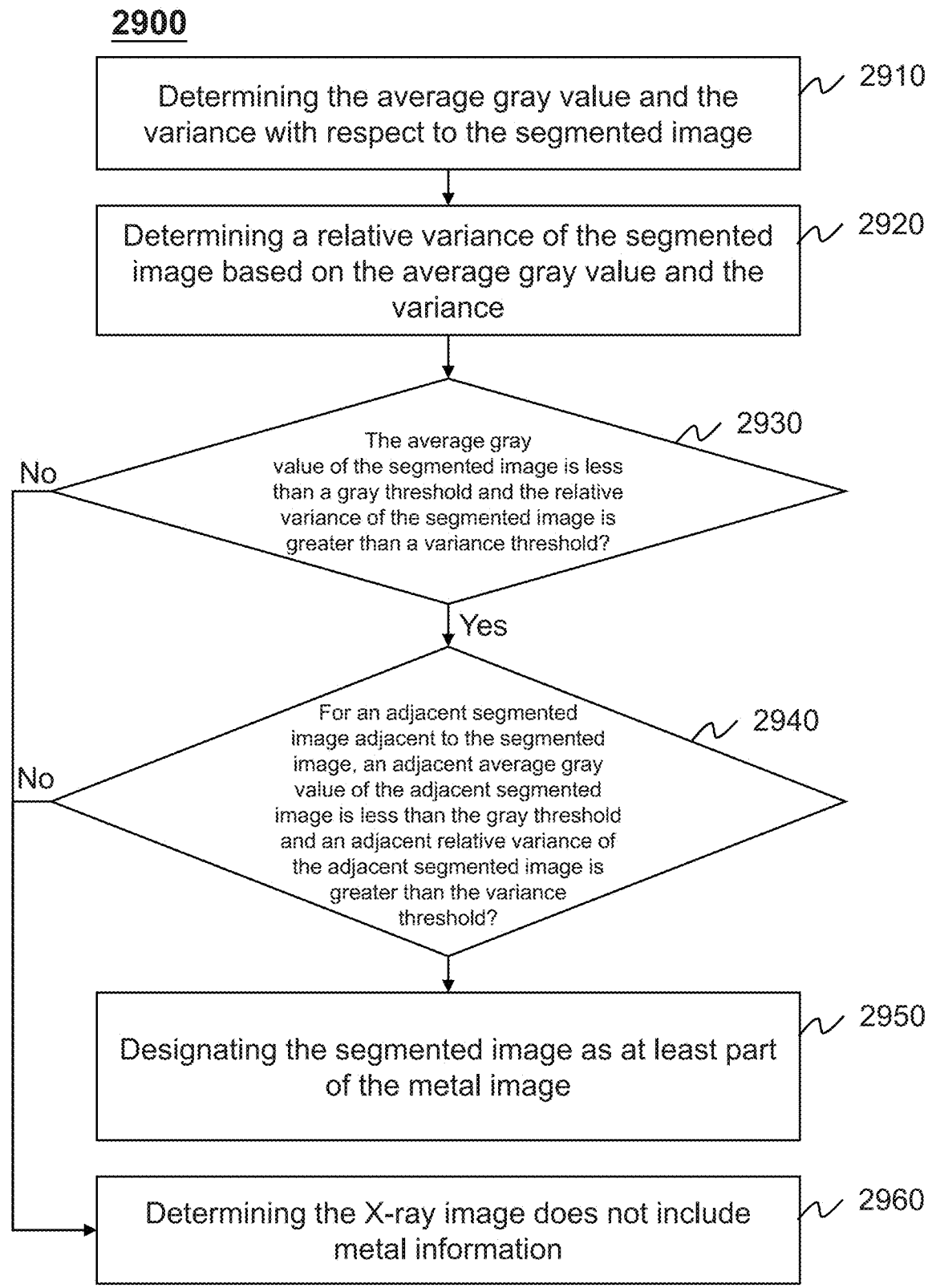
FIG. 29 is a flowchart illustrating an exemplary process for determining a metal image according to some embodiments of the present disclosure.

FIG. 29 is a flowchart illustrating an exemplary process 2900 for determining a metal image according to some embodiments of the present disclosure. The process 2900 may be executed by the imaging system 100. For example, the process 2900 may be implemented as a set of instructions (e.g., an application) stored in the storage ROM 230 or RAM 240. The processor 220 may execute the set of instructions, and when executing the instructions, it may be configured to perform the process 2900. The operations of the illustrated process presented below are intended to be illustrative. In some embodiments, the process 2900 may be accomplished with one or more additional operations not described and/or without one or more of the operations discussed. Additionally, the order in which the operations of the process as illustrated in FIG. 29 and described below is not intended to be limiting.

In some embodiments, the process 2900 may be performed on each of the at least one segmented image. In 2910, for each of the at least one segmented image, the processing device 120 (e.g., the processor 220, the metal image determining module 420, the metal image determining unit 2420) may determine the average gray value and the variance with respect to the segmented image.

In 2920, the processing device 120 (e.g., the processor 220, the metal image determining module 420, the metal image determining unit 2420) may determine a relative variance of the segmented image based on the average gray value and the variance.

In 2930, the processing device 120 (e.g., the processor 220, the metal image determining module 420, the metal image determining unit 2420) may determine whether the average gray value of the segmented image is less than a gray threshold and the relative variance of the segmented image is greater than a variance threshold.

In 2940, in response to a determination that the average gray value of the segmented image is less than the gray threshold and the relative variance of the segmented image is greater than the variance threshold, for an adjacent segmented image adjacent to the segmented image, the processing device 120 (e.g., the processor 220, the metal image determining module 420, the metal image determining unit 2420) may determine whether an adjacent average gray value of the adjacent segmented image is less than the gray threshold and an adjacent relative variance of the adjacent segmented image is greater than the variance threshold.

In 2950, in response to a determination that the adjacent average gray value is less than the gray threshold and the adjacent relative variance is greater than the variance threshold, the processing device 120 (e.g., the processor 220, the metal image determining module 420, the metal image determining unit 2420) may designate the segmented image as at least part of the metal image.

In 2960, in response to a determination that both the average gray value of the segmented image and the adjacent average gray value are less than the gray threshold and both the relative variance of the segmented image and the adjacent relative variance are greater than the variance threshold the processing device 120 (e.g., the processor 220, the metal image determining module 420, the metal image determining unit 2420) may determine that the X-ray image does not include metal information.

In some embodiments, different regions may be represented by the grayscale features. The average gray value and the relative variance of a segmented image may reflect image features (e.g., a content, details, a texture of the image, etc.). In some embodiments, the processing device 120 may determine whether the segmented image is at least part of the metal image at the corresponding position in the X-ray image by determining the average gray value and relative variance of the segmented image. In this way, the determination accuracy of the metal image may be improved.

In some embodiments, the processing device 120 may instruct the client terminal 140 to display a determination result on the X-ray image. The determination result may indicate whether each segmented image is at least part of the metal image corresponding to the X-ray image, thereby generating the metal image. In some embodiments, the determination result of each segmented image may be displayed at the corresponding position of the X-ray image. Each segmented image may be pieced together and restored to the metal image corresponding to the X-ray image. The metal image may include the metal region. In some embodiments, the metal image may be restored according to other ways and is not limited in the present disclosure.

Figure 30:
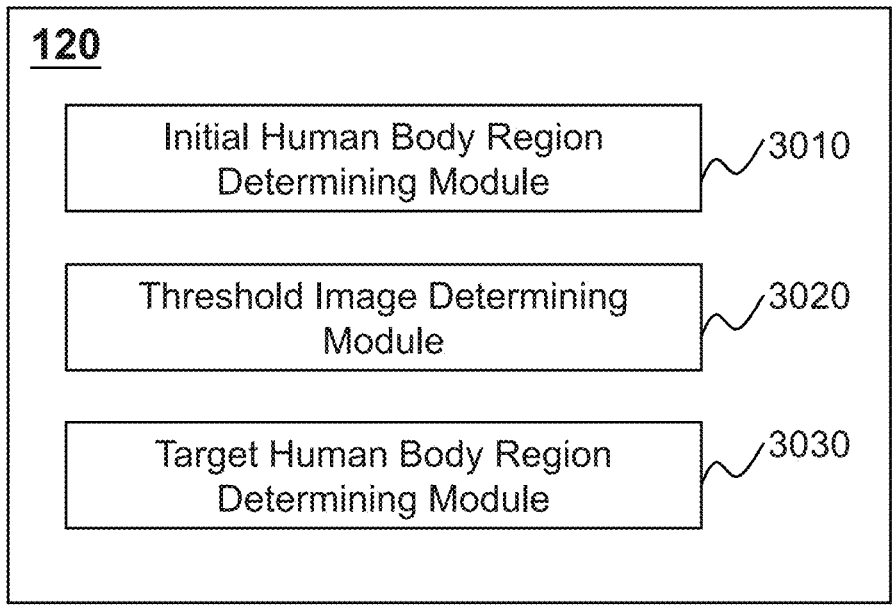
FIG. 30 is a block diagram illustrating an exemplary processing device according to some embodiments of the present disclosure.

FIG. 30 is a block diagram illustrating an exemplary processing device 120 according to some embodiments of the present disclosure. As illustrated in FIG. 30, the processing device 120 may include an initial human body region determining module 3010, a threshold image determining module 3020, and a target human body region determining module 3030.

The initial human body region determining module 3010 may be configured to determine an initial human body region in an X-ray image.

The threshold image determining module 3020 may be configured to determine a threshold image of the X-ray image. In some embodiments, the threshold image determining module 3020 may determine the threshold image based on pixel values of the initial human body region. In some embodiments, a threshold pixel in the threshold image may correspond to one or more pixels in the initial human body region.

The target human body region determining module 3030 may be configured to determine a target human body region in the X-ray image. In some embodiments, the target human body region determining module 3030 may determine whether pixels in the initial human body region are target pixels in the target human body region based on the threshold image.

Figure 31:
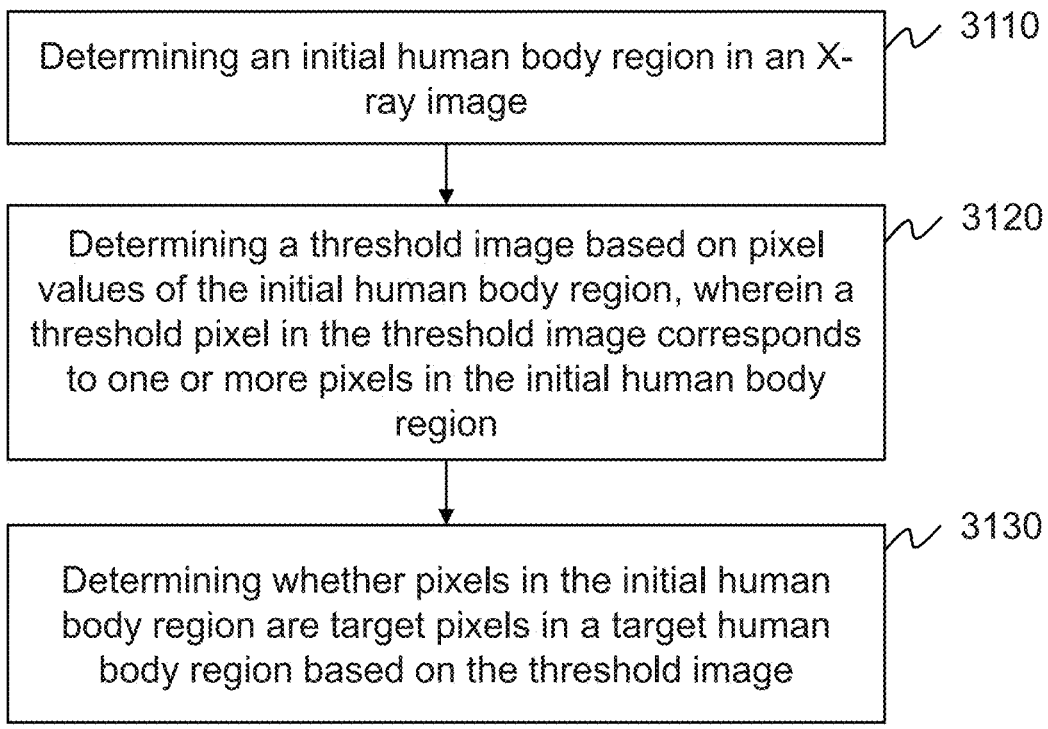
FIG. 31 is a flowchart illustrating an exemplary process for determining a target human body region in an X-ray image according to some embodiments of the present disclosure.

FIG. 31 is a flowchart illustrating an exemplary process 3100 for determining a target human body region in an X-ray image according to some embodiments of the present disclosure. The process 3100 may be executed by the imaging system 100. For example, the process 3100 may be implemented as a set of instructions (e.g., an application) stored in the storage ROM 230 or RAM 240. The processor 220 may execute the set of instructions, and when executing the instructions, it may be configured to perform the process 3100. The operations of the illustrated process presented below are intended to be illustrative. In some embodiments, the process 3100 may be accomplished with one or more additional operations not described and/or without one or more of the operations discussed. Additionally, the order in which the operations of the process as illustrated in FIG. 31 and described below is not intended to be limiting.

In 3110, the processing device 120 (e.g., the processor 220, the initial human body region determining module 3010) may determine an initial human body region in an X-ray image.

In some embodiments, the X-ray image may be an output image of the medical device 110 (e.g., an X-ray image, a CT image, a digital radiography (DR) image, a fluoroscopic image outputted by a mobile C-arm device, a fluoroscopic image outputted by a digital subtraction angiography (DSA) device, etc.). In some embodiments, the output image may be a first image outputted by a real-time imaging device during an imaging process, or other output images during the real-time imaging process.

In some embodiments, the initial human body region may be an image region where a human body part is located. In some embodiments, the initial human body region may include an extraneous intervention object. In some embodiments, the human body part may include a tissue, an organ, a body part of a subject, or the like, or any combination thereof. For example, the tissue may include a muscle tissue, a nerve tissue, a bone tissue, an epithelial tissue, or the like, or any combination thereof. The organ may include a heart, a liver, a lung, a stomach, a kidney, or the like, or any combination thereof. The body part may include a head, a hand, an arm, a foot, a calve, a thigh, an abdomen, a chest, or the like, or any combination thereof. In some embodiments, the extraneous intervention object may include a human implant, e.g., a metal bracket, a skull metal lock, a skull metal plate, an in vivo induction chip, a cardiac pacemaker, or the like, or any combination thereof.

Figure 34:
FIG. 34 illustrates an exemplary X-ray image of a human body region according to some embodiments of the present disclosure.

In some embodiments, the processing device 120 may determine a non-beam limiter region in the X-ray image. The non-beam limiter region may refer to a remaining region in the X-ray image other than a beam limiter region. The beam limiter region may refer to a region in the X-ray image where rays are blocked by a beam limiter. In some embodiments, due to the scattering of the rays, some scattered rays may be projected on the beam limiter region, which results in that image gray values in the beam limiter region do not equal to zero, thereby generating a region with low image gray values (but not equal to zero). FIG. 34 illustrates an exemplary X-ray image of a human body region according to some embodiments of the present disclosure. As shown in FIG. 34, 3410 represents a beam limiter region and 3420 represents a non-beam limiter region.

In some embodiments, the processing device 120 may determine the non-beam limiter region in the X-ray image according to an actual position of the beam limiter. For example, the processing device 120 may obtain a position of the beam limiter fed back by the medical device 110, and determine the non-beam limiter region in the X-ray image based on the position of the beam limiter. In some embodiments, the position of the beam limiter may include a position of the beam limiter relative to the medical device 110, a position of the beam limiter relative to a radiation generation device (e.g., a bulb of the medical device 110), and/or a position of the beam limiter relative to a radiation receiving device (e.g., a detector of the medical device 110). In some embodiments, the position of the beam limiter may include an opening and closing condition of the beam limiter (e.g., a rotation angle of the beam limiter, an opening size of the beam limiter, an opening shape of the beam limiter, etc.). In some embodiments, the position of the beam limiter may relatively fixed with respect to positions of the medical device 110, the radiation generation device, and/or the radiation receiving device. The above mentioned one or more relative positions may be obtained according to parameters of the imaging device 110 or through experiments. The data related to the opening and closing condition of the beam limiter may be obtained by the medical device 110 and fed back to the processing device 120.

Figure 36:
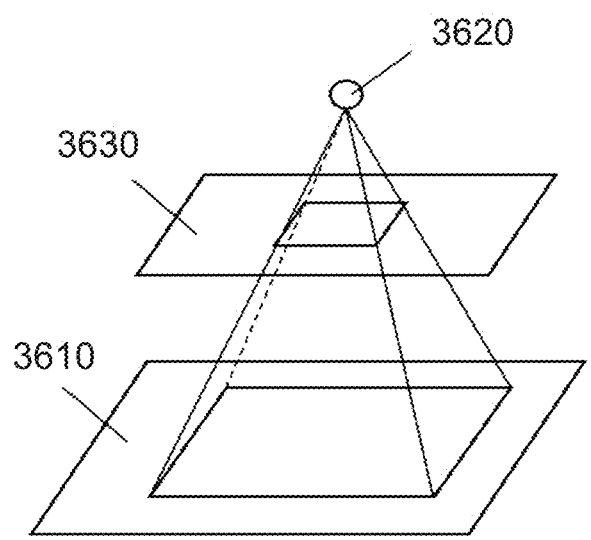
FIG. 36 is a schematic diagram illustrating exemplary an exemplary beam limiter according to some embodiments of the present disclosure.

In some embodiments, the processing device 120 may determine a curve equation of a boundary of the beam limiter region in the X-ray image based on the position of the beam limiter and an edge shape of the beam limiter. The processing device 120 may further determine pixels on the edge of the beam limiter in the X-ray image according to the curve equation. The processing device 120 may delimit the X-ray image according to an edge curve of the beam limiter to obtain the non-beam limiter region in the X-ray image. In some embodiments, the edge of the beam limiter may be a straight edge, a polygonal edge, a curved edge, or the like, or any combination thereof. FIG. 36 is a schematic diagram illustrating exemplary an exemplary beam limiter according to some embodiments of the present disclosure. As shown in FIG. 36, the edge of the beam limiter may be a straight edge. In some embodiments, a shape of the edge of the beam limiter in the X-ray image may be a straight edge, a polygon edge, a curved edge, or the like, or any combination thereof. The curve equation corresponding to the edge may include a straight line equation, a broken line equation, a smooth curve equation, or the like, or any combination thereof. In some embodiments, the curve equation may reflect a relationship between horizontal and vertical coordinates of the pixels on the edge of the beam limiter in the X-ray image. In some embodiments, the processing device 120 may determine the curve equation of the edge of the beam limiter in the X-ray image according to the position of the beam limiter. For example, the processing device 120 may determine the curve equation of the edge of the beam limiter in the X-ray image based on the position of the beam limiter and relative positions of various components (e.g., the detector and/or the radiation generation device) in the medical device 110. As another example, the processing device 120 may obtain the opening and closing condition of the beam limiter fed back by the medical device 110 to determine the position of the edge of the beam limiter. The processing device 120 may further determine the curve equation of the edge of the beam limiter in the X-ray image according to a principle of projection geometry based on a position of the beam limiter relative to the radiation generation device and a position of the detective device relative to the radiation generation device. For example, the processing device 120 may determine the opening and closing condition of the beam limiter through a signal fed back by a control motor of the beam limiter. In some embodiments, the control motor may feedback a rotation angle of the beam limiter and a distance between the edge of the beam limiter and a reference axis (e.g., a main optical axis) of a ray beam. In some embodiments, the edge of the beam limiter may be a straight line, so that the edge of the beam limiter region in the X-ray image may be expressed by a straight line equation. A slope of the straight line equation may be determined based on the rotation angle of the beam limiter. An intercept of the straight line equation may be determined based on a distance between the edge of the beam limiter and a reference axis of the ray beam (i.e., a distance of the straight line equation in the X-ray image relative to a certain reference point of the X-ray image, such as the center of the X-ray image). In some embodiments, the processing device 120 may determine the straight line equation of the beam limiter edge in the X-ray image. In some embodiments, the processing device 120 may determine the non-beam limiter region in an output image according to the curve equation of the edge of the beam limiter in the X-ray image. For example, as shown in FIG. 34, the processing device 120 may determine that a region on the right side of the X-ray image enclosed by the edge of the beam limiter is the non-beam limiter region based on the curve equation of the edge of the beam limiter in the X-ray image.

In some embodiments, the processing device 120 may determine the non-beam limiter region in the X-ray image according to other processes. For example, the patent document U.S. Pat. No. 7,747,058B2 discloses a process for determining the non-beam limiter region in an X-ray image based on an average value and a standard deviation of the gray value of each region of the X-ray image. As another example, the patent document U.S. Pat. No. 7,747,058B2 discloses a process for segmenting an X-ray image into image blocks and determining a non-beam limiter of the X-ray image by performing a frequency domain analysis on the X-ray image blocks. Compared with the process in prior art, the beam limiter region and the non-beam limiter region may be accurately segmented by determining the beam limiter region in the X-ray image based on the position of the beam limiter in the X-ray image fed back by the medical device 110. The target human body region in the X-ray image may be accurately determined.

Figure 35:
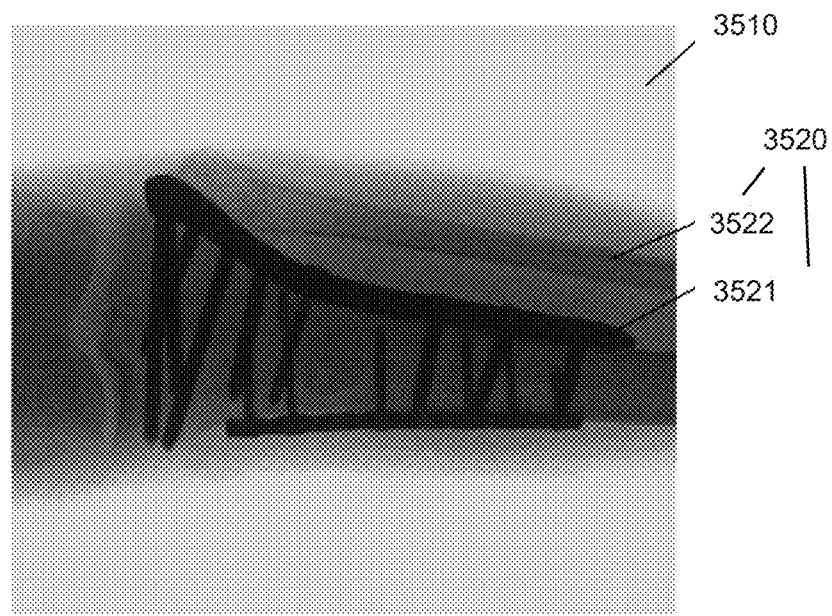
FIG. 35 illustrates an exemplary X-ray image of a human body region according to some embodiments of the present disclosure.

In some embodiments, the processing device 120 may determine a direct exposure region in the non-beam limiter region. For example, the processing device 120 may determine the direct exposure region according to a threshold segmentation algorithm. For example, the threshold segmentation algorithm may include a histogram segmentation algorithm, a minimum error algorithm, a homogenization error segmentation algorithm, a maximum entropy segmentation algorithm, or the like, or any combination thereof. A part of the non-beam limiter area excluding the direct exposure area may be the initial human body region. In some embodiments, the direct exposure region may refer to a region generated in the output image by rays that are directly irradiated on the detector without passing through an attenuator (such as a human body). As shown in FIG. 34, a part of the non-beam limiter region 3420 excluding a palm is the direct exposure area 3421, and the remaining palm and the edge are the initial human body region 3422. FIG. 35 illustrates an exemplary X-ray image of a human body region according to some embodiments of the present disclosure. As shown in FIG. 35, a part excluding a leg is the direct exposure area 3510, and the remaining leg and the edge are the initial human body region 3520.

In some embodiments, the processing device 120 may determine the direct exposure region in the non-beam limiter region based on gray values of the non-beam limiter region using a maximum between-cluster variance segmentation algorithm. For example, the processing device 120 may determine a threshold by using the maximum between-cluster variance segmentation algorithm based on the gray values of the non-beam limiter region. A region having grey values greater than the threshold may be determined as the direct exposure region, and a region having grey values smaller than the threshold may be determined as the initial human body region. In some embodiments, the processing device 120 may determine the direct exposure region in the non-beam limiter region using other algorithms (e.g., a K-Means clustering algorithm, a K-Medoids clustering algorithm, a Clarans clustering algorithm, etc.) based on the gray values of the non-beam limiter region. In some embodiments, the gray values of the initial human body region and the direct exposure region may have a large difference, so the two regions in the non-beam limiter region have a large difference. Compared with other algorithms, by using the maximum between-cluster variance segmentation algorithm, the initial human body region and the direct exposure region may be determined more accurately.

In 3120, the processing device 120 (e.g., the processor 220, the threshold image determining module 3020) may determine a threshold image based on pixel values of the initial human body region. In some embodiments, a threshold pixel in the threshold image may correspond to one or more pixels in the initial human body region.

In some embodiments, a pixel value may be a gray value of an image. In some embodiments, the pixel value may also include a gray scale, a brightness, an RGB value, or the like, or any combination thereof. In some embodiments, the processing device 140 may segment the initial human body region into a plurality of sub-regions. The processing device 140 may determine a segment threshold of the sub-regions. The processing device 140 may perform a surface fitting based on the segment threshold to obtain the threshold image. An exemplary process for determining the threshold image may be found elsewhere (e.g., FIG. 32 and relevant descriptions thereof) in the present disclosure. In some embodiments, the pixel value of a pixel in the threshold image may represent a threshold of one or more pixels of the corresponding initial human body region. In some embodiments, a count of pixels in the threshold image may be equal to or less than a count of pixels of the initial human body region. For example, one pixel in the threshold image may correspond to a plurality of pixels (e.g., 2, 4, 9) of the initial human body region. As an example, in the initial human body region, the pixels may be evenly divided into a plurality of blocks according to rows and columns. For example, a block may include 9 pixels in three rows and three columns. The gray value of the block may be represented by an average value of the gray values of the 9 pixels. In some embodiments, the gray values of blocks in the same column direction may constitute a curve in a column direction, and the curves in a plurality of column directions may represent the threshold image of the entire initial human body region. In some embodiments, the curves in the multiple row directions or in the multiple column directions, or curves in the plurality of row and column directions may also be replaced by a curved surface. In some embodiments, the count of pixels in the threshold image may be equal to a count of segment thresholds.

In 3130, the processing device 120 (e.g., the processor 220, the target human body region determining module 3030) may determine whether pixels in the initial human body region are target pixels in a target human body region based on the threshold image.

In some embodiments, the processing device 120 may compare a pixel value of a pixel in the initial human body region or a pixel operation value of a plurality of pixels in the initial human body region with a pixel value of a corresponding pixel in the threshold image. In response to a determination that the pixel value of the pixel in the initial human body region or the pixel operation value of the plurality of pixels in the initial human body region satisfies a threshold condition (e.g., greater or less than the pixel value of a corresponding pixel in the threshold image), the processing device 120 may determine that the pixel or the plurality of pixels in the initial human body region are not the target pixel(s) in the target human body region.

In some embodiments, the pixel operation value of the plurality of pixels may characterize the pixel value of a region where the plurality of pixels are located. In some embodiments, the pixel operation value of the plurality of pixels may be an average value (e.g., an arithmetic average value or a weighted average value) of the pixel values of the plurality of pixels. In some embodiments, the pixel operation value of the plurality of pixels may be a comprehensive value determined by other algorithms (e.g., a median value, an average value of the region using a fitting algorithm).

In some embodiments, the processing device 120 may compare a pixel value of a pixel in the initial human body region or a pixel operation value of a plurality of pixels in the initial human body region with a pixel value of a corresponding pixel in the threshold image, respectively. For example, if a count of pixels in the initial human body region is equal to a count of pixels in the threshold image, the processing device 120 may compare the pixel value of each pixel in the initial human body region with the pixel value of the corresponding pixel in the threshold image to determine whether each pixel in the initial human body region is a target pixel in the target human body region. If the count of the pixels in the initial human body region is smaller than the count of the pixels in the threshold image, the processing device 120 may compare the pixel value of each pixel in the initial human body region with the pixel value of the corresponding pixel in the threshold image to determine whether the plurality of pixels in the initial human body region are the target pixels in the target human body region. If the count of the pixels in the initial human body region is greater than the count of the pixels in the threshold image, the processing device 120 may determine a pixel operation value of the pixels in the initial human body region, and compare the pixel operation value with the pixel value of the corresponding pixel in the threshold image to determine whether the plurality of pixels in the initial human body region are the target pixels in the target human body region.

In some embodiments, the processing device 120 may remove the pixels that are not the target pixels from the initial human body region to obtain the target human body region. As shown in FIG. 35, the initial human body region 3520 may include a human implant (e.g., a metal stent). Since an attenuation of the human implant to the rays may be greater than an attenuation of human tissue (e.g., a bone tissue, a muscle tissue), the pixel values (or the gray values) of the human implant in the output image may be less than the pixel values of the human tissue. In some embodiments, the processing device 120 may compare a pixel value of a pixel in the initial human body region 3520 or a pixel average value of a plurality of pixels in the initial human body region 3520 with a pixel value of a corresponding pixel in the threshold image. If the pixel value of the pixel in the initial human body region 3520 or the pixel average value of the plurality of pixels in the initial human body region 3520 are less than the pixel value of a corresponding pixel in the threshold image, the pixel or the plurality of pixels in the initial human body region 3520 may be designated as the target pixels of the human implant region 3521 (rather than the target human body region). If the pixel value of a pixel in the initial human body region 3520 or the pixel average value of the plurality of pixels in the initial human body region 3520 are greater than the pixel value of a corresponding pixel in the threshold image, the pixel or the plurality of pixels in the initial human body region 3520 may be designated to belong to the target human body region 3522. The target human body region herein refers to a region merely including the human body in the output image. If the human body includes an implant, a region of the human body including the implant in the output image may be considered not to belong to the target human body region. In some embodiments, the initial human body region may not contain any implants (as shown in FIG. 34), and the target human body region may be consistent with the initial human body region.

Figure 32:
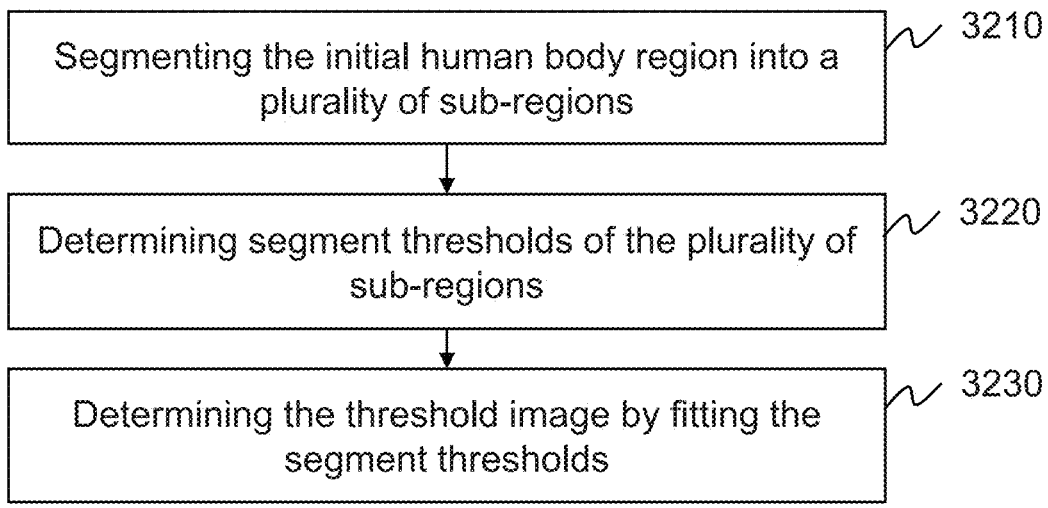
FIG. 32 is a flowchart illustrating an exemplary process for determining a threshold image according to some embodiments of the present disclosure.

FIG. 32 is a flowchart illustrating an exemplary process 3200 for determining a threshold image according to some embodiments of the present disclosure. The process 3200 may be executed by the imaging system 100. For example, the process 3200 may be implemented as a set of instructions (e.g., an application) stored in the storage ROM 230 or RAM 240. The processor 220 may execute the set of instructions, and when executing the instructions, it may be configured to perform the process 3200. The operations of the illustrated process presented below are intended to be illustrative. In some embodiments, the process 3200 may be accomplished with one or more additional operations not described and/or without one or more of the operations discussed. Additionally, the order in which the operations of the process as illustrated in FIG. 32 and described below is not intended to be limiting.

In 3210, the processing device 120 (e.g., the processor 220, the threshold image determining module 3020) may segment the initial human body region into a plurality of sub-regions.

In some embodiments, a sub-region may be in a regular shape (e.g., a square, a rectangular, a regular polygon), or an irregular shape. In some embodiments, the sub-region may include one or more pixels. For example, a count of sub-regions may be equal to or less than a count of pixels in the initial human body region. In some embodiments, a single pixel in the initial human body region may be considered as a sub-region. In some embodiments, the sub-region may include or may not include the target human body region.

In some embodiments, the initial human body region may be segmented into the plurality of sub-regions randomly, or be segmented into the plurality of sub-regions having an equal area or the same shape. In some embodiments, the sub-regions may not overlap each other. For example, there may be no common pixel between any two sub-regions. In some embodiments, the sub-regions may partially overlap each other. For example, at least two sub-regions may have a common pixel. In some embodiments, all of the plurality of sub-regions may be stitched together to generate the initial human body region. In some embodiments, all of the plurality of sub-regions may be stitched together to generate a part of the initial human body region.

In 3220, the processing device 120 (e.g., the processor 220, the threshold image determining module 3020) may determine segment thresholds of the plurality of sub-regions.

In some embodiments, a segment threshold of a sub-region may be an average pixel value of pixels of the sub-region, or a pixel value of a center pixel of the sub-region. When there is only one pixel in the sub-region, the segment threshold of the sub-region may be the pixel value of the pixel. In some embodiments, the segment threshold may be determined using a threshold segmentation algorithm. In some embodiments, the threshold segmentation algorithm may include a maximum between-cluster variance segmentation algorithm, a histogram-based segmentation algorithm, a minimum error algorithm, a homogenization error segmentation algorithm, a maximum entropy segmentation algorithm, or the like, or any combination thereof.

In 3230, the processing device 120 (e.g., the processor 220, the threshold image determining module 3020) may determine the threshold image by fitting the segment thresholds.

In some embodiments, a count of sub-regions may be less than or equal to a count of pixels in the initial human body region. For example, a count of segment thresholds may be less than or equal to the count of pixels in the initial human body region. The threshold image may be generated by performing the surface fitting algorithm on a segment threshold of each sub-region. In some embodiments, the surface fitting algorithm may include a least square algorithm, a quadratic polynomial fitting algorithm, a cubic polynomial fitting algorithm, or the like, or a combination thereof. In some embodiments, the processing device 120 may also perform the surface fitting algorithm on the segment threshold according to a surface type (e.g., a Gaussian-like surface) determined from historical data.

In some embodiments, the processing device 120 may obtain an initial surface equation. The processing device 120 may determine the surface equation corresponding to the threshold image by solving the initial surface equation based on the segment thresholds and position information thereof in the X-ray image. The processing device 120 may determine a pixel value of each pixel in the threshold image based on the surface equation corresponding to the threshold image. In some embodiments, the initial surface equation may be a surface equation pre-stored in the imaging system 100. For example, the initial surface equation may be determined by performing a fitting algorithm on the historical data. In some embodiments, the initial surface equation may include a Gaussian surface equation, a Bezier surface equation, a Bezier surface equation, a B-spline surface equation, or the like, or any combination thereof. In some embodiments, the position information of the segment threshold in the X-ray image may be expressed as pixel coordinate information of the segment threshold in the X-ray image. In some embodiments, the pixel coordinate information of the segment threshold may include pixel coordinate information of a pixel (e.g., a center point of a sub-region, a point in a neighborhood of the center point) in the corresponding sub-region. For example, the pixel coordinate information may be (50, 80), wherein 50 represents a position of the segment threshold in a horizontal coordinate (X axis) in the threshold image, and 80 represents a position of the segment threshold in a vertical coordinate (Y axis) in the threshold image. In some embodiments, the processing device 120 may determine the surface equation corresponding to the threshold image by solving the initial surface equation based on the segment threshold and the pixel coordinate information of the segment threshold in the X-ray image. In some embodiments, the processing device 120 may determine the pixel value of each pixel in the threshold image based on the surface equation corresponding to the threshold image. For example, the processing device 120 may input the segment threshold and the position information thereof in the X-ray image into the initial surface equation to solve the surface equation using a fitting algorithm. As another example, the processing device 120 may determine the pixel value of each pixel in the threshold image using the surface equation.

Figure 33:
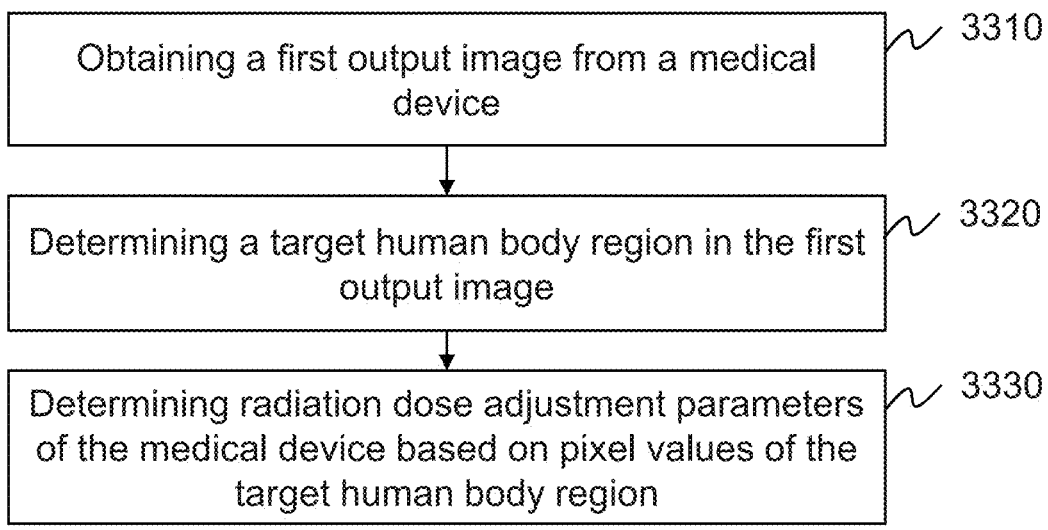
FIG. 33 is a flowchart illustrating an exemplary process for determining a radiation dose of a medical device according to some embodiments of the present disclosure.

FIG. 33 is a flowchart illustrating an exemplary process 3300 for determining a radiation dose of a medical device 110 according to some embodiments of the present disclosure. The process 3300 may be executed by the imaging system 100. For example, the process 3300 may be implemented as a set of instructions (e.g., an application) stored in the storage ROM 230 or RAM 240. The processor 220 may execute the set of instructions, and when executing the instructions, it may be configured to perform the process 3300. The operations of the illustrated process presented below are intended to be illustrative. In some embodiments, the process 3300 may be accomplished with one or more additional operations not described and/or without one or more of the operations discussed. Additionally, the order in which the operations of the process as illustrated in FIG. 33 and described below is not intended to be limiting.

In 3310, the processing device 120 (e.g., the processor 220) may obtain a first output image from the medical device 110.

In some embodiments, the medical device 110 may include a real-time fluoroscopy device. For example, the medical device 110 may include a mobile C-arm, a DSA device, an X-ray device, a DR device, a mobile DR device, a CT device, or the like, or any combination thereof. In some embodiments, the first output image may be a first image outputted by the real-time imaging device during an imaging process. In some embodiments, the first output image may be any other output images during the real-time imaging process.

In 3320, the processing device 120 (e.g., the processor 220) may determine a target human body region in the first output image.

In some embodiments, the target human body region in the first output image may be determined according to the process 3100 in the present disclosure.

In 3330, the processing device 120 (e.g., the processor 220) may determine radiation dose adjustment parameters of the medical device based on pixel values of the target human body region.

In some embodiments, a pixel value may include a gray value, a gray scale, a brightness, a RGB value, or the like, or any combination thereof. In some embodiments, the radiation dose adjustment parameters may include a tube voltage, a tube current, an effective time of the pulse, a product of the tube current and the effective time of the pulse in a radiation generation device of the medical device 110, or the like, or any combination thereof.

In some embodiments, the processing device 120 may determine the radiation dose adjustment parameter of the medical device 110 according to a difference between an average pixel value of the target human body region and a target pixel value. For example, the average pixel value may include an arithmetic average value of pixel values of all pixels in the target human body region in the first output image. The target pixel value may be a predetermined pixel value of the target human body region. In some embodiments, the target pixel value may be determined according to a standard, or an image type determined by a user. For example, the target pixel value may be an average pixel value of a predetermined human body region in a predetermined image provided by the user. In some embodiments, the processing device 120 may determine the radiation dose adjustment parameters of the radiation generating device in the medical device 110 according to the difference between the average pixel value of the target human body region and the target pixel value.

In some embodiments, the processing device 120 may adjust a radiation dose of the medical device 110 according to the radiation dose adjustment parameters to make the difference between the average pixel value of the target human body region and the target pixel value be less than a predetermined threshold. In some embodiments, the processing device 120 may obtain a second output image according to the adjusted radiation dose of the medical device 110. In some embodiments, the pixel value may be a gray value represented by 0 to 255 (where white is 255 and black is 0). In some embodiments, the predetermined threshold may be 3, 2, 1, etc. For example, the predetermined threshold may be 1. The radiation dose of the medical device 110 may be adjusted. The difference between the average pixel value of the target human body region and the target pixel value may be less than 1. In some embodiments, the pixel value may also be a gray value represented by 0 to 16383 (or 0~65535, etc.). The predetermined threshold may be adjusted accordingly. For example, when the pixel value is a gray value represented by 0 to 16383, the predetermined threshold may be 150, 128, 100, 64, 30, etc. In some embodiments, the second output image may be one or more images outputted by the medical device 110 after the first output image in the same imaging process. In some embodiments, the processing device 120 may obtain the second output image by adjusting the radiation dose of the medical device 110 once according to the radiation dose adjustment parameters of the medical device 110. A difference between the average pixel value of the target human body region in the second output image and the target pixel value may be less than the predetermined threshold. In some embodiments, the processing device 120 may adjust the radiation dose of the medical device 110 repeatedly according to the radiation dose adjustment parameters of the medical device 110, until a difference between the average pixel value of the target human body region in an output image and the target pixel value is less than the predetermined threshold. During the above repeated adjustments of the radiation dose of the medical device 110, the processing device 120 may modify the radiation dose adjustment parameters of the medical device 110 according to image information outputted during the process, and may adjust the radiation dose of the medical device 110 according to the modified radiation dose adjustment parameters, until a difference between the average pixel value of the target human body region in an output image and the target pixel value is less than the predetermined threshold. In the present disclosure, the target human body region and the pixel value of the target human body region in the X-ray image may be determined accurately by segmenting the may be accurate.

In some embodiments, the processing device 120 may determine the radiation dose adjustment parameters of the medical device 110 according to gray values of the target human body region and other parameters (e.g., a contrast ratio, a signal-to-noise ratio), and then obtain the second output image according to the adjusted radiation dose of the medical device 110. In some embodiments, the processing device 120 may determine a parameter reflecting an image display effect (e.g., a brightness, a contrast ratio) based on the pixel values of the target human body region. The processing device 120 may further compare the parameter reflecting the image display effect with a predetermined target value, and determine the radiation dose adjustment parameters of the medical device 110 based on a comparison result.

Figure 37:
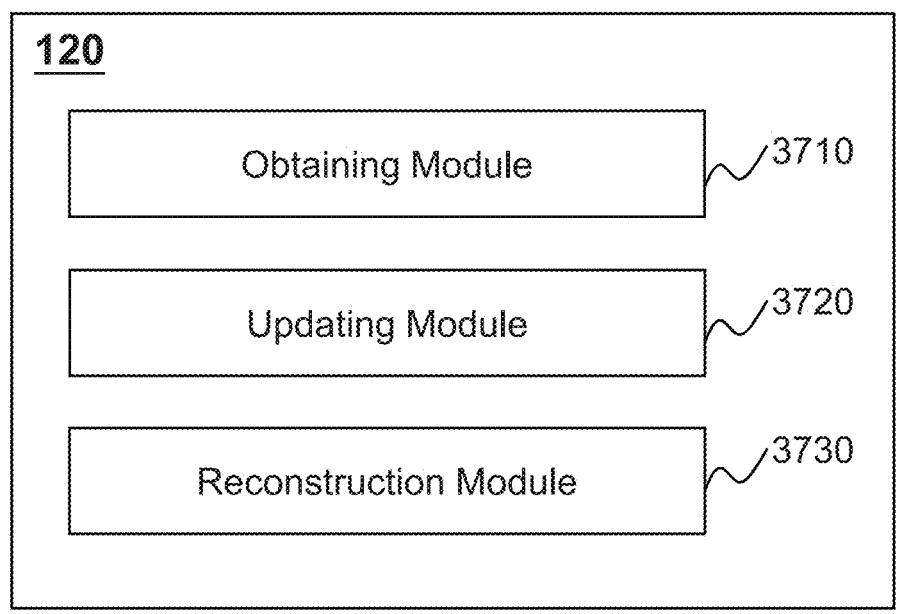
FIG. 37 is a block diagram illustrating an exemplary processing device according to some embodiments of the present disclosure.

FIG. 37 is a block diagram illustrating an exemplary processing device 120 according to some embodiments of the present disclosure. As illustrated in FIG. 37, the processing device 120 may include an obtaining module 3710, an updating module 3720, and reconstruction module 3730.

The obtaining module 3710 may be configured to obtain information relating to process an X-ray image. In some embodiments, the obtaining module 3710 may obtain initial projection data. In some embodiments, the obtaining module 3710 may obtain an exposure condition corresponding to the initial projection data.

The updating module 3720 may be configured to update the initial projection data. In some embodiments, the updating module 3720 may determine updated projection data based on at least one target bone-tissue thickness combination. In some embodiments, the at least one target bone-tissue thickness combination may be obtained by accessing a mapping database based on the initial projection data and the exposure condition.

The reconstruction module 3730 may be configured to determine a target X-ray image. In some embodiments, the reconstruction module 3730 may determine the target X-ray image by performing an image reconstruction based on the updated projection data.

Figure 38:
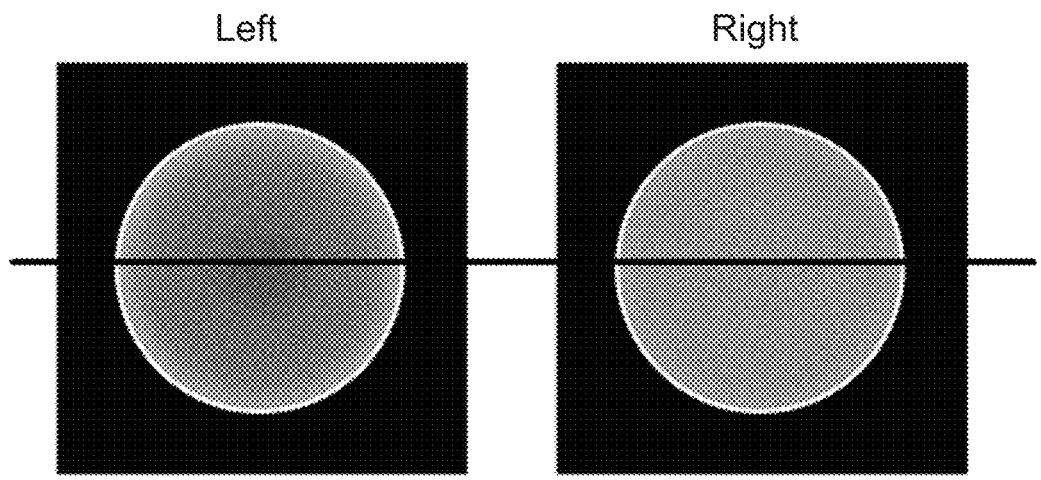
FIG. 38 illustrates exemplary reconstructed images according to some embodiments of the present disclosure.

FIG. 38 illustrates exemplary reconstructed images according to some embodiments of the present disclosure. As shown in FIG. 38, the reconstructed image on the left side is reconstructed based on projection data and the reconstructed image on the right side is an ideal reconstructed image. The reconstructed image on the left side may have obvious shadow in the middle part.

Figure 39:
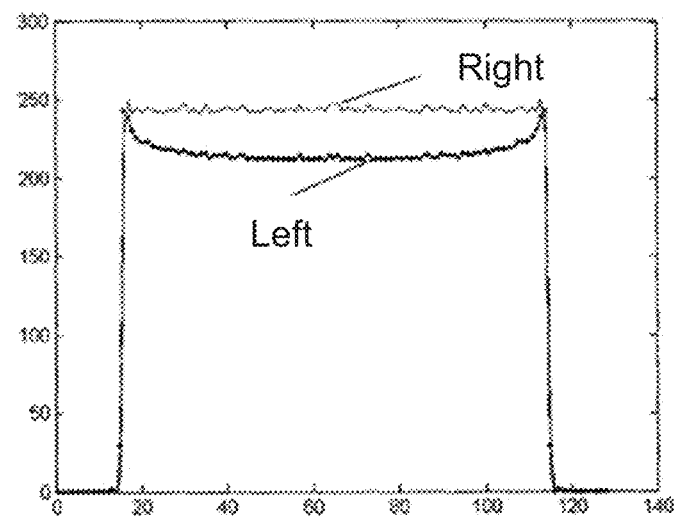
FIG. 39 illustrates exemplary diagrams of grayscale distribution of horizontal center lines of two reconstructed images according to some embodiments of the present disclosure.

FIG. 39 illustrates exemplary diagrams of grayscale distribution of horizontal center lines of two reconstructed images in FIG. 38 according to some embodiments of the present disclosure. As shown in FIG. 39, gray values of a middle part of a horizontal center line of the reconstructed image on the left side is less than those of a middle part of a horizontal center line of the reconstructed image on the right side.

Figure 40:
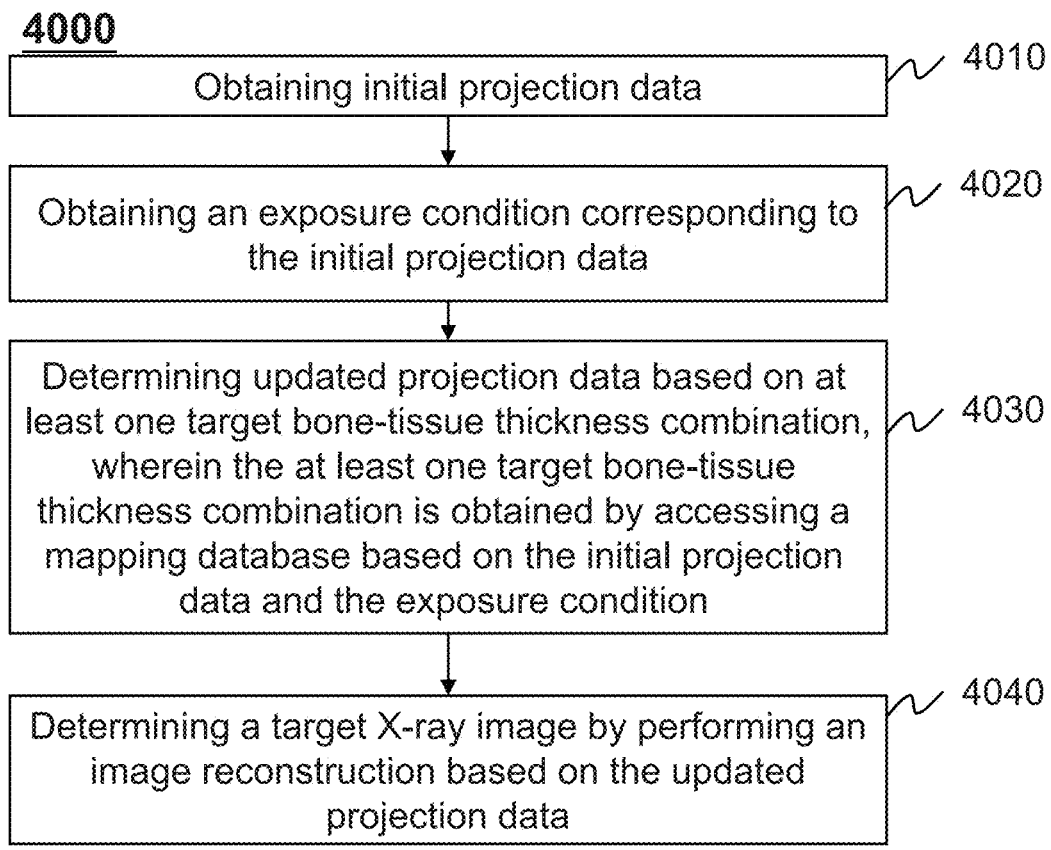
FIG. 40 is a flowchart illustrating an exemplary process for determining a radiation dose of a medical device according to some embodiments of the present disclosure.

FIG. 40 is a flowchart illustrating an exemplary process 4000 for determining a radiation dose of a medical device 110 according to some embodiments of the present disclosure. The process 4000 may be executed by the imaging system 100. For example, the process 4000 may be implemented as a set of instructions (e.g., an application) stored in the storage ROM 230 or RAM 240. The processor 220 may execute the set of instructions, and when executing the instructions, it may be configured to perform the process 4000. The operations of the illustrated process presented below are intended to be illustrative. In some embodiments, the process 4000 may be accomplished with one or more additional operations not described and/or without one or more of the operations discussed. Additionally, the order in which the operations of the process as illustrated in FIG. 40 and described below is not intended to be limiting.

In 4010, the processing device 120 (e.g., the processor 220, the obtaining module 3710) may obtain initial projection data.

During a scan on the subject, a radiation source may output X-rays to the subject. The X-rays may pass through the subject and enter into a detector. The detector may generate the initial projection data based on X-rays received by the detector. The initial projection data may include a plurality of projection values. For example, the initial projection data may include a unit projection value on a subject. For example, the initial projection data may include a unit bone projection value and a unit tissue projection value, or the like, or any combination thereof. In some embodiments, the unit bone projection value may be a projection value of a single energy X-ray passing through a unit-thickness bone. In some embodiments, the unit tissue projection value may be a projection value of a single energy X-ray passing through a unit-thickness tissue. In some embodiments, the tissue may include a soft tissue having a density less than that of the bone.

In 4020, the processing device 120 (e.g., the processor 220, the obtaining module 3710) may obtain an exposure condition corresponding to the initial projection data.

In some embodiments, before the medical device 110 scans the subject, the exposure condition of the medical device 110 may be preset. In some embodiments, the exposure condition may include a parameter of a radiation source with respect to the initial projection data. For example, the parameter may include a high voltage of the radiation source (kV), a current of the radiation source (mA), a continuous exposure time (s) of the radiation source, a scanning protocol of the radiation source, or the like, or any combination thereof. In some embodiments, the scanning protocol may include a scanning angle of the radiation source.

In 4030, the processing device 120 (e.g., the processor 220, the updating module 3720) may determine updated projection data based on at least one target bone-tissue thickness combination. In some embodiments, the at least one target bone-tissue thickness combination may be obtained by accessing a mapping database based on the initial projection data and the exposure condition.

During a scan of the medical device 110 on the subject, the X-rays outputted by the medical device 110 may pass through a tissue and a bone of the subject. Due to different densities of the tissue and the bone, the tissue and the bone may have different absorption capacities for the X-rays under a same exposure condition. In some embodiments, the exposure condition may be mainly reflected by a ray energy. In some embodiments, a scanning beam outputted by the medical device 110 may include a plurality of different X-rays energies. In some embodiments, low-energy X-rays may be more easily absorbed by the tissue and the bone than high-energy X-rays.

In some embodiments, under the same exposure condition, a unit bone projection value and a unit tissue projection value may be constant. If a bone thickness and a tissue thickness corresponding to each bone-tissue thickness combination are constant, the projection value of the corresponding bone-tissue thickness combination may be constant. A mapping database reflecting a mapping relation between reference bone-tissue thickness combinations and reference projection values may be stored in a storage device (e.g., the storage 130, the ROM 230, the RAM 240, etc.) of the imaging system 100. In some embodiments, after obtaining the initial projection data, the processing device 120 may access the mapping database to obtain the bone-tissue thickness combination corresponding to the initial projection value included in the initial projection data.

In some embodiments, the mapping database may be determined using polymethyl methacrylate (PMMA) or water to simulate a soft tissue of a human body, and calcium carbonate material or a material with a similar property thereof to simulate a bone of the human body. In some embodiments, under the same exposure condition, a mapping relation between the reference bone-tissue thickness combination and reference projection values may be established by modeling projection values corresponding to different thickness combinations of the calcium carbonate material and the PMMA (or the water). Table 1 illustrates an exemplary mapping table of a mapping database under a certain exposure condition. In some embodiments, the thicknesses of the bone and the tissue may be incremented by a predetermined thickness interval (e.g., 0.5 cm, 1 cm) as shown in Table 1.

TABLE 1

| Tissue Thickness (cm) | Bone thickness (cm) | Reference Projection Value |
|---|---|---|
| 5 | 2 | a1 |
| 5 | 3 | a2 |
| 5 | 4 | a3 |
| 5 | 5 | a4 |
| 6 | 2 | a5 |
| 6 | 3 | a6 |
| 6 | 4 | a7 |
| 6 | 5 | a8 |

Figure 41:
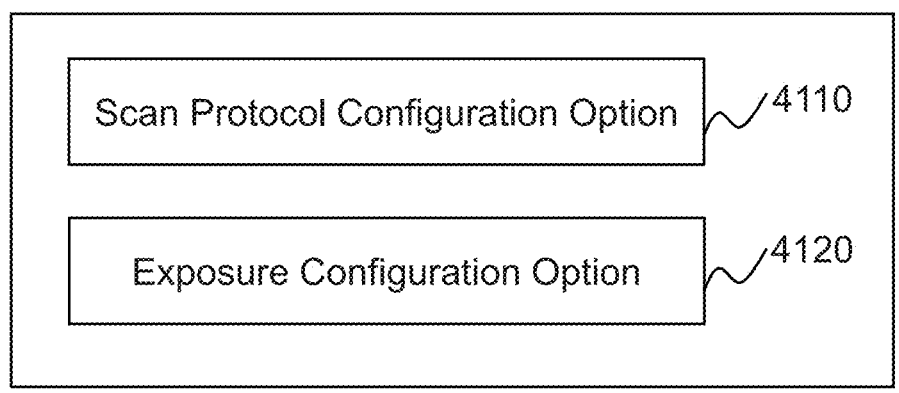
FIG. 41 illustrates an exemplary configuration interface according to some embodiments of the present disclosure.

In some embodiments, since the bone density and the tissue density of different organs or tissues are different, a mapping database corresponding to each exposure condition may be established for each scanning site protocol. In some embodiments, the mapping database may be determined based on the exposure condition and the scanning site protocol. Each projection value of the initial projection data in the mapping database may be determined, and the bone-tissue thickness combination may be determined based on the projection value. In some embodiments, the bone-tissue thickness combination corresponding to each projection value is unique. In some embodiments, before the medical device 110 scans the subject, a user may enter or select a scan site protocol in a scan protocol configuration option and the exposure condition in an exposure configuration option of a configuration interface. FIG. 41 illustrates an exemplary configuration interface according to some embodiments of the present disclosure. As shown in FIG. 41, the configuration interface may include a scan protocol configuration option 4110 and an exposure configuration option 4120. In some embodiments, the processing device may access the mapping database to obtain the corresponding mapping table according to the scanning site protocol and the exposure conditions. In some embodiments, the processing device 120 may obtain the mapping table based on configuration information. The complexity and configuration time of the scanning process is reduced.

In some embodiments, a slight difference between a phantom (e.g., PMMA, water, calcium carbonate material, etc.) used for determining the mapping database and a real human body may exist. In some embodiments, an individual difference between different human bodies may exist. The processing device 120 may not obtain the corresponding projection values directly in the mapping database. In some embodiments, for each of the at least one initial projection value of the initial projection data, the processing deice 120 may obtain a candidate bone-tissue thickness combination mapping from the mapping database. In some embodiments, the candidate bone-tissue thickness combination corresponds to a candidate reference projection value with a difference from the initial projection value less than a difference threshold. In some embodiments, the processing device 120 may obtain reference projection values that are closest to the projection values (e.g., difference values between the reference projection values and the projection values is the minimum in the mapping database), and designate a reference bone-tissue thickness combination of the reference projection values as the candidate bone-tissue thickness combination. In some embodiments, the processing device 120 may designate the candidate bone-tissue thickness combination as the target bone-tissue thickness combination corresponding to the initial projection value.

In some embodiments, under the same exposure condition, the unit bone projection value and the unit tissue projection value may be constant. Thus, if the exposure condition and each bone-tissue thickness combination are known, a corrected projection value corresponding to the target bone-tissue thickness combination may be determined according to Equation (4):

$$\text{corrected projection value} = \text{unit bone projection value} \times \text{bone thickness} + \text{unit tissue projection value} \times \text{tissue thickness} \qquad (4).$$

The initial projection data may be updated based on the corrected projection value corresponding to the bone-tissue thickness combination. The processing device 120 may obtain the updated projection data. In some embodiments, the projection value of the bone and the projection value of the tissue in the initial projection data may be corrected simultaneously. An accuracy of the updated initial projection data is improved by avoiding a correction deviation caused by mistaking the bone as a part of the soft tissue when a hydraulic hardening correction and a bone hardening correction are performed separately.

In some embodiments, in order to improve a speed of the hardening artifact correction, each bone-tissue thickness combination may be added in the mapping database. Once a bone-tissue thickness combination is determined, a modeled corrected projection value corresponding to the determined bone-tissue thickness combination may be taken as the corresponding corrected projection value to update the initial projection data.

In 4010, the processing device 120 (e.g., the processor 220, the reconstruction module 3730) may determine a target X-ray image by performing an image reconstruction based on the updated projection data.

In some embodiments, hardening corrections of the tissue and the bone may be performed and the target medical image may be generated by performing an image reconstruction only once. An efficiency of hardening correction may be improved. The time of hardening correction may be reduced. An image quality of the target medical image may be high, which helps to improve a clinical diagnosis effect.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system for processing an X-ray image, comprising:
at least one storage device including a set of instructions for processing an X-ray image; and
at least one processor in communication with the at least one storage device, wherein when executing the set of instructions, the at least one processor is directed to cause the system to perform operations including:
obtaining an X-ray image; and
determining a metal image based on the X-ray image by using a trained metal detection model, wherein the metal image includes information of a metal object in the X-ray image, and the information of the metal object includes at least one of a position of the metal object, a shape of the metal object, a size of the metal object, an orientation of the metal object, or a type of the metal object.

2. The system of claim 1, wherein the trained metal detection model is determined based on a training process, the training process including:
obtaining a sample set including a plurality of sample pairs, wherein each sample pair of the plurality of sample pairs includes a sample X-ray image and a labeled metal image with respect to the X-ray image; and
obtaining the trained metal detection model by training a preliminary metal detection model based on the sample set.

3. The system of claim 2, wherein the trained metal detection model includes a deep learning model.

4. The system of claim 3, wherein the deep learning model is a V-Net neural network model including a skip connection, wherein the skip connection includes:
combing at least one of at least one down-sampling feature corresponding to at least one down-sampling layer during up-sampling.

5. The system of claim 4, wherein the skip connection further includes:
in each up-sampling layer of a plurality of up-sampling layers, combing a down-sampling feature of a down-sampling layer corresponding to the up-sampling layer and a refined feature of the down-sampling feature.

6. The system of claim 4, wherein a loss function of the V-Net neural network model is an FL loss function determined based on a Focal Loss function and a Lovasz Loss function.

7. The system of claim 1, wherein the determining the metal image based on the X-ray image by using the trained metal detection model includes:
determining, by using the trained metal detection model, a probability graph representing a probability that a pixel in the X-ray image belongs to a metal region; and
determining the metal image based on the probability graph.

8. The system of claim 1, wherein the determining the metal image based on the X-ray image by using the trained metal detection model includes:
determining an initial binary image indicating an initial metal region by using the trained metal detection model, wherein the trained metal detection model is trained from a neural network model for category semantic perception; and
determining the metal image indicating a target metal region based on the initial binary image, wherein the metal image is a target binary image.

9. The system of claim 8, wherein the determining the metal image indicating the target metal region based on the initial binary image includes:
determining whether the initial metal region is a connected region;
in response to a determination that the initial metal region is the connected region, obtaining the target metal region by filling the initial metal region according to a morphological reconstruction algorithm; and
in response to a determination that the initial metal region is a dis-connected region,
determining a target region edge by performing an edge connection processing on an initial edge of the initial metal region according to a predetermined edge processing algorithm; and
obtaining the target metal region by filling a region within the target region edge according to the morphological reconstruction algorithm.

10. The system of claim 8, wherein the trained metal detection model is determined based on a training process, the training process including:
obtaining a sample set including a plurality of sample pairs, wherein each sample pair of the plurality of sample pairs includes a sample X-ray image and a reference binary image indicating a reference metal region with respect to the X-ray image;
obtaining the trained metal detection model by training a preliminary metal detection model based on the sample set, wherein
the preliminary metal detection model is the neural network model for category semantic perception,
model parameters of the preliminary metal detection model include initial model parameters of the neural network model for category semantic perception, the initial model parameters including a random number based on a zero mean and a predetermined variance, and a loss function of the preliminary metal detection model includes a multi-category comparison loss function of the neural network model for category semantic perception.

11. The system of claim 8, wherein the neural network model for category semantic perception includes:
an initial feature extraction structure including a first convolution layer, at least three transition layers, a plurality of residual blocks, and a second convolution layer, wherein
each of the plurality of residual blocks connects to a respective one of the at least three transition layers,
each of the plurality of residual block is used to generate a first initial feature,
the second convolution layer is used to generate a second initial feature, and
the second convolution layer includes interpolations and convolutions,
a fusion feature extraction structure including at least one up-sampling layer, wherein for each of the at least one up-sampling layer,
the up-sampling layer includes at least one transposed convolution,
the up-sampling layer connects to a residual block of the plurality of residual blocks, and
the up-sampling layer is used to generate a fusion feature by performing a secondary feature extraction on the first initial feature generated by the residual block; and
a feature fusion structure connecting to the second convolution layer and each of the at least one up-sampling layer, wherein the feature fusion structure is used to generate the initial binary image by fusing the second initial feature generated by the second convolution layer and the fusion feature generated by each of the at least one up-sampling layer.

12. The system of claim 11, wherein
a first count of the at least one up-sampling layer equals to a second count of the plurality of residual blocks, and
for a first residual block deeper than a second residual block, a third count of at least one transposed convolution of an up-sampling layer connected to the first residual block is greater than or equals to a fourth count of at least one transposed convolution of an up-sampling layer connected to the second residual block.

13. The system of claim 12, wherein
the initial feature extraction structure includes a superficial-layer residual block, an interlayer residual block, and a deep-layer residual block; and
the fusion feature extraction structure includes:
a first up-sampling layer connected to the superficial-layer residual block, wherein the first up-sampling layer includes one transposed convolution;
a second up-sampling layer connected to the interlayer residual block, wherein the second up-sampling layer includes two transposed convolutions; and
a third up-sampling layer connected to the deep-layer residual block, wherein the third up-sampling layer includes four transposed convolutions.

14. A system for processing an X-ray image, comprising:
at least one storage device including a set of instructions for processing an X-ray image; and
at least one processor in communication with the at least one storage device, wherein when executing the set of instructions, the at least one processor is directed to cause the system to perform operations including:
obtaining an X-ray image;
determining an initial binary image indicating an initial metal region by using a trained metal detection model based on the X-ray image, wherein the trained metal detection model is trained from a neural network model for category semantic perception; and
determining a metal image indicating a target metal region based on the initial binary image, wherein the metal image is a target binary image, and the metal image includes information of a metal object in the X-ray image, and the information of the metal object includes at least one of a position of the metal object, a shape of the metal object, a size of the metal object, an orientation of the metal object, or a type of the metal object.

15. A method for processing an X-ray image, comprising:
obtaining an X-ray image; and
determining a metal image based on the X-ray image by using a trained metal detection model, wherein the metal image includes information of a metal object in the X-ray image, and the information of the metal object includes at least one of a position of the metal object, a shape of the metal object, a size of the metal object, an orientation of the metal object, or a type of the metal object.

16. The method of claim 15, wherein the trained metal detection model is determined based on a training process, the training process including:
obtaining a sample set including a plurality of sample pairs, wherein each sample pair of the plurality of sample pairs includes a sample X-ray image and a labeled metal image with respect to the X-ray image; and
obtaining the trained metal detection model by training a preliminary metal detection model based on the sample set.

17. The method of claim 16, wherein the trained metal detection model includes a deep learning model.

18. The method of claim 17, the deep learning model is a V-Net neural network model including a skip connection, wherein the skip connection includes:
combing at least one of at least one down-sampling feature corresponding to at least one down-sampling layer during up-sampling.

19. The method of claim 15, wherein the determining the metal image based on the X-ray image by using the trained metal detection model includes:
determining, by using the trained metal detection model, a probability graph representing a probability that a pixel in the X-ray image belongs to a metal region; and
determining the metal image based on the probability graph.

20. The method of claim 15, wherein the determining the metal image based on the X-ray image by using the trained metal detection model includes:
determining an initial binary image indicating an initial metal region by using the trained metal detection model, wherein the trained metal detection model is trained from a neural network model for category semantic perception; and
determining the metal image indicating a target metal region based on the initial binary image, wherein the metal image is a target binary image.

* * * * *